(12) United States Patent
McDermott et al.

(10) Patent No.: US 10,245,254 B2
(45) Date of Patent: Apr. 2, 2019

(54) GLUTAMINASE INHIBITORS

(71) Applicants: University of Pittsburgh—Of the Commonwealth System of Higher Education, Pittsburgh, PA (US); Cornell University, Ithaca, NY (US)

(72) Inventors: Lee A. McDermott, Pittsburgh, PA (US); Prema C. Iyer, Pittsburgh, PA (US); Richard A. Cerione, Ithaca, NY (US); William P. Katt, Brooktondale, NY (US)

(73) Assignees: University of Pittsburgh—Of the Commonwealth System of Higher Education, Pittsburgh, PA (US); Cornell University, Ithaca, NY (US)

( * ) Notice: Subject to any disclaimer, the term of this patent is extended or adjusted under 35 U.S.C. 154(b) by 0 days.

(21) Appl. No.: 15/516,002

(22) PCT Filed: Oct. 1, 2015

(86) PCT No.: PCT/US2015/053514
§ 371 (c)(1),
(2) Date: Mar. 30, 2017

(87) PCT Pub. No.: WO2016/054388
PCT Pub. Date: Apr. 7, 2016

(65) Prior Publication Data
US 2017/0290815 A1 Oct. 12, 2017

Related U.S. Application Data

(60) Provisional application No. 62/059,707, filed on Oct. 3, 2014.

(51) Int. Cl.
*A61K 31/433* (2006.01)
*C07D 401/14* (2006.01)
(Continued)

(52) U.S. Cl.
CPC ........ *A61K 31/433* (2013.01); *A61K 31/4535* (2013.01); *C07D 285/135* (2013.01);
(Continued)

(58) Field of Classification Search
CPC .................................................. C07D 417/14
See application file for complete search history.

(56) References Cited

U.S. PATENT DOCUMENTS

2002/0115698 A1 8/2002 Newcomb et al.
2014/0142081 A1 5/2014 Lemieux et al.

FOREIGN PATENT DOCUMENTS

CN 103030597 4/2013
EP 0 656 210 6/1995
(Continued)

OTHER PUBLICATIONS

Cancer and Metastasis Reviews (1998), 17(1), 91-106.*
(Continued)

*Primary Examiner* — Shawquia Jackson
(74) *Attorney, Agent, or Firm* — Klarquist Sparkman, LLP

(57) ABSTRACT

A compound, or a pharmaceutically acceptable salt thereof, having a structure of:

Formula A

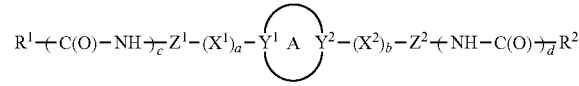

wherein A is a ring;
Y$^1$ and Y$^2$ are each independently N or C with the proper valency;
X$^1$ and X$^2$ are each independently —NH—, —O—, —CH$_2$—O—, —NH—CH$_2$—, or —N(CH$_3$)—CH$_2$—, provided that when at least one of X$^1$ and X$^2$ is —CH$_2$—O—, —NH—CH$_2$—, or —N(CH$_3$)—CH$_2$— then the —CH$_2$— is directly connected to A;
a and b are each independently 0 or 1;
c and d are each independently 0 or 1;
Z$^1$ and Z$^2$ are each independently a heterocyclic; and
R$^1$ and R$^2$ are each independently optionally substituted alkyl, optionally substituted aralkyl, optionally substituted cycloalkyl, amino, optionally substituted heteroaralkyl, optionally substituted alkylalkoxy, optionally substituted alkylaryloxy, optionally substituted aryl, optionally substituted heteroaryl, or optionally substituted heterocycloalkyl;
provided that if Y$^1$ and Y$^2$ are each C, then a is 1 and b is 1;
provided that if Y$^1$ and Y$^2$ are each N, then a is 0 and b is 0;
provided that if Y$^1$ is N and Y$^2$ is C, then a=0 and b=1;
provided that if Y$^1$ is C and Y$^2$ is N, then a=1 and b=0;
provided that if c=0 and d=0, then R$^1$ and R$^2$ are both amino;
provided that if c is 1 and d is 1, then both R$^1$ and R$^2$ are not amino;
provided that if c is 0 and d is 1, then R$^1$ is amino and R$^2$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; and
provided that if c is 1 and d is 0, then R$^2$ is amino and R$^1$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl.

17 Claims, 19 Drawing Sheets

(51) Int. Cl.
      *C07D 417/12*       (2006.01)
      *C07D 417/14*       (2006.01)
      *C07D 285/135*     (2006.01)
      *A61K 31/4535*     (2006.01)

(52) U.S. Cl.
      CPC ......... *C07D 401/14* (2013.01); *C07D 417/12* (2013.01); *C07D 417/14* (2013.01)

(56) References Cited

FOREIGN PATENT DOCUMENTS

| | | |
|---|---|---|
| EP | 2 518 069 | 10/2012 |
| WO | WO 2013/078123 | 5/2013 |
| WO | WO 2014/079136 | 5/2014 |
| WO | WO 2014/089048 | 6/2014 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
International Search Report and Written Opinion issued for International Application No. PCT/US2015/053514 dated Jan. 21, 2016.

* cited by examiner

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00001 | 1 | 284.4 | C8H12N8S2 | >5 | nd | |
| | UPGL00002 | 2 | 520.6 | C24H24N8O2S2 | 3.07 | >3 | |
| | UPGL00003 | 3 | 284.4 | C8H12N8S2 | >5 | nd | |
| | UPGL00018 | 4 | 299.4 | C9H13N7OS2 | >5 | nd | |

FIG. 1A

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| (structure) | UPGL00019 | 5 | 535.6 | C25H25N7O3S2 | 0.031 | 0.14 | 78% |
| (structure) | UPGL00020 | 6 | 383.4 | C13H17N7O3S2 | 1.05 | >3 | |
| (structure) | UPGL00017 | 7 | 298.4 | C9H14N8S2 | >5 | nd | |

FIG. 1B

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| 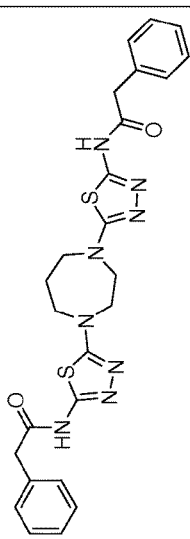 | UPGL00016 | 8 | 534.7 | C25H26N8O2S2 | >5 | nd | |
| 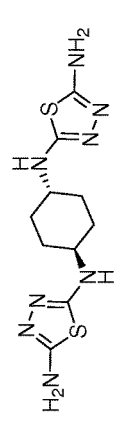 | UPGL00021 | 9 | 312.4 | C10H16N8S2 | >5 | nd | |
| 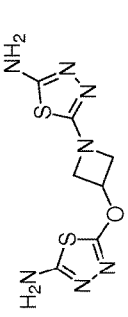 | UPGL00022 | 10 | 271.3 | C7H9N7OS2 | >5 | nd | |
FIG. 1C

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00023 | 11 | 507.6 | C23H21N7O3S2 | 0.058 | >3 | |
| | UPGL00024 | 12 | 355.4 | C11H13N7O3S2 | >5 | nd | |
| | UPGL00025 | 13 | 521.6 | C24H23N7O3S2 | >5 | nd | |
| | UPGL00031 | 14 | 417.5 | C17H19N7O2S2 | 0.203 | 0.97 | |

FIG. 1D

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00050 | 15 | 388.5 | C15H16N8OS2 | 0.227 | >3 | |
| | UPGL00046 | 16 | 537.6 | C23H23N9O3S2 | 0.048 | 0.51 | |
| | UPGL00030 | 17 | 463.6 | C19H25N7O3S2 | 0.157 | 0.63 | |

FIG. 1E

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00041 | 18 | 521.6 | C31H31N5O3 | >5 | nd | |
| | UPGL00043 | 19 | 521.6 | C31H31N5O3 | >5 | nd | |
| | UPGL00044 | 20 | 521.6 | C31H31N5O3 | >5 | nd | |

FIG. 1F

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00045 | 21 | 523.6 | C29H29N7O3 | 0.098 | 2.2 | |
| | UPGL00004 | 22 | 534.7 | C25H26N8O2S2 | 0.029 | 0.07 | 100% |
| | UPGL00011 | 23 | 520.6 | C24H24N8O2S2 | 0.027 | 1.57 | |

FIG. 1G

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| 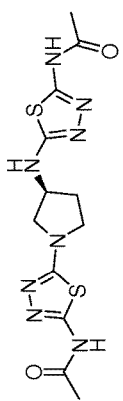 | UPGL00012 | 24 | 368.4 | C12H16N8O2S2 | 7.7 | >3 | |
| 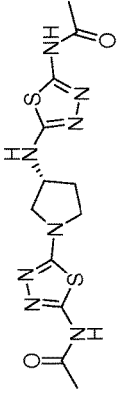 | UPGL00013 | 25 | 368.4 | C12H16N8O2S2 | 0.72 | >3 | |
| 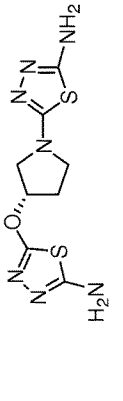 | UPGL00014 | 26 | 285.4 | C8H11N7OS2 | >5 | nd | |
FIG. 1H

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00026 | 27 | 285.4 | C8H11N7OS2 | >5 | nd | |
| | UPGL00027 | 28 | 521.6 | C24H23N7O3S2 | 0.034 | 0.42 | 76% |
| | UPGL00028 | 29 | 535.6 | C25H25N7O3S2 | 0.486 | >3 | |

FIG. 1I

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00029 | 30 | 403.5 | C16H17N7O2S2 | 1.4 | nd | |
| | UPGL00032 | 31 | 299.4 | C9H13N7OS2 | >5 | nd | |
| | UPGL00033 | 32 | 535.6 | C25H25N7O3S2 | 0.03 | 0.23 | |

FIG. 1J

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00036 | 33 | 299.4 | C9H13N7OS2 | nd | nd | |
| | UPGL00037 | 34 | 535.6 | C25H25N7O3S2 | 0.791 | >3 | |
| | n/a | 35 | 298.4 | C9H14N8S2 | nd | nd | |

FIG. 1K

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
|  | UPGL00010 | 36 | 534.7 | C25H26N8O2S2 | 0.054 | 0.32 | 100% |
| 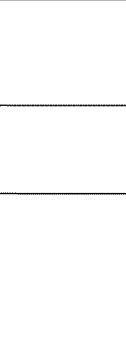 | n/a | 37 | 411.5 | C19H21N7O2S | nd | nd | |
| 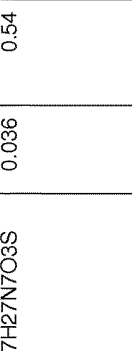 | UPGL00057 | 38 | 529.6 | C27H27N7O3S | 0.036 | 0.54 | |
FIG. 1L

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| (structure) | n/a | 39 | 495.5 | C20H20F3N7O3S | nd | nd | |
| (structure) | UPGL00056 | 40 | 614.6 | C27H25F3N8O4S | 0.084 | 0.35 | |
| (structure) | UPGL00035 | 41 | 403.5 | C16H17N7O2S2 | >5 | nd | |

FIG. 1M

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | n/a | 42 | 313.4 | C10H15N7OS2 | nd | nd | |
| | UPGL00034 | 43 | 549.7 | C26H27N7O3S2 | 0.194 | >3 | |
| | UPGL00006 | 44 | 284.4 | C8H12N8S2 | >5 | nd | |

FIG. 1N

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00005 | 45 | 298.4 | C9H14N8S2 | >5 | nd | |
| | UPGL00009 | 46 | 520.6 | C24H24N8O2S2 | 0.073 | 1.2 | |
| | UPGL00015 | 47 | 521.6 | C24H23N7O3S2 | 0.042 | 0.68 | |

FIG. 10

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| 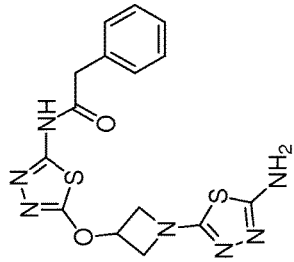 | UPGL00038 | 48 | 389.5 | C15H15N7O2S2 | 0.572 | >3 | |
| 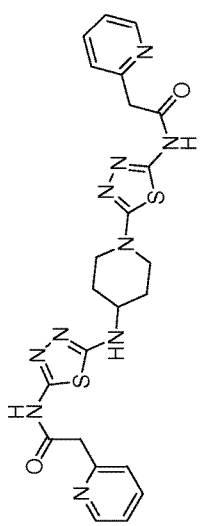 | UPGL00060 | 49 | 536.6 | C23H24N10O2S2 | 0.044 | 0.32 | |
FIG. 1P

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| 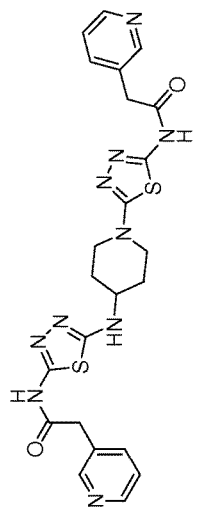 | UPGL00061 | 50 | 536.6 | C23H24N10O2S2 | 0.033 | 2,102 | |
| 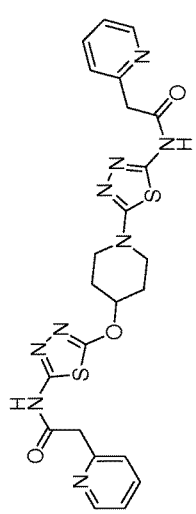 | UPGL00063 | 51 | 537.6 | C23H23N9O3S2 | 0.031 | 0.1 | |
FIG. 1Q

| Structure CMDRW | Compound ID | Example # | MW | EF | GAC IC50 (mM) | Cell IC50 (uM) | HLM stability % of Parent remaining after 30 min incubation |
|---|---|---|---|---|---|---|---|
| | UPGL00062 | 52 | 536.6 | C23H24N10O2S2 | 0.049 | >3,000 | |
| | UPGL00065 | 53 | 416.5 | C17H20N8OS2 | nd | nd | |
| | UPGL00064 | 54 | 498.6 | C22H26N8O2S2 | 0.03 | 0.09 | |

FIG. 1R

| Benchmark compounds | | | | | | | |
|---|---|---|---|---|---|---|---|
| | BPTES | n/a | 524.7 | C24H24N6O2S3 | 0.37 | 2.61 | 53% |
| | CB-839 | n/a | 571.6 | C26H24F3N7O3S | 0.182 | 0.033 | 27% |

FIG. 2

GLUTAMINASE INHIBITORS

CROSS REFERENCE TO RELATED APPLICATIONS

This application is the U.S. National Stage of International Application No. PCT/US2015/053514, filed Oct. 1, 2015, which was published in English under PCT Article 21(2), which in turn claims the benefit of U.S. Provisional Application No. 62/059,707, filed Oct. 3, 2014. The provisional application is incorporated herein in its entirety.

BACKGROUND

Glutaminase is a key player in the altered metabolic pathways of tumor cells. The high glutamine requirements and uptake of cancer cells has been known for decades. For instance, in 1955, Eagle, in his paper "Nutrition needs of mammalian cultured cells" reported that glutamine, a non-essential amino acid, is quite essential for the growth of tumor cells in culture media. Since that report, research in tumor cell metabolism has revealed that high glutamine utilization and dependence, a property termed "glutamine addiction", is a key attribute for multiple tumor cell lines.

There are two glutaminase isoforms namely, the kidney isoform (KGA or GLS1) and the liver isoform (LGA or GLS2). The evidence accumulated so far suggests that KGA and particularly its splice variant GAC are targets of interest for cancer therapy. KGA/GAC upregulation is present in multiple cancer cell lines, correlates with increased proliferative rates, and it is linked to the dysregulation of a number of pathways, including the dysregulation/amplification of the Myc oncogene. Inhibition of KGA/GAC through antisense, siRNA and small molecule inhibitors leads to reduction in tumor cell proliferation as well as tumor size reduction in mice.

SUMMARY

Disclosed herein is a compound, or a pharmaceutically acceptable salt thereof, having a structure of:

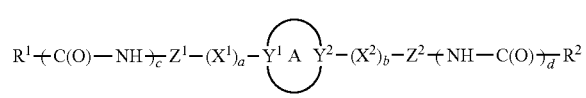

Formula A wherein A is a ring;

$Y^1$ and $Y^2$ are each independently N or C with the proper valency;

$X^1$ and $X^2$ are each independently —NH—, —O—, —CH$_2$—O—, —NH—CH$_2$—, or —N(CH$_3$)—CH$_2$—, provided that when at least one of $X^1$ and $X^2$ is —CH$_2$—O—, —NH—CH$_2$—, or —N(CH$_3$)—CH$_2$— then the —CH$_2$— is directly connected to A;

a and b are each independently 0 or 1;

c and d are each independently 0 or 1;

$Z^1$ and $Z^2$ are each independently a heterocyclic; and $R^1$ and $R^2$ are each independently optionally substituted alkyl, optionally substituted aralkyl, optionally substituted cycloalkyl, amino, optionally substituted heteroaralkyl, optionally substituted alkylalkoxy, optionally substituted alkylaryloxy, optionally substituted aryl, optionally substituted heteroaryl, or optionally substituted heterocycloalkyl;

provided that if $Y^1$ and $Y^2$ are each C, then a is 1 and b is 1;

provided that if $Y^1$ and $Y^2$ are each N, then a is 0 and b is 0 provided that if $Y^1$ is N and $Y^2$ is C, then a=0 and b=1 provided that if $Y^1$ is C and $Y^2$ is N, then a=1 and b=0 provided that if c=0 and d=0, then $R^1$ and $R^2$ are both amino;

provided that if c is 1 and d is 1, then both $R^1$ and $R^2$ are not amino;

provided that if c is 0 and d is 1, then $R^1$ is amino and $R^2$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; and provided that if c is 1 and d is 0, then $R^2$ is amino and $R^1$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl.

Also disclosed herein is a method for treating cancer, ischemic brain injury, a neurological disorder, an immunological disorder, graft vs host disease, inflammatory bowel disease, Crohn's disease, or arthritis in a subject, comprising administering to the subject in need thereof a therapeutically effective amount of at least one compound disclosed herein.

The foregoing will become more apparent from the following detailed description, which proceeds with reference to the accompanying figures.

BRIEF DESCRIPTION OF THE DRAWINGS

FIGS. 1A-1R is a table showing certain compounds and assay results.

FIG. 2 is a table showing assay results for prior art compounds.

DETAILED DESCRIPTION

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl.

"Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl.

"Lower acyloxy" groups contain one to six carbon atoms.

"Administration" as used herein is inclusive of administration by another person to the subject or self-administration by the subject.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, heteroaryl, aralkyl, heteroaralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent. Examples of substituents include, but are not limited to, halogen, cycloalkyl, alkoxy, amino, hydroxyl, aryl, heteroaryl, heterocycloalkyl, alkenyl, carboxyl, etc. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl ($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g., —$CH_2$—$NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, heteroaryl, heteroaralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted.

"Aryloxy" or "heteroaryloxy" refers to a group of the formula —OAr, wherein Ar is an aryl group or a heteroaryl group, respectively.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

The term "carboxylate" or "carboxyl" refers to the group —COO⁻ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like, and may optionally be substituted or unsubstituted. The term "heterocycloalkyl group" is a cycloalkyl group as defined above where at least one of the carbon atoms of the ring is replaced by a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The terms "halogenated alkyl" or "haloalkyl group" refer to an alkyl group with one or more hydrogen atoms present on these groups substituted with a halogen (F, Cl, Br, I).

The term "heteroaralkyl" refers to an alkyl group wherein a heteroaryl group is substituted for a hydrogen in the said alkyl group.

A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Heterocyclic" refers to a closed-ring compound, or radical thereof as a substituent bonded to another group, particularly other organic groups, where at least one atom in the ring structure is other than carbon, and typically is oxygen, sulfur and/or nitrogen.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"Isomer" refers to one of two or more molecules having the same number and kind of atoms, but differing in the arrangement or configuration of the atoms. Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, $arC_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. For example, the removal of an ester, such as cleavage of a phosphonate ester under Lewis acidic conditions, mediated by TMS-Br to yield the free phosphonate. Removal of a benzyl group may be affected by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999 or other chemical literature sources. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Compounds

Disclosed herein according to certain embodiments are glutaminase inhibitors, particularly kidney glutaminase (KGA/GAC), that are bisthiadiazoles, bispyridazines or bispyridines and in which the linker between the thiadiazole, pyridine or pyridazine moieties is a heterocyclic ring system or a heteroatom-substituted carbocycle.

Using a heterocyclic ring or a heteroatom-substituted carbocycle system as a linker between the thiadiazole, pyridazine or pyridine groups leads to a fixed three-dimensional orientation of the thiadiazole, pyridazine or pyridine groups and to compounds with greater potency and/or properties than a prior art compound, BPTES which is described in US20020115698. For instance, the IC50 of UPGL00019, one of the compounds disclosed herein, is one order of magnitude better in the GAC enzyme assay when compared directly to BPTES. The IC50 of UPGL00019 is also better than BPTES by 2 orders of magnitude in inhibiting the proliferation of MDA-MB 231 cancer cells in vitro.

Disclosed herein are compounds, or pharmaceutically acceptable salts thereof, having a structure of:

Formula A

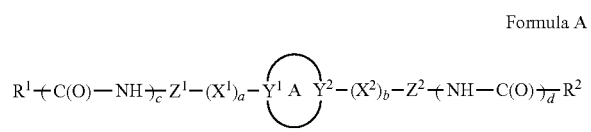

wherein A is a ring;

$Y^1$ and $Y^2$ are each independently N or C with the proper valency;

$X^1$ and $X^2$ are each independently —NH—, —O—, —CH$_2$—O—, —NH—CH$_2$—, or —N(CH$_3$)—CH$_2$—, provided that when at least one of $X^1$ and $X^2$ is —CH$_2$—O—, —NH—CH$_2$—, or —N(CH$_3$)—CH$_2$— then the —CH$_2$— is directly connected to A;

a and b are each independently 0 or 1;

c and d are each independently 0 or 1;

$Z^1$ and $Z^2$ are each independently a heterocyclic; and $R^1$ and $R^2$ are each independently optionally substituted alkyl, optionally substituted aralkyl, optionally substituted cycloalkyl, amino, optionally substituted heteroaralkyl, optionally substituted alkylalkoxy, optionally substituted alkylaryloxy, optionally substituted aryl, optionally substituted heteroaryl, or optionally substituted heterocycloalkyl;

provided that if $Y^1$ and $Y^2$ are each C, then a is 1 and b is 1;

provided that if $Y^1$ and $Y^2$ are each N, then a is 0 and b is 0;

provided that if $Y^1$ is N and $Y^2$ is C, then a=0 and b=1;

provided that if $Y^1$ is C and $Y^2$ is N, then a=1 and b=0;

provided that if c=0 and d=0, then $R^1$ and $R^2$ are both amino;

provided that if c is 1 and d is 1, then both $R^1$ and $R^2$ are not amino;

provided that if c is 0 and d is 1, then $R^1$ is amino and $R^2$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; and provided that if c is 1 and d is 0, then $R^2$ is amino and $R^1$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl.

In certain embodiments, A is N-heterocyclic. For example, A is a 3, 4, 5, 6 or 7 member N-heterocyclic. In certain embodiments, A is a saturated N-heterocyclic. In certain embodiments, $Y^1$ and $Y^2$ are each N; $Y^1$ is N and $Y^2$ is C; or $Y^1$ is C and $Y^2$ is N. Illustrative A groups include:

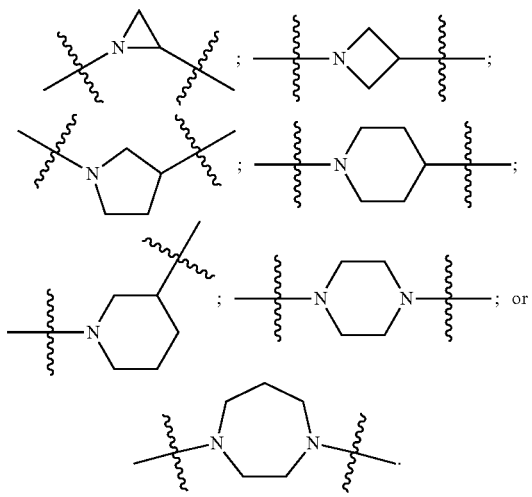

In certain embodiments A is derived from a heteroatom-substituted cycloalkyl. For example a 3, 4, 5, 6, or 7 member cycloalkyl where Y1 and Y2 are C. Illustrative groups include:

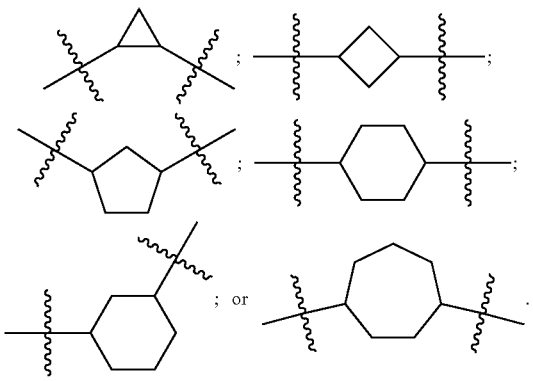

In certain embodiments, at least one of a or b is 1. In certain embodiments, a and b are both 1. In certain embodiments, a and b are both 0. In certain embodiments, at least one of $X^1$ or $X^2$ is —NH—. In certain embodiments, a and b are both 1 and $X^1$ and $X^2$ are —NH— or —O—. In certain embodiments, a and b are both 1 and $X^1$ and $X^2$ are each —NH—. In certain embodiments, at least one of $X^1$ or $X^2$ is —O—. In certain embodiments, at least one of $X^1$ is —CH$_2$—O— or $X^2$ is —CH$_2$—O—. In certain embodiments, a is 1, b is 0, and $X^1$ is —NH—, —O—, or —CH$_2$—O—. In certain embodiments, a is 0, b is 1, and $X^2$ is —NH—, —O—, or —CH$_2$—O—. In certain embodiments, a is 1, b is 0, $X^1$ is —NH—, —O—, or —CH$_2$—O—, and $Y^2$ is N. In certain embodiments, a is 0, b is 1, $X^2$ is —NH—, —O—, or —CH$_2$—O—, and $Y^1$ is N.

In certain embodiments, $Z^1$ and $Z^2$ are each the same. In certain embodiments, $Z^1$ and $Z^2$ are each a N-heterocyclic. In certain embodiments, $Z^1$ and $Z^2$ are each independently selected from thiadiazole (particularly 1,3,4-thiadiazole), pyridazine, or pyridine. Illustrative $Z^1$ and $Z^2$ groups include:

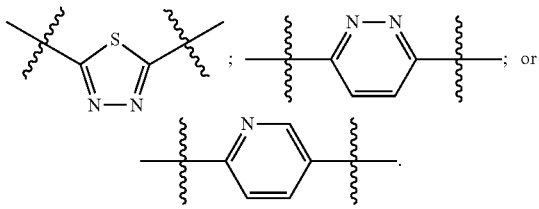

In certain embodiments, c and d are each 1. In certain embodiments, c is 1 and d is 0. In certain embodiments, c is 0 and d is 1. In certain embodiments, c and d are each 0. In certain embodiments, c and d are each 1, and $R^1$ and $R^2$ are optionally-substituted benzyl, alkyl (particularly methyl), pyridinylmethyl, or cyclopropylmethyl. In certain embodiments, c and d are each 0, and $R^1$ and $R^2$ are each —NH$_2$. In certain embodiments, c is 1, $R^1$ is optionally-substituted benzyl, alkyl (particularly methyl), pyridinylmethyl, or cyclopropylmethyl, d is 0, and $R^2$ is —NH$_2$. In certain embodiments, c is 0, $R^2$ is —NH$_2$, d is 1, and $R^2$ is optionally-substituted benzyl, alkyl (particularly methyl), pyridinylmethyl, or cyclopropylmethyl.

In certain embodiments, at least one of $R^1$ and $R^2$ is benzyl or optionally-substituted benzyl, —NH$_2$, methyl, pyridinylmethyl, cyclopropylmethyl, or amino. In certain embodiments, $R^1$ and $R^2$ are each the same. In certain embodiments $R^1$ and $R^2$ are not the same.

In certain embodiments, the A group is selected from:

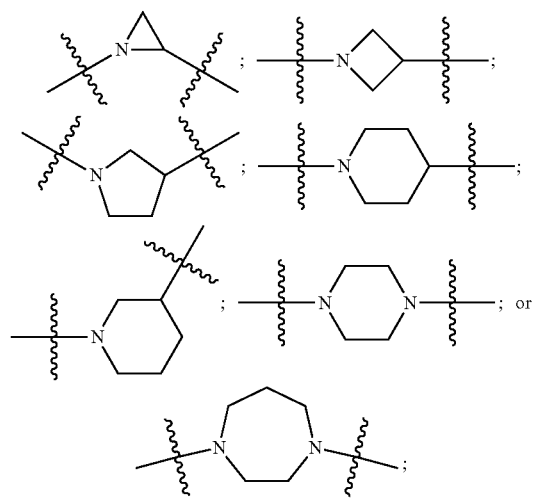

and the $Z^1$ and $Z^2$ groups are each independently selected

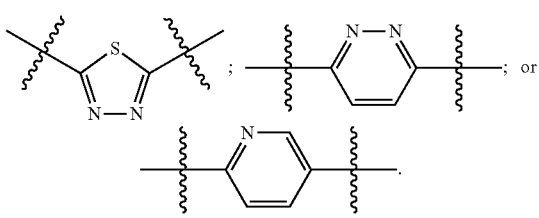

In certain embodiments, the A group is selected from:

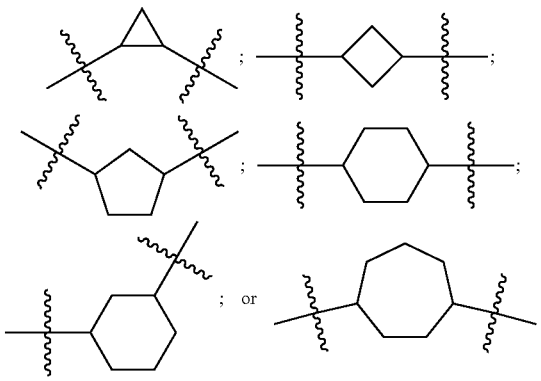

and the $Z^1$ and $Z^2$ groups are each independently selected from

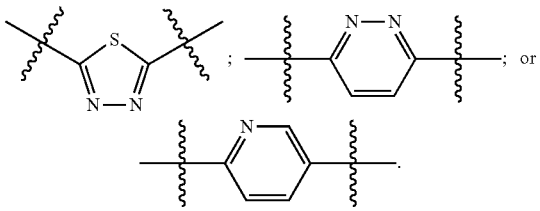

In certain embodiments, $Z^1$ and $Z^2$ groups are each

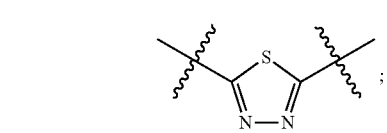 [SMILES: *c1nnc(*)s1]

c and d are each 1; and at least one of $R^1$ and $R^2$ is benzyl or substituted benzyl.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Abbreviations as used herein:
THF is tetrahydrofuran,
DMF is N,N-dimethylformamide,
DMA is N,N-dimethylacetamide,
NMP is N-methylpyrolidone
DMSO is dimethylsulfoxide,
DCM is dichloromethane,
DME is dimethoxyethane,
MeOH is methanol,
EtOH is ethanol,
TFA is 1,1,1-trifluoroacetatic acid,
HOBT is 1-hydroxybenzotriazole,
PyBroP is bromotripyrrolidinophosphonium hexafluorophosphate, EDCI is 1-[3-(dimethylamino)propyl]-3-ethylcarbodiimide hydrochloride,
HATU is 1-[Bis(dimethylamino)methylene]-1H-1,2,3-triazolo[4,5-b]pyridinium 3-oxid hexafluorophosphate
DCC is N,N'-dicyclohexylcarbodiimide
Boc is tert-butyloxy carbonyl
Cbz is carboxybenzyl
DIPEA is diisopropylethylamine,
Boc is tert-butyloxycarbonyl,
NBS is N-bromosuccinimde,
DMAP is N,N-dimethylamino-pyridine,
DEAD is diethyl azodicarboxylate,
Brine is saturated aqueous sodium chloride solution,
TLC is thin layer chromatography,
HR-MS is high resolution mass spectrometry,
NMR is nuclear magnetic resonance spectroscopy
LC-MS is liquid chromatographic mass spectrometry,
RT is room or ambient temperature.
ESI is electron spray ionization mass spectrometry
Compounds disclosed herein may be prepared by commercially available starting materials and via synthetic techniques and procedures known those skilled in the art. Outlined below are general reaction schemes suitable for preparing such compounds. Further exemplification is found in specific examples listed below.

Compounds of the general structure I and II (scheme 1) where Q is a racemic or chiral 3, 4, 5, 6 or 7 member carbocyclic ring and where Z and Y are both nitrogen at syn or anti orientation or where Z and Y are both nitrogen and where one of which or both said nitrogens is part of heterocyclic chiral or achiral saturated ring system are made as described below.

Scheme 1

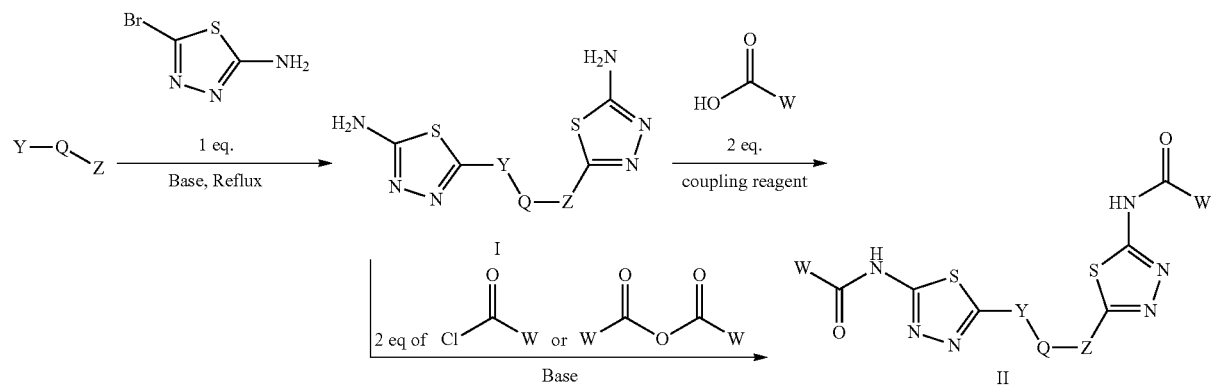

Y = Z = primary or secondary amine nitrogen susbstituent present on a carbocyclic or saturated heterocyclic ring system Overall the synthesis of such compounds involves the aromatic nucleophilic substitution reaction between a desired di-amino containing ring system with two equivalents of commercially available 2-amino 5-bromothidiazole under reflux in EtOH or other suitable solvent and in the presence of triethylamine, $NaHCO_3$ or other suitable base to afford compounds of general structure I. These compounds may then be converted to compounds of the general structure II via treatment with two equivalents of a desirable acid using HATU, EDCI, DCC or other suitable coupling agent or via coupling with 2 eq. of a suitable acyl halide or acid anhydride reagent in the presence of $Et_3N$ or other suitable base under standard conditions known to the persons skilled in the art.

Scheme 2

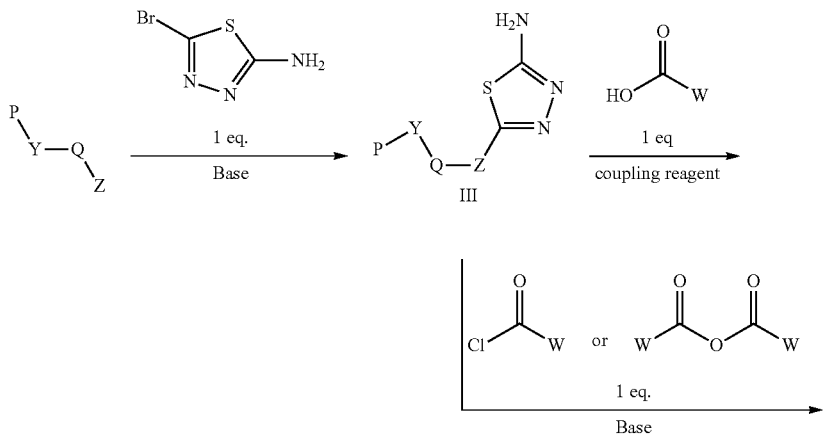

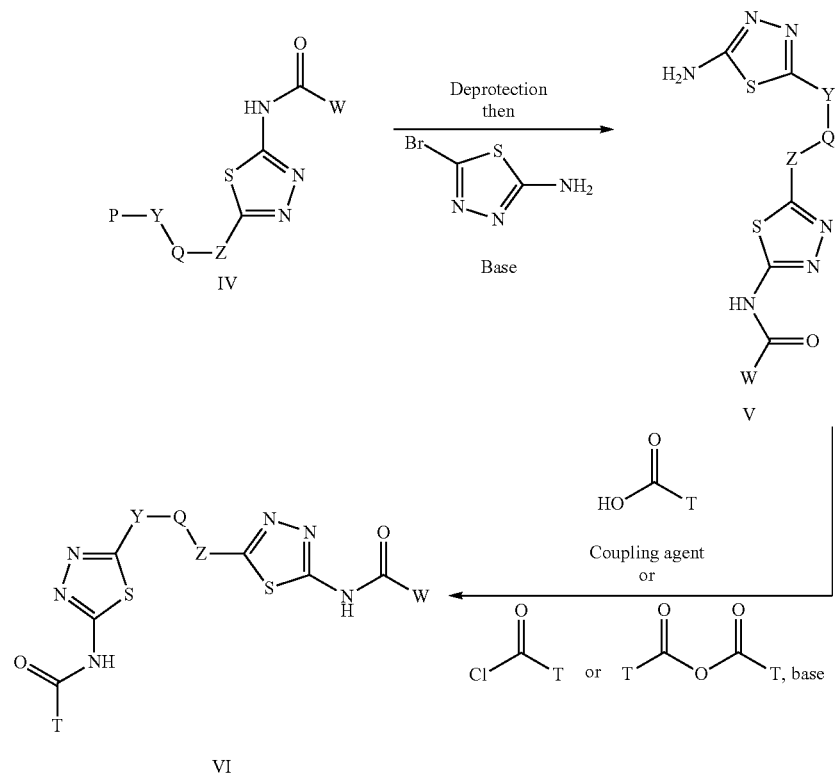

Y = Z = primary or secondary amine nitrogen susbstituent present on a carbocyclic or saturated heterocyclic ring system
P = protecting group Compounds of the general structure V and VI, in which T W, and where Q, Z, and Y in compounds V and VI are as described above may be made in the manner described in scheme 2. Specifically, treatment of a suitably mono-protected diamine ring system of the type P—Y-Q-Z (where Y, Q, Z are as described above and P is protecting group such as Boc, Cbz or other suitable group known to the persons skilled in the art) with 1 equivalent of 2-amino 5-bromothiadiazole under aromatic nucleophilic substitution conditions leads to intermediates of general structure III. Acylation of such intermediates with a desirable acid and a coupling reagent such as HATU, DCC, EDCI or other suitable acylating agents known to the persons skilled in the art leads to compounds of the general structure IV. Deprotection under standard literature conditions followed by coupling as described above with 2-amino 5-bromothiadiazole in the presence of triethylamine, NaHCO$_3$ or other suitable base affords compounds of general structure V. Further treatment of V with a desirable acid and then a coupling agent such as HATU, DCC, EDCI or other suitable coupling agents known to the persons skilled in the art or with a suitable acyl halide or acyl anhydride reagent in the presence of a base leads to desired compounds of general structure VI and in which T≠W.

Scheme 3

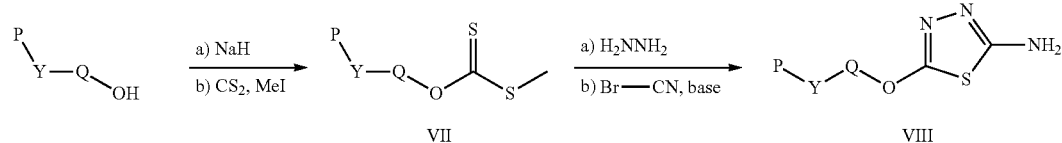

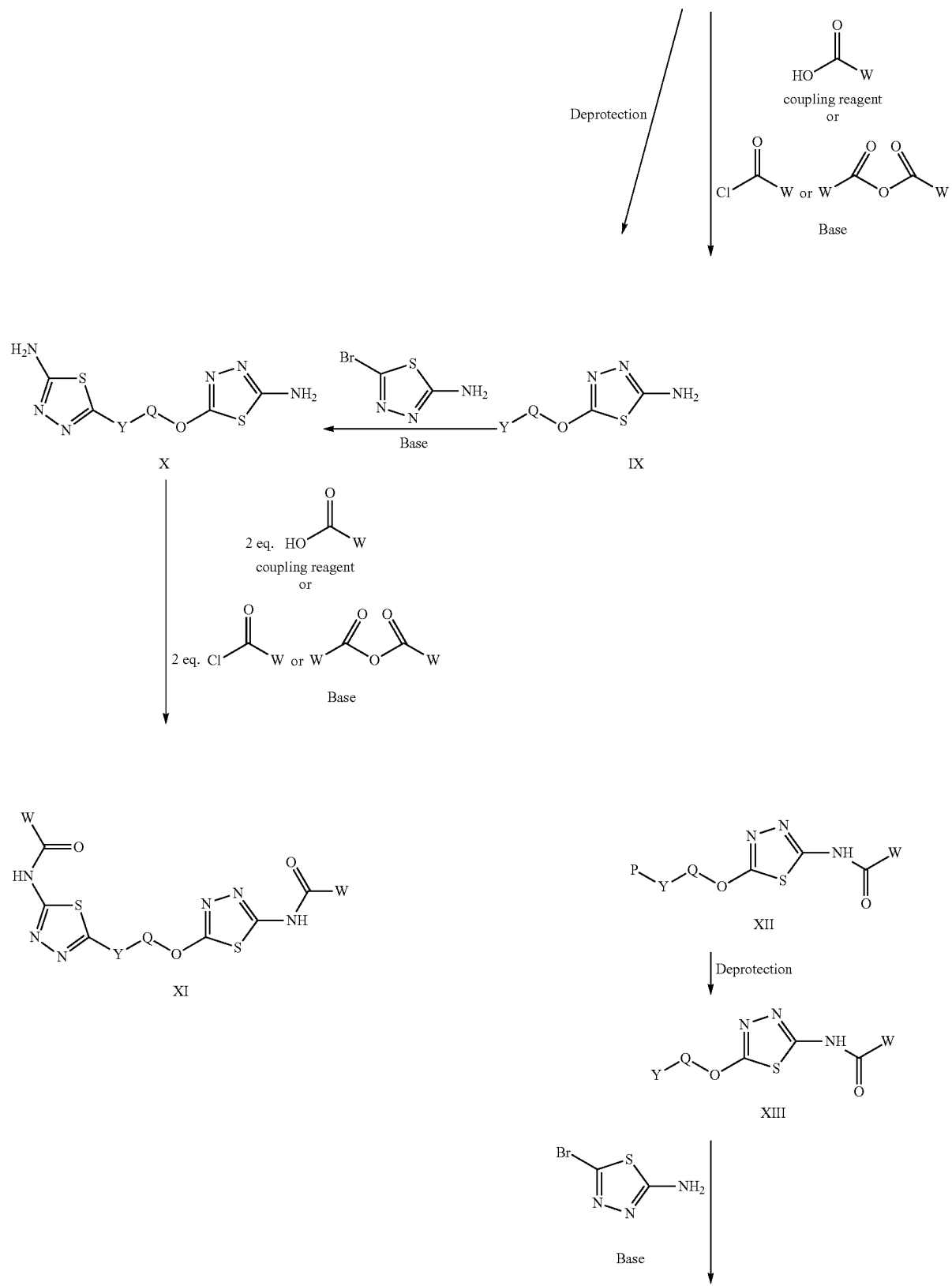

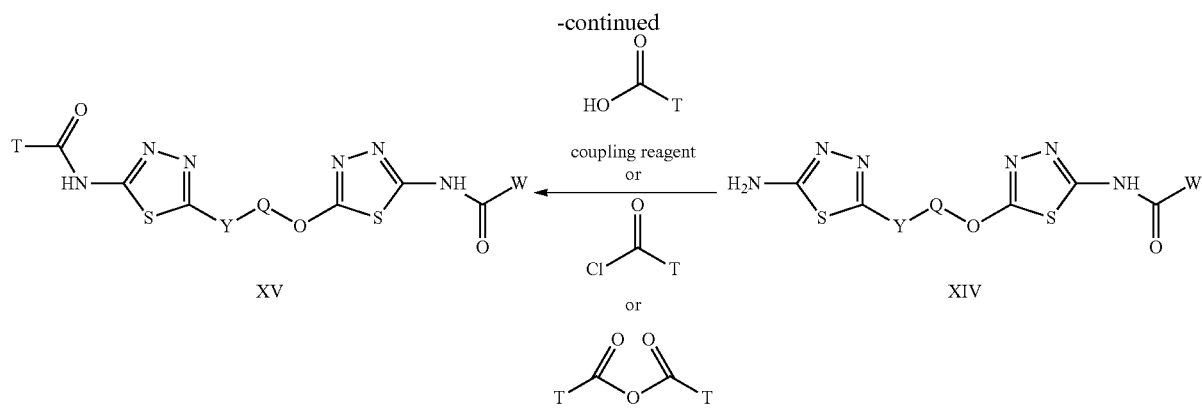

Y = primary or secondary amine nitrogen susbstituent present on a carbocyclic or saturated heterocyclic ring system
P = protecting group(s)

Compounds of general structure X, XI, XIV and XV (scheme 3) where Q is a racemic or chiral 3, 4, 5, 6 or 7 member carbocyclic ring and where Z is nitrogen that it is in anti or syn orientation relative to a hydroxyl group present on the said carbocyclic system, or alternatively where the nitrogen is part of the said ring system as a heteroatom, can be prepared as shown in scheme 3. Specifically, reaction of a desirable and suitably N-protected amino alcohol with NaH, followed by addition with carbon disulfide and MeI under standard Chugaev ester formation conditions affords the corresponding xanthate esters of general structure VII. Further reaction of such compounds with hydrazine affords the corresponding thiocarbonyl hydrazides that upon treatment with cyanogen bromide in the presence of a base such as $Et_3N$, di isopropyl ethyl amine or other suitable base known to the people in the art leads to the formation of the desired thiadiazole derivatives of general structure VIII. Removal of protecting group(s) under standard and appropriate literature conditions leads to the free amine intermediate IX that upon treatment with 2-amino-5-bromothiadiazole under standard aromatic nucleophilic substitution conditions in the presence of triethylamine, $NaHCO_3$ or other suitable base leads to desired bis thiadiazole compounds of the general structure X. Treatment of compounds X with 2 equivalents of acid in the present of a coupling agent such as EDCI, DCC, HATU or other suitable amide forming agent known to the persons skilled in the art, or alternatively, treatment of compounds X in DMF or other suitable solvent with 2 equivalents of a desired acyl chloride or acyl anhydride under standard amide forming conditions leads to desired compounds XI. Compounds of the general structure XIV can be prepared from intermediates of the general structure VIII (scheme 3) by first acylating compounds VIII, using materials and methods already described previously, then deprotecting the aminoalcohol core and then reacting the de-protected analogs with 2-amino-5-bromothiadiazole. Compounds of the general structure XV and in which T≠W may be prepared by acylating compounds of the general structure XIV with a desirable and suitable acyl group donor via procedures and methods already described above and that are known in the literature and to the persons skilled in the art.

Compounds of the general structure XVIII and XIX (scheme 4) where Q is a racemic or chiral 3, 4, 5, 6 or 7 member carbocyclic ring and where Z and Y are both nitrogen at syn or anti orientation or where Z and Y are both nitrogen and where one of which or both said nitrogens is part of heterocyclic chiral or achiral saturated ring system may be prepared from known and/or commercially available intermediates and via literature methods known to those skilled in the art as depicted in scheme 4. For example, treatment of the commercially available 3,6 dichloropyridazine in the presence of $Et_3N$, diisopropyl ethylamine or other suitable base with a desirable diamine of the general structure Y-Q-Z, where Z, Q and Y are as defined above, at elevated temperature and under aromatic nucleophilic substitution conditions affords the desired bis-chloropyridazine of the general structure XVI. From this intermediate compounds of the general structure XVIII may be prepared by reaction of XVI with $H_2N-NH_2$ and then treatment with $H_2$ and Raney Nickel as described in Barlin, G. et al Australian Journal of Chemistry, 42(10), 1759-68; 1989. Alternatively, compounds XVIII may be prepared by direct reaction with $NH_3$ as described in Yu, G. et al WO0056719A1 or via Hartwick-Buchwald palladium mediated amination using $BocNH_2$, $Ph_2C=NH$ or other suitable ammonia equivalent with catalysts and methods known to the persons skilled in the art and then an appropriate deprotection of the intermediate coupling product. Compounds of the general structure XVIII may also be prepared by the reduction of compounds of the general structure XVII with $H_2Pd/C$ or Fe, $NH_4Cl$ or other appropriate reduction method known to the persons skilled in the art. Compounds of the general structure XVII in turn may be prepared via the reaction of diamine Y-Q-Z, where Y, Q and Z are as defined previously, with 3-chloro-6-nitro pyridazine in DMSO or NMP or other suitable solvent and in the presence of $Et_3N$, diisopropylethylamine or other suitable base as described in Shirakami, S. et al WO08084861A1. Finally desired compounds of the general structure XIX may be prepared via the reaction of compounds of the general structure XVIII with 2 equivalents of a suitable acid in the present of a coupling agent such as EDCI, DCC, HATU or other suitable amide forming agent, or alternatively, by treatment with 2 equivalents of a desired acyl halide or acyl anhydride under conditions and methods known in the literature and to the persons skilled in the art and discussed previously.

Scheme 4

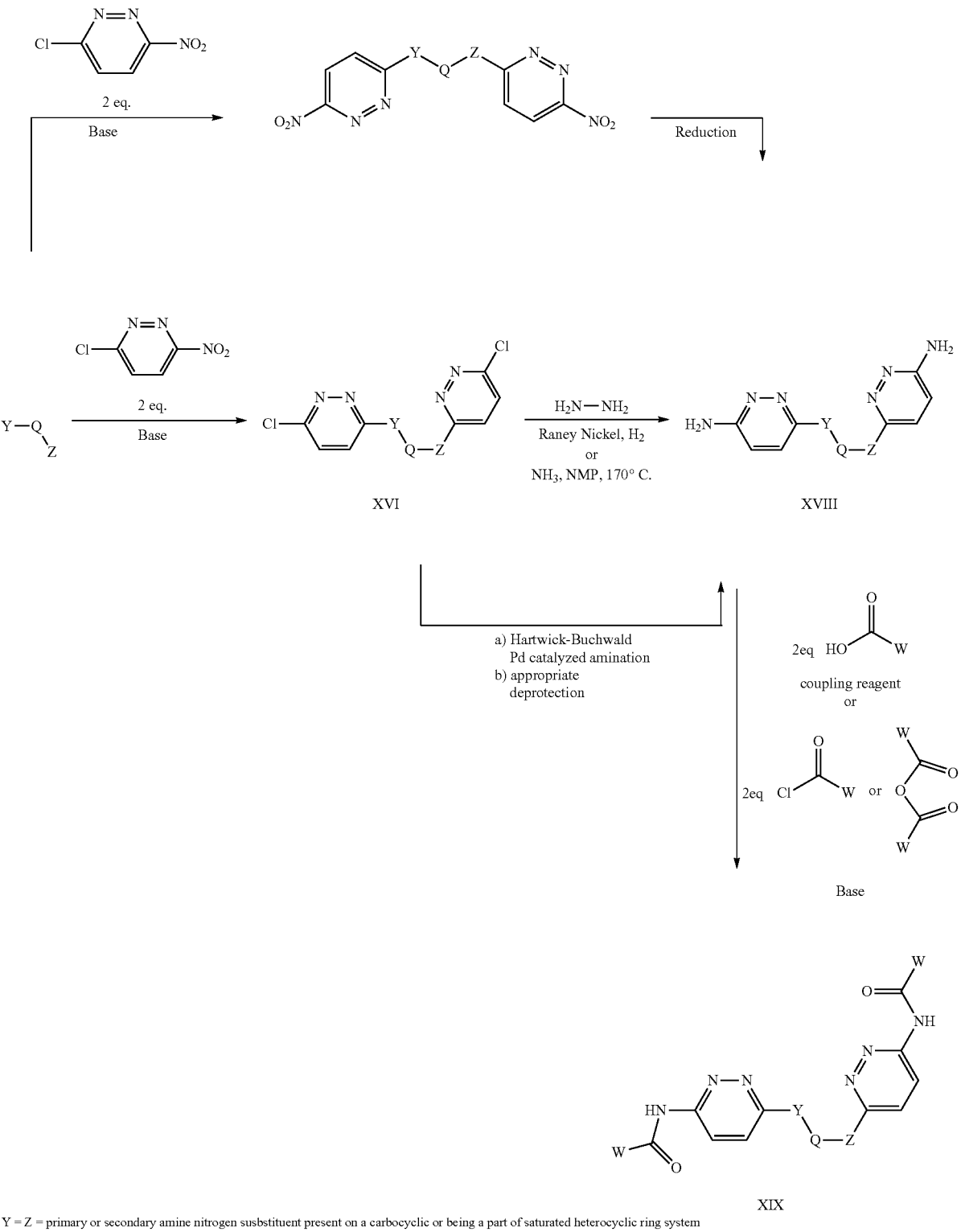

Y = Z = primary or secondary amine nitrogen susbstituent present on a carbocyclic or being a part of saturated heterocyclic ring system Compounds of the general structure XXV and XVI, in which W≠T, and where Y-Q-Z are as defined previously may be prepared from a desirably mono-protected cyclic diamine of the general structure P—Y-Q-Z, where P represents protecting group(s) as described above, as shown in general scheme 5. Materials and methods to carry out the reaction sequences shown in scheme 5 are known in the literature and to the persons skilled in the art and have already discussed above.

Scheme 5

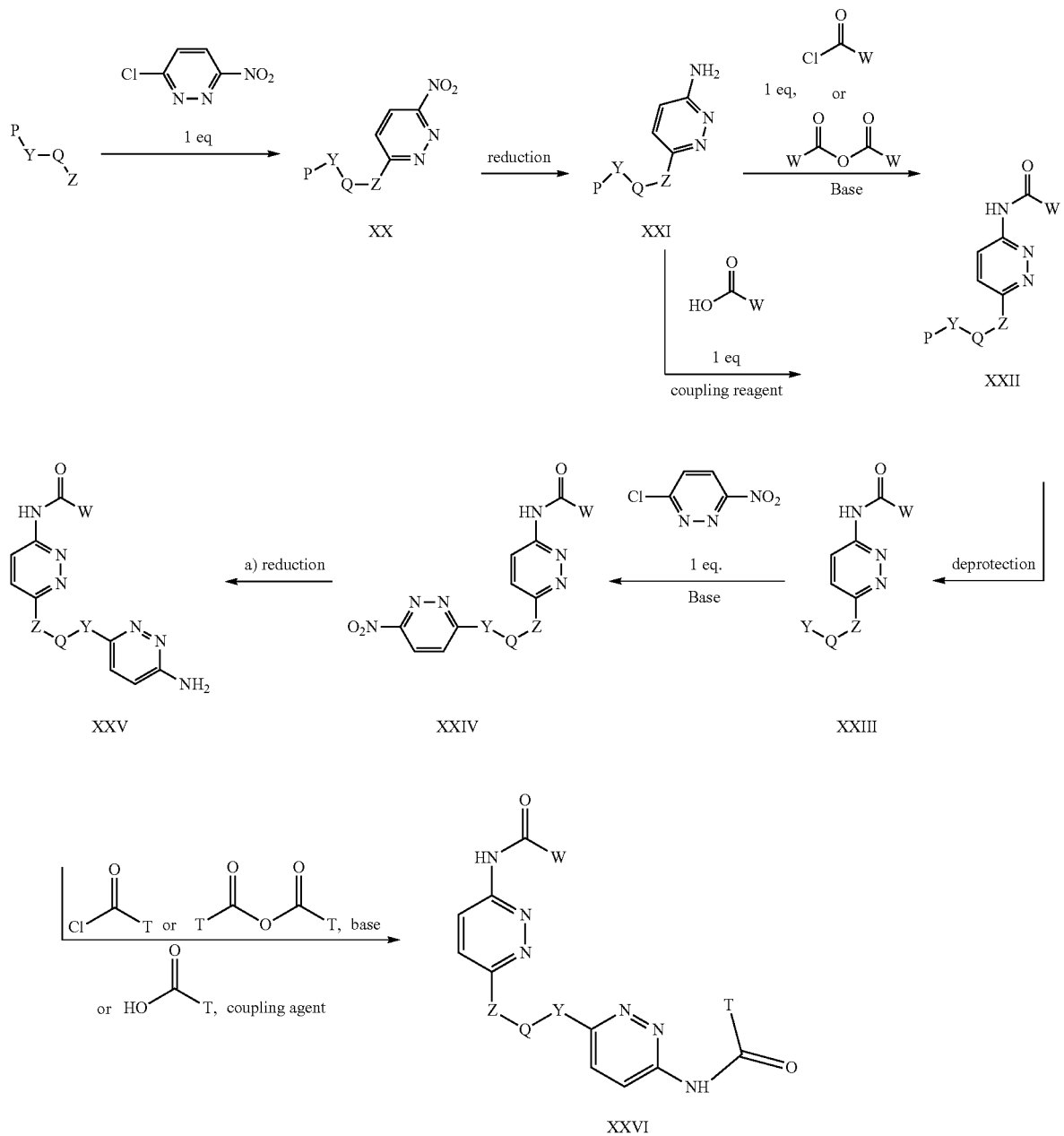

Y = Z = primary or secondary amine nitrogen susbstituent present on a carbocyclic or saturated heterocyclic ring system
P = protecting group Compounds of the general structure XXIX, XXXV, XXXIII and XXXVI, in which T≠W, may be prepared as shown in scheme 6 starting with a desirable amino alcohol of the general structure Y-Q-OH, where Q and Y are as defined previously. Conditions and methods with which the said compounds may be prepared were already described in detail above and are known in the literature and to the persons skilled in the art.

Compounds of the general structure XLI, XLII, XLIV and XLV in which T≠W may be prepared as shown in scheme 7 from a desirable and appropriately N-protected aminoalcohol of the general structure P—Y-Q-OH, where P, Y and Q are as previously described. Conditions and methods with which the said compounds may be prepared were described in more detail above and are known in the literature and to the persons skilled in the art.

Compounds of the general structure XLVII, XLVIII, L and LI, in which T≠W, and where P, Y and Q are as previously described, may be prepared from compounds of the general structure IX and XIII under the synthetic sequence shown in scheme 8 and using methods and conditions already known to the persons skilled in the art. Compounds IX and XIII in turn, may be prepared via the general synthetic scheme 3 using protocols and methods already described and known in the literature and to the persons skilled in the art.

Scheme 6
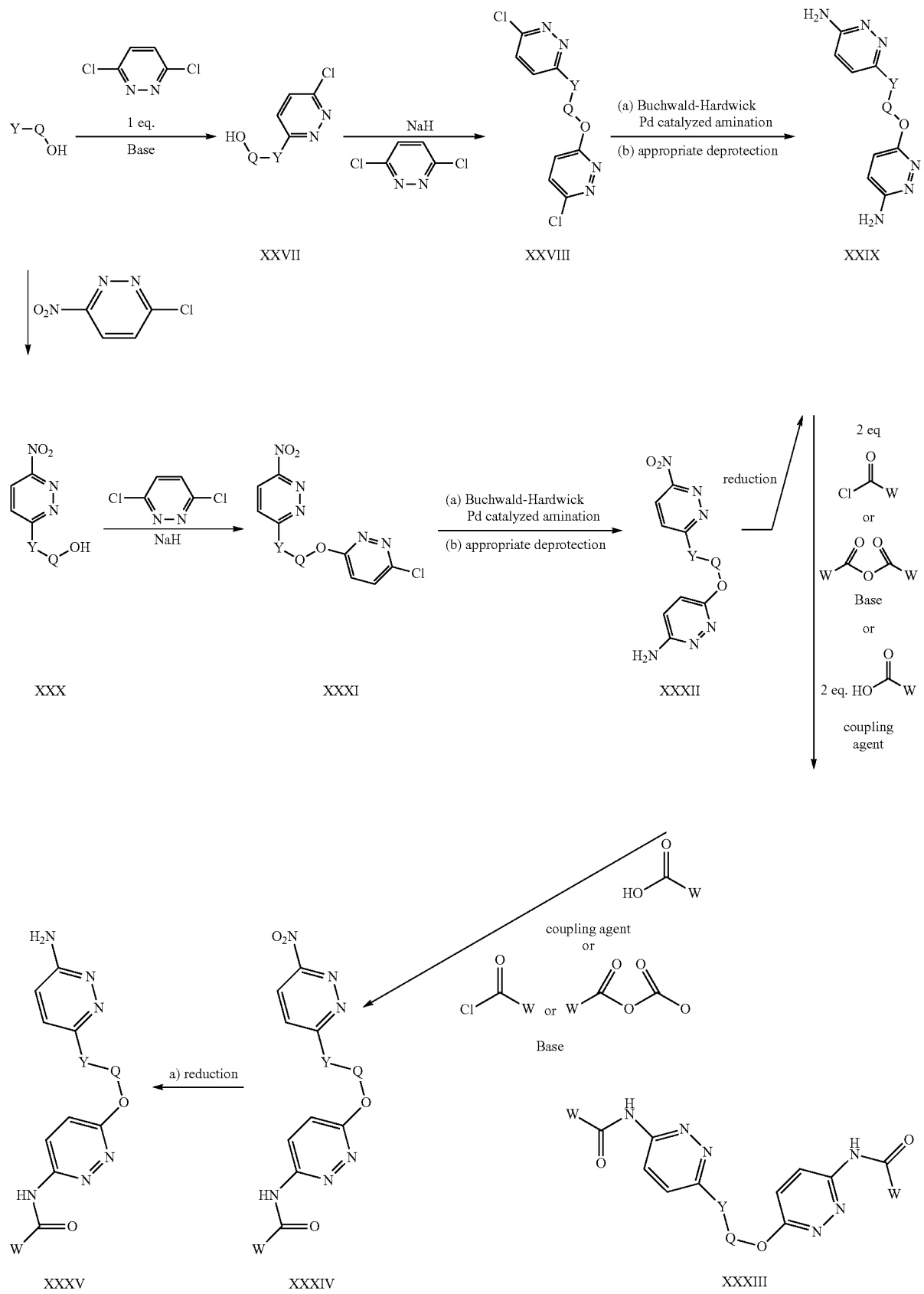

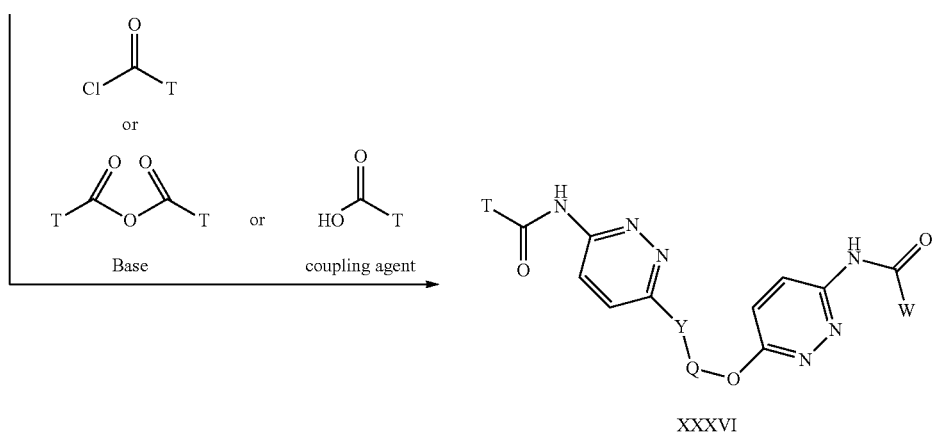
Y = Z = primary or secondary amine nitrogen susbstituent present on a carbocyclic or saturated heterocyclic ring system
Scheme 7
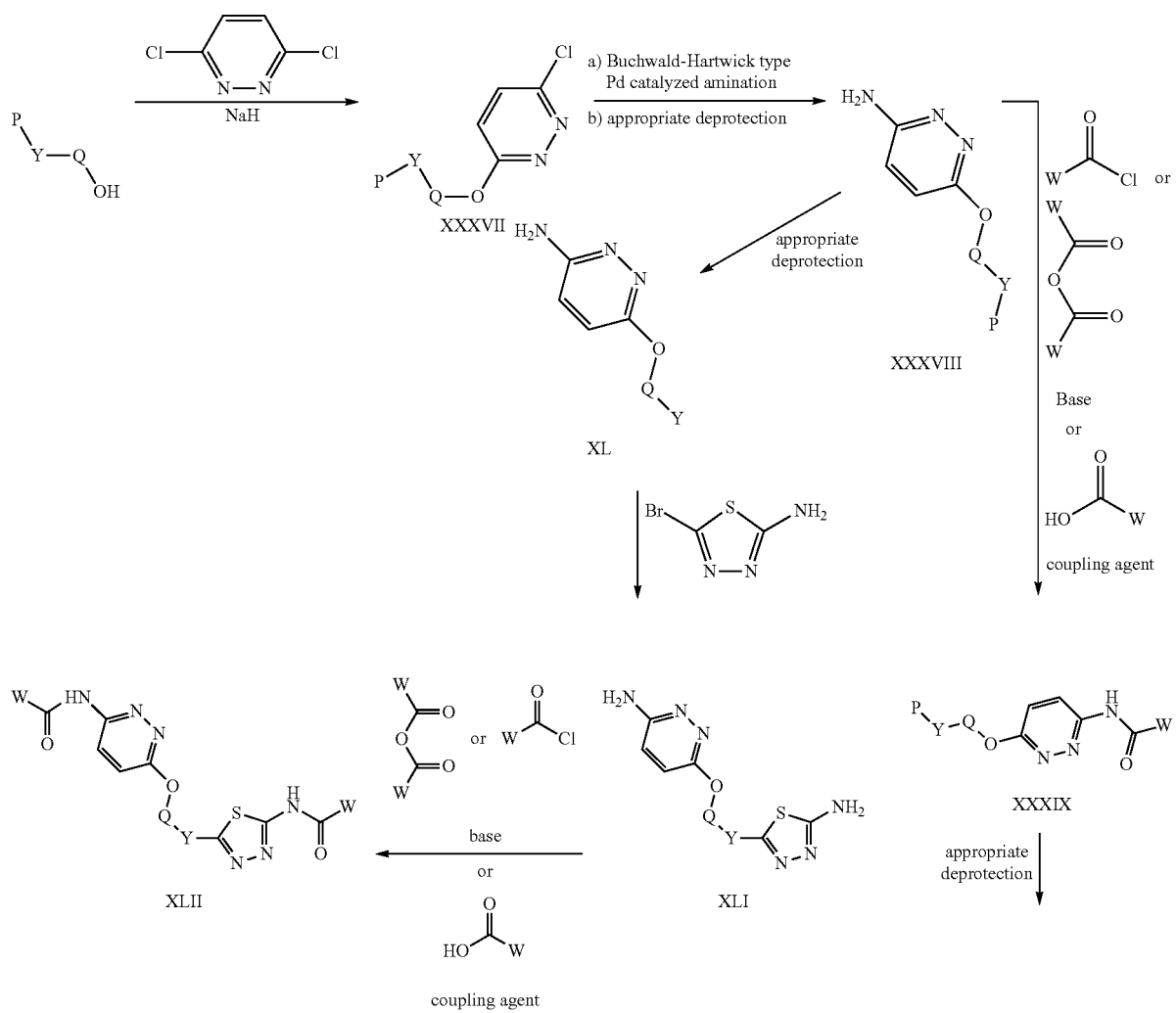

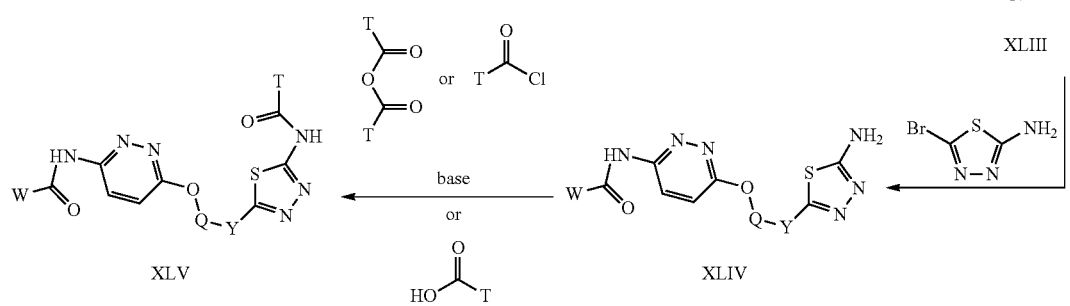

Compounds of the general structure LVI, LVII, LVIII, LIX, LXII, LXIII, LXIV and LXV where Y-Q is a nitrogen containing 3, 4, 5, 6 or 7 membered saturated heterocyclic ring system that also contains a hydroxyl substituent OH, and where said cyclic amino alcohol Y-Q-OH is chiral or achiral, may be prepared as shown in scheme 9. Compounds of the general structure LVI and LVII may be prepared via the reaction of desired amino alcohols Y-Q-OH with commercially available 2-nitro-5-chloropyridine and/or 2-chloro-5-nitropyridine under standard aromatic nucleophilic substitution conditions to afford intermediates LII and LIII. Intermediates LII and LIII may be then converted to desired compounds LVI and LVII after an aromatic nucleophilic substitution with 2-chloro-5-nitro pyridine followed by reduction and acylation using standard procedures and methods known to the persons skilled in the art. Compounds LXIV and LXV may be prepared from intermediates LII and LIII and commercially available 2-nitro 5-hydroxypyridine via a Mitsunobu reaction followed by reduction of the nitro groups and then acylation with a suitable and desirable acyl group donor under procedures and conditions known in the literature and to the persons skilled in the art.

Scheme 8

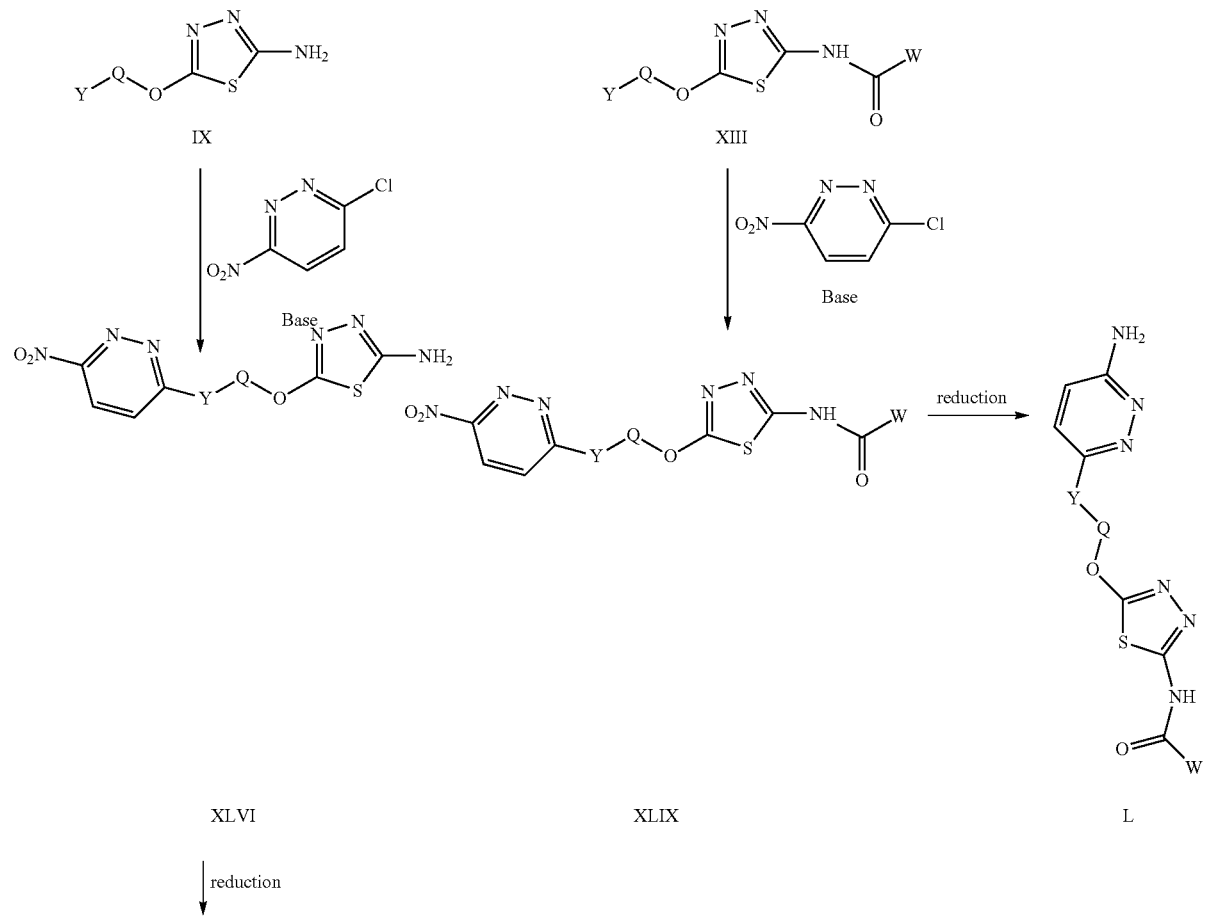

-continued
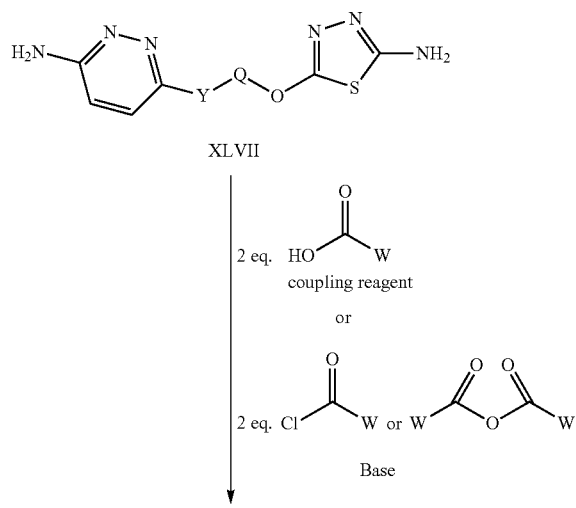
XLVII
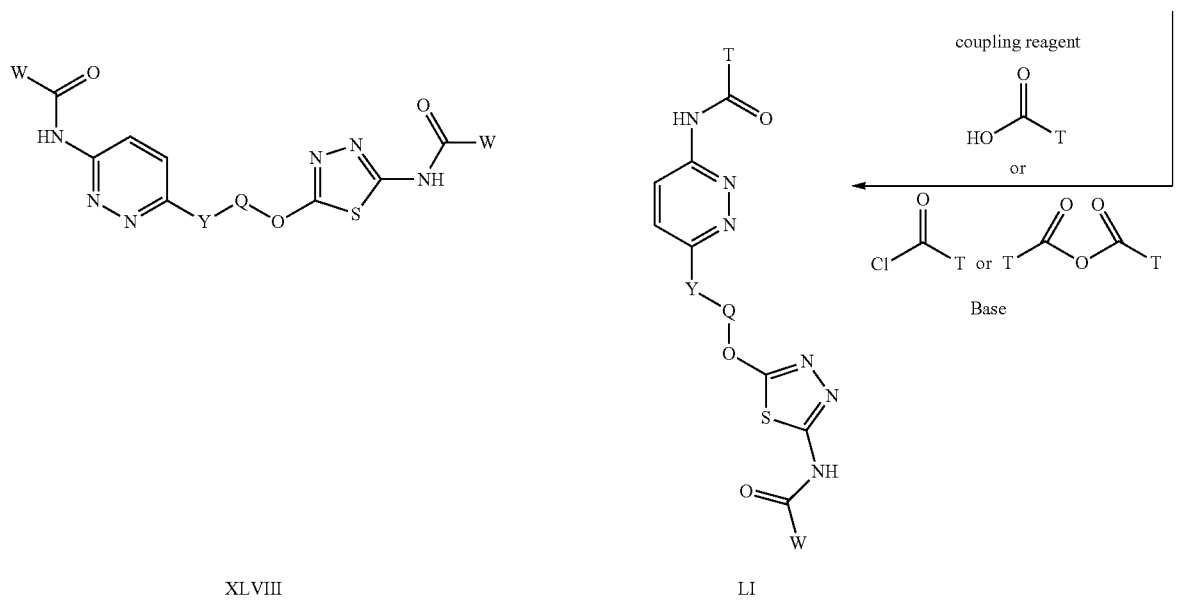
XLVIII
LI
Scheme 9
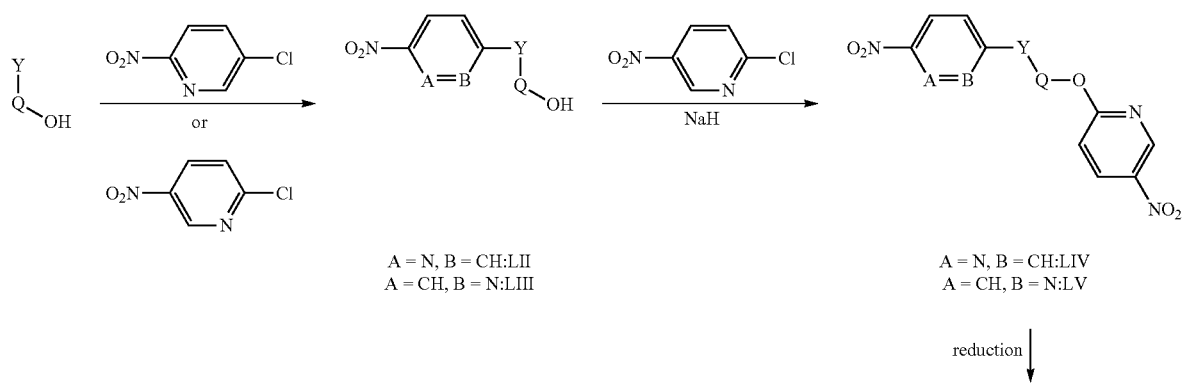
A = N, B = CH:LII
A = CH, B = N:LIII
A = N, B = CH:LIV
A = CH, B = N:LV
reduction ↓

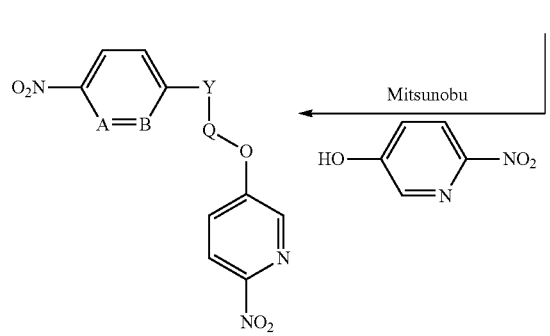

A = N, B = CH:LX
A = CH, B = N:LXI reduction ↓

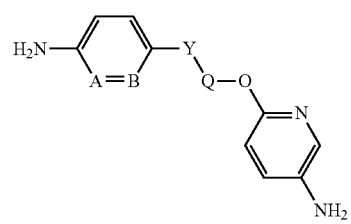

A = N, B = CH:LVI
A = CH, B = N:LVII

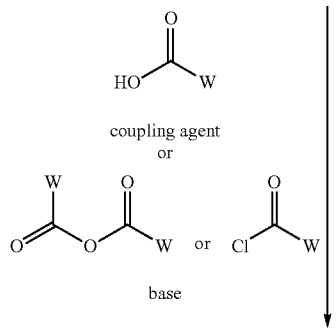

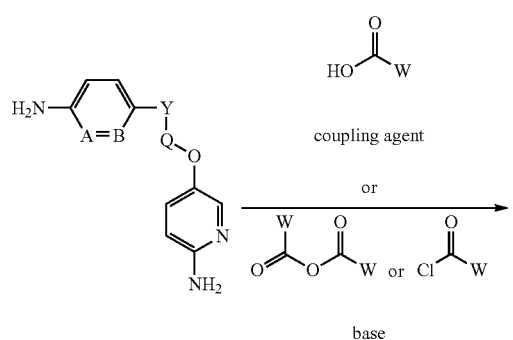

A = N, B = CH:LXII
A = CH, B = N:LXIII

A = N, B = CH:LXIV
A = CH, B = N:LXV

A = N, B = CH:LVIII
A = CH, B = N:LIX

Compositions and Methods of Use

The compounds disclosed herein are useful for treating diseases and conditions associated with the presence of a high level of glutamate and/or upregulation or dysregulation of glutaminase or increased use of glutamine. Examples of such diseases and conditions include, but are not limited to, brain ischemia, neurological disorders such as hepatic encephalopathy, Alzheimer's disease, immunological disorders and diseases associated with proliferation and activation of T-lymphocytes such as graft vs host disease, inflammatory bowel disease, Crohn's disease, arthritis, etc. The compounds disclosed herein are also useful for treating cancer. Illustrative cancers include, but are not limited to, breast cancer, prostate cancer, lymphoma, pancreatic cancer, colorectal cancer, Karposi sarcoma and AIDS related cancers, melanoma, cancer of the cervix, head and neck cancers, brain cancer, cancer of the oral cavity, esophageal cancer, throat cancer, thyroid cancer, haematological cancers, cancer of the stomach, lung cancer, testicular cancer, ovarian cancer, or endometrial cancer. The compounds disclosed herein are also useful for treating liver fibrosis.

In certain embodiments, the compounds disclosed herein are useful for treating glutamine-dependent diseases or conditions.

In certain embodiments, the subject is in need of, or has been recognized as being in need of, treatment with a glutaminase inhibitor. The subject may be selected as being amenable to treatment with a glutaminase inhibitor. In certain embodiments, the compounds disclosed herein are useful for inhibiting glutaminase in a cell by contacting the cell with the compound.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed. The pharmaceutical composition can be formulated in a dosage unit form.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel), Freund's adjuvant, MPL™ (3-O-deacylated monophosphoryl lipid A)-) and IL-12 among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein.

In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional chemotherapeutic agent used to treat immunological and neurological diseases or cancer. Examples of agents that may be co-administered are, but not limited to, methotrexate, capecitabine, imatinib, erlotinib, cisplatin, irinotecan, artemisole, sorafenib, sunitinib, trastuzumab, etc. The compounds disclosed herein may also be co-administered with combination therapies approved and used in the treatment of cancer. Examples of such combination therapies are, but not limited to, ACE (cyclophosphamide, doxorubicine, etoposide), BOMP (bleomycin, vincristine, cisplatin, mitomycin), CHOP (cyclophosphamide, doxorubicine, vincristine, predisone), etc.

The compounds disclosed herein may be co-administered with non-chemotherapeutic treatment methods. Examples of such methods include, but are not limited to, surgery, thermoablation, radiation, etc. or a combination of those methods.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

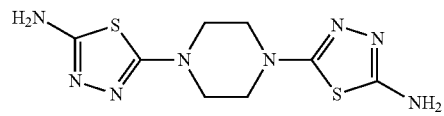

Example 1

5-[4-(5-amino-1,3,4-thiadiazol-2-yl)piperazin-1-yl]-1,3,4-thiadiazol-2-amine (UPGL00001)

A solution of 2-amino-5-bromothiadiazole (200 mg, 1.11 mmol), piperazine (48 mg, 0.55 mmol) and triethylamine (0.3 mL, 2.22 mmol) in EtOH (10 ml) in a sealed tube was heated at 65° C. overnight. The suspension that formed was cooled, concentrated to a small volume under a stream of N$_2$ and then treated with excess of water. The solid formed filtered, triturated with MeOH and dried to afford the product, 5-[4-(5-amino-1,3,4-thiadiazol-2-yl)piperazin-1-yl]-1,3,4-thiadiazol-2-amine, as an off-white solid (130 mg, 83% yield). $^1$HNMR (600 MHz, DMSO d6) δ 3.34 (s, 8H), 6.55 (s, 4H). ATR-IR (cm$^{-1}$) 3261, 3125, 2961, 2848, 1626, 1546, 1494, 1447, 1375, 1323, 1273, 1234, 1150, 1065, 1048, 1023, 924, 762, 688, 617. LC-MS (ESI) m/z for C$_8$H$_{12}$N$_8$S$_2$ calculated: 284.06, observed [M+H]: 285

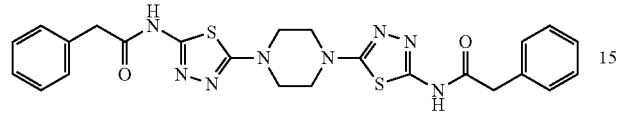

Example 2

2-phenyl-N-(5-{4-[5-(2-phenylacetamido)-1,3,4-thiadiazol-2-yl]piperazin-1-yl}-1,3,4-thiadiazol-2-yl)acetamide (UPGL00002)

A solution of 5-[4-(5-amino-1,3,4-thiadiazol-2-yl)piperazin-1-yl]-1,3,4-thiadiazol-2-amine (50 mg, 0.18 mmol), di-isopropylethyl amine (0.14 mL, 1.05 mmol) and phenylacetyl chloride (110 mg, 0.09 mL, 0.71 mmol) in DMF (4 mL) was stirred at room temperature for 3 hr. The solution was then treated with another portion of diisopropyl ethyl amine (0.14 mL, 1.05 mmol) and phenylacetyl chloride (110 mg, 0.09 mL, 0.71 mmol) and the mixture was stirred overnight. Next morning water was added and the solid formed filtered, collected, triturated with warm methanol and dried to afford the product, 2-phenyl-N-(5-{4-[5-(2-phenylacetamido)-1,3,4-thiadiazol-2-yl]piperazin-1-yl}-1,3,4-thiadiazol-2-yl)acetamide, as an off-white solid (40 mg, 43% yield). $^1$HNMR (600 MHz, DMSO-d6) δ 3.52 (s, 8H), 3.74 (s, 4), 7.26 (t, J=6.6 Hz, 2H), 7.33 (m, 8H), 12.37 (s, 2H). ATR-IR (cm$^{-1}$) 3172, 2858, 2802, 2726, 1681, 1573, 1494, 1463, 1438, 1351, 1309, 1242, 1154, 1024, 924, 809, 732, 695. LC-MS (ESI) m/z for C$_{24}$H$_{24}$N$_8$O$_2$S$_2$ calculated: 520.15, observed [M+H]: 521.

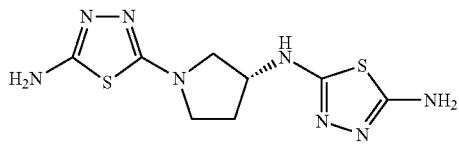 [SMILES: Nc1nnc(N[C@@H]2CCN(c3nnc(N)s3)C2)s1]

Example 3

2-N-[(3R)-1-(5-amino-1,3,4-thiadiazol-2-yl)pyrrolidin-3-yl]-1,3,4-thiadiazole-2,5-diamine (UPGL00003)

A solution of 2-amino-5-bromothiadiazole (200 mg, 1.11 mmol), (R)-2-aminopyrrolidine (48 mg, 0.55 mmol) and NaHCO$_3$ (280 mg, 3.33 mmol) in EtOH (6 mL) was heated in a sealed tube at 80° C. for 48 h. The mixture was then cooled, filtered, evaporated and the residue was purified via column and a 0-30% MeOH in CH$_2$Cl$_2$ gradient to afford the product, 2-N-[(3R)-1-(5-amino-1,3,4-thiadiazol-2-yl)pyrrolidin-3-yl]-1,3,4-thiadiazole-2,5-diamine, as an off white solid (75 mg, 48% yield). $^1$HNMR (600 MHz, DMSO-d6) δ 1.95 (m, 1H), 2.21 (m, 1H), 3.23 (dd, J=10.2, 3.6 Hz, 1H), 3.43 (distorted dd, J=16.8, 9.6 Hz, 1H), 3.56 (dd, J=10.2, 6.0 Hz, 1H), 4.19 (m, 1H), 6.32 (s, 2H), 6.33 (s, 2H), 7.10 (d, J=6 Hz, 1H). ATR-IR (cm$^{-1}$) 3266, 3121, 2923, 2856, 1630, 1610, 1561, 1492, 1470, 1336, 1297, 1236, 1189, 1028, 743. LC-MS (ESI) m/z for C$_8$H$_{12}$N$_8$S$_2$ calculated: 284.06, observed [M+H]: 285.

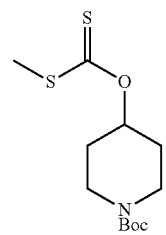 [SMILES: CSC(=S)OC1CCN(C(=O)OC(C)(C)C)CC1]

Intermediate 1 tert-Butyl 4-(((methylthio)carbonothioyl)oxy)piperidine-1-carboxylate

To solution of N-Boc-4-hydroxypiperidine (330 mg, 1.64 mmol) in THF (10 mL) was added NaH 60% suspension (79 mg, 1.97 mmol) at rt. After 15 min followed addition of CS$_2$ (187 mg, 148 L, 2.46 mmol) and then 5 min later addition of MeI (250 mg, 0.11 mL, 1.97 mmol). The reaction mixture was stirred at room temperature for 16 h and then partitioned between CH$_2$Cl$_2$ and water. Water layer extracted once more with CH$_2$Cl$_2$ and the combined CH$_2$Cl$_2$ layer was evaporated. The residue was chromatographed on a silica gel column with a 0-20% EtOAc gradient to afford the product, tert-butyl 4-(((methylthio)carbonothioyl)oxy)piperidine-1-carboxylate, as a colorless viscous oil (330 mg, 69% yield)

$^1$HNMR (600 MHz, CDCl$_3$) δ 1.49 (s, 9H), 1.84 (m, 2H), 1.99 (m, 2H), 2.58 (s, 3H), 3.37 (ddd, J=11.4, 7.8, 3.6 Hz, 2H), 3.69 (broad m, 2H), 5.75 (apparent sep, J=3.6 Hz). ATR-IR (cm$^{-1}$) 3002, 2973, 2925, 2864, 1687, 1476, 1452, 1418, 1364, 1311, 1273, 1237, 1209, 1162, 1129, 1049, 1008, 861, 767. LC-MS (ESI) m/z for C12H21NO3S2 calculated: 291.1, observed [M+Na]: 314.

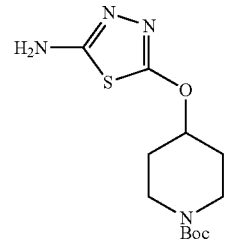 [SMILES: CC(C)(C)OC(=O)N1CCC(Oc2nnc(N)s2)CC1]

Intermediate 2 tert-butyl 4-((5-amino-1,3,4-thiadiazol-2-yl)oxy)piperidine-1-carboxylate

A solution of tert-butyl 4-(((methylthio)carbonothioyl)oxy)piperidine-1-carboxylate (320 mg 1.10 mmol), in MeOH (12 mL) was treated with anhydrous NH₂NH₂ (53 mg, 0.53 mL, 1.65 mmol). When the xanthate starting material was consumed, as indicated by TLC, the reaction solvent was evaporated. The residue was re-dissolved in 4 ml of MeOH and the solution was evaporated again. After repeating this methanol dissolution and evaporation process one more time, the residue in MeOH (10 mL) was treated with Et₃N (220 mg, 0.30 mL, 2.20 mmol) and solid BrCN (140 mg, 1.32 mmol). After stirring for 4 h at room temperature the solvent was evaporated and the residue was partitioned between EtOAc and water. The organic layer was then collected and evaporated and the residue chromatographed on a silica gel column with 0-100% EtOAc in CH₂Cl₂ to 0-5% MeOH in EtOAc gradient to afford the product, tert-butyl 4-((5-amino-1,3,4-thiadiazol-2-yl)oxy)piperidine-1-carboxylate, as a white powder (130 mg, 40% yield). ¹HNMR (600 MHz, CDCl₃) δ 1.48 (s, 9H), 1.80 (m, 2H), 2.06 (m, 2H), 3.31 (ddd, J=12.0, 8.4, 3.6 Hz, 2H), 3.73 (broad m, 2H), 4.71 (s, 2H), 5.13 (apparent sep, J=4.2 Hz, 1H). ATR-IR (cm⁻¹) 3383, 3255, 3086, 2973, 2935, 2872, 1657, 1558, 1496, 1427, 1365, 1280, 1243, 1228, 1165, 1125, 1074, 1052, 1024, 997, 901, 858, 843, 770, 749, 703, 675. LC-MS (ESI) m/z for $C_{12}H_{20}N_4O_3S$ calculated: 300.13, observed [M+H]: 301.

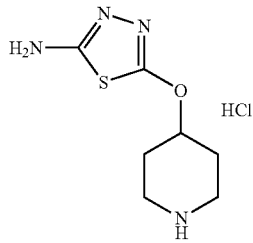 [SMILES: Nc1nnc(OC2CCNCC2)s1 ; Cl]

Intermediate 3

5-(Piperidin-4-yloxy)-1,3,4-thiadiazol-2-amine Hydrochloride

HCl gas was bubbled to a solution of tert-butyl 4-((5-amino-1,3,4-thiadiazol-2-yl)oxy)piperidine-1-carboxylate (500 mg, 1.66 mmol) in dioxane (15 mL) for 15 sec at room temperature. After stirring at room temperature for 1 h the solvent was evaporated to a solid residue that was washed with CH₂Cl₂ and then hexanes and then dried to afford the product, 5-(piperidin-4-yloxy)-1,3,4-thiadiazol-2-amine hydrochloride, as a white solid (390 mg, 99% yield). ¹HNMR (600 MHz, DMSO-d6) δ 1.98 (m, 2H), 2.17 (m, 2H), 3.08 (m, 2H), 3.20 (m, 2H), 5.04 (m, 1H), 8.15 (bs, 2H), 9.01 (bs, 2H). ATR-IR (cm⁻¹) 3288, 2996, 2925, 2908, 2792, 2745, 2699, 2506, 2449, 1630, 1572, 1530, 1309, 1270, 1171, 1125, 1050, 1020, 966, 945, 905, 862, 797, 745, 708, 659. LC-MS (ESI) m/z for free base $C_7H_{12}N_4OS$ calculated: 200.07, observed [M+H]: 201.

Example 4

5-(4-((5-amino-1,3,4-thiadiazol-2-yl)oxy)piperidin-1-yl)-1,3,4-thiadiazol-2-amine (UPGL00018)

A solution of 5-(piperidin-4-yloxy)-1,3,4-thiadiazol-2-amine hydrochloride (200 mg, 0.73 mmol), 2-amino-5-bromothiadiazole (140 mg, 0.77 mmol) and Et₃N (297 mg, 0.41 mL, 2.93 mmol) in EtOH (5 mL) was heated at 75° C. in a sealed vessel overnight. Next morning the reaction mixture was cooled and evaporated. The solid residue was suspended in small volume of water (approx. 3 mL) then filtered, air-dried, suspended in a small volume of CH₂Cl₂ (approx. 3 mL), filtered and dried to afford the product, 5-(4-((5-amino-1,3,4-thiadiazol-2-yl)oxy)piperidin-1-yl)-1,3,4-thiadiazol-2-amine (UPGL00018), as a brown solid (170 mg, 78% yield). ¹HNMR (600 MHz, DMSO-d6) δ 1.77 (m, 2H), 2.09 (m, 2H), 3.20 (ddd, J=12.6, 9.0, 3.6 Hz, 2H), 3.48 (m, 2H), 4.94 (apparent sep, J=4.2 Hz, 1H), 6.49 (s, 2H), 6.77 (s, 2H). ATR-IR (cm⁻¹) 3276, 3116, 2950, 2858, 1625, 1550, 1489, 1451, 1356, 1307, 1245, 1217, 1122, 1095, 1017, 951, 922, 878, 756, 677. LC-MS (ESI) m/z for $C_9H_{13}N_7OS_2$ calculated: 299.06, observed [M-H]: 298.

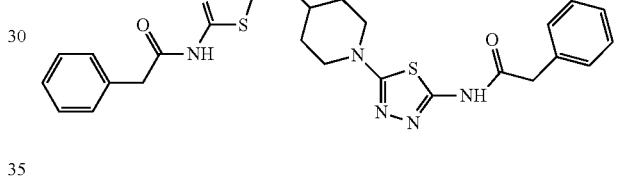

Example 5

2-Phenyl-N-{5-[1-(5-phenylacetylamino-[1,3,4]thiadiazol-2-yl)-piperidin-4-yloxy]-[1,3,4]thiadiazol-2-yl}-acetamide (UPGL00019)

A solution of 5-(4-((5-amino-1,3,4-thiadiazol-2-yl)oxy)piperidin-1-yl)-1,3,4-thiadiazol-2-amine (UPGL00019) (50 mg, 0.17 mmol) and Et₃N (70 mg, 0.10 mL, 0.67 mmol) in DMF (6 mL) was treated with phenylacetyl chloride (100 mg, 0.67 mmol). After stirring for 17 h at room temperature, the solution was evaporated to a small volume (approx. 1 mL) and excess of water was added. The suspension that was formed was then filtered and the solid was collected and air-dried. This solid was then suspended in CHCl₃ (approx. 3 mL), the mixture was briefly warmed to mild reflux, cooled and then excess of hexanes added. The solids were filtered, collected and treated twice more with hot CHCl₃ and hexanes as previously described and dried to afford the product, 2-phenyl-N-{5-[1-(5-phenylacetylamino-[1,3,4]thiadiazol-2-yl)-piperidin-4-yloxy]-[1,3,4]thiadiazol-2-yl}-acetamide (UPGL00019), as an off-white solid (61 mg, 73% yield). ¹HNMR (600 MHz, DMSO-d6) δ 1.84 (m, 2H), 2.13 (m, 2H), 3.37 (m, 2H), 3.65 (m, 2H), 3.76 (s, 2H), 3.78 (s, 2H), 5.13 (m, 1H), 7.25 (m, 2H), 7.31 (m, 8H), 12.31 (s, 1H), 12.58 (s, 1H). ATR-IR (cm⁻¹) 3176, 3060, 2955, 2856, 2809, 1686, 1569, 1503, 1455, 1351, 1351, 1315, 1268, 1218, 1141, 1087, 1016, 969, 947, 880, 830, 813, 758, 717, 695, 628. LC-MS (ESI) m/z for $C_{25}H_{25}N_7O_3S_2$ calculated: 535.15, observed [M+H]: 536.

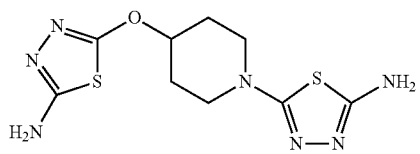 [SMILES: Nc1nnc(OC2CCN(c3nnc(N)s3)CC2)s1]

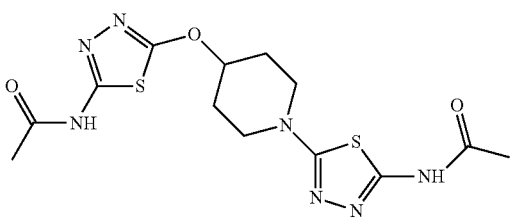 [SMILES: CC(=O)Nc1nnc(OC2CCN(c3nnc(NC(C)=O)s3)CC2)s1]

Example 6

N-{5-[1-(5-Acetylamino-[1,3,4]thiadiazol-2-yl)-piperidin-4-yloxy]-[1,3,4]thiadiazol-2-yl}-acetamide (UPGL00020)

A solution of 5-(4-((5-amino-1,3,4-thiadiazol-2-yl)oxy)piperidin-1-yl)-1,3,4-thiadiazol-2-amine (UPGL00019) (50 mg, 0.17 mmol) and $Et_3N$ (70 mg, 0.10 mL, 0.67 mmol) in DMF (6 mL) was treated with acetic acid anhydride (70 mg, 0.67 mmol). After stirring at room temperature overnight, the solution was evaporated to a small volume (approx. 1 mL) and excess of water was added. The suspension formed was then filtered and the solid obtained was collected, dried and suspended in hot $CHCl_3$ (approx. 3 mL). This $CHCl_3$ suspension was then cooled, treated with excess of hexanes and filtered. The resulting solid was suspended twice more in hot $CHCl_3$ and hexanes as previously described, filtered and dried to afford the product, N-{5-[1-(5-acetylamino-[1,3,4]thiadiazol-2-yl)-piperidin-4-yloxy]-[1,3,4]thiadiazol-2-yl}-acetamide (UPGL00020), as a tan solid (45 mg, 70% yield). $^1$HNMR (600 MHz, DMSO-d6) δ 1.85 (m, 2H), 2.11 (s, 3H), 2.13 (s, 3H), 2.15 (m, 2H), 3.37 (m, 2H); 3.67 (m, 2H), 5.14 (apparent sep, J=4.2 Hz), 12.0 (s, 1H), 12.30 (s, 1H). ATR-IR ($cm^{-1}$) 3181, 3099, 2876, 2806, 1686, 1574, 1503, 1448, 1368, 1308, 1267, 1249, 1113, 1096, 1009, 968, 947, 927, 881, 833, 816, 794, 696, 673, 647, 606. LC-MS (ESI) m/z for $C_{13}H_{17}N_7O_3S_2$ calculated: 383.08, observed (M−H): 382.

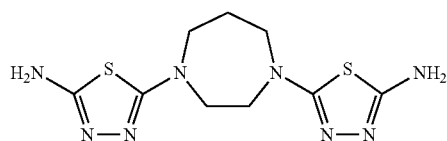 [SMILES: Nc1nnc(N2CCCN(c3nnc(N)s3)CC2)s1]

Example 7

5-[4-(5-amino-1,3,4-thiadiazol-2-yl)-1,4-diazepan-1-yl]-1,3,4-thiadiazol-2-amine (UPGL00017)

A solution of 2-amino-5-bromothiadiazole (200 mg, 1.10 mmol), homopiperazine (56 mg, 0.55 mmol) and $Et_3N$ (0.31 mL, 2.20 mmol) in EtOH (7 mL) was heated at 75° C. in a sealed tube overnight. The mixture was then cooled and evaporated to a small volume (approx. 3 mL) under a stream of nitrogen and excess of water (approx. 7 mL) was added. The suspension obtained from this operation was filtered and the solid was triturated with methanol and dried to afford the product, 5-[4-(5-amino-1,3,4-thiadiazol-2-yl)-1,4-diazepan-1-yl]-1,3,4-thiadiazol-2-amine (UPGL00017), as a pink solid. (150 mg, 45% yield). $^1$HNMR (600 MHz, DMSO-d6) δ 1.90 (apparent p, J=6.0 Hz, 2H), 3.44 (t, J=6.0 Hz, 4H), 3.60 (s, 4H), 6.34 (s, 4H). ATR-IR ($cm^{-1}$) 3272, 3111, 2945, 1524, 1571, 1500, 1437, 1383, 1357, 1318, 1295, 1250, 1213, 1191, 1085, 1047, 1026, 952, 922, 878, 742, 687, 653. LC-MS (ESI) m/z for $C_9H_{14}N_8S_2$ calculated: 298.08, observed [M+H]: 299.

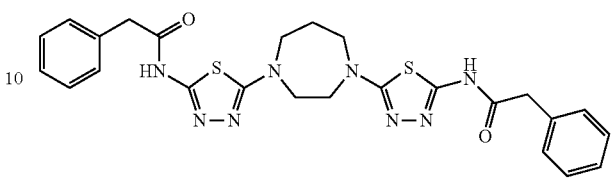

Example 8

2-Phenyl-N-{5-[4-(5-phenylacetylamino-[1,3,4]thiadiazol-2-yl)-[1,4]diazepan-1-yl]-[1,3,4]thiadiazol-2-yl}-acetamide (UPGL00016)

A mixture of 5-[4-(5-amino-1,3,4-thiadiazol-2-yl)-1,4-diazepan-1-yl]-1,3,4-thiadiazol-2-amine (UPGL00017) (80 mg, 0.27 mmol) in DMF (0.5 mL) was treated with excess of $Et_3N$ (0.63 mL, 4.50 mmol) and phenylacetyl chloride (460 mg, 2.99 mmol) and stirred at room temperature overnight. The mixture was then treated with excess of water. The solid precipitated was collected via filtration, washed with water, dried and triturated with hot hexanes and MeOH to afford the product, 2-phenyl-N-{5-[4-(5-phenylacetylamino-[1,3,4]thiadiazol-2-yl)-[1,4]diazepan-1-yl]-[1,3,4]thiadiazol-2-yl}-acetamide (UPGL00016), as an off-white solid. $^1$HNMR (600 MHz, DMSO-d6) δ 1.92 (apparent p, J=5.4 Hz, 2H), 3.54 (t, J=6.0 Hz, 4H), 3.69 (s, 4H), 3.74 (s, 4H), 7.19-7.40 (m, 10H), 12.23 (s, 2H). ATR IR ($cm^{-1}$) 3172, 3111, 3063, 2940, 2923, 2811, 2769, 2720, 1679, 1573, 1512, 1495, 1464, 1439, 1381, 1352, 1327, 1307, 1287, 1254, 1217, 1181, 1151, 1084, 1049, 1033, 972, 943, 921, 809, 752, 727, 693, 667, 641, 627, 614. LC-MS (ESI) m/z for $C_{25}H_{26}N_8O_2S_2$ calculated: 534.16, observed [M+H]: 535.

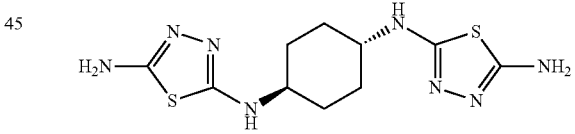

Example 9

N2,N2'-((anti)-cyclohexane-1,4-diyl)bis(1,3,4-thiadiazole-2,5-diamine) (UPGL00021)

A solution of 2-amino-5-bromothiadiazole (200 mg, 1.11 mmol), trans-1,4-diaminocyclohexane (65 mg, 0.56 mmol) and $Et_3N$ (280 mg, 0.38 mL, 2.75 mmol) in EtOH (4 mL) was stirred at 75° C. in a sealed vessel for 48 h. The reaction mixture was then cooled to room temperature, concentrated to a small volume (approx. 1 mL), excess of water was added (approx. 5 mL) and the solid formed was collected via filtration and washed with water and air-dried. Followed suspension in methanol (approx. 2 mL) and heating of the mixture to a mild reflux and then cooling to room temperature. The heating and cooling cycle was repeated three more times and the cooled mixture was then treated at room temperature with excess of $CH_2Cl_2$ and filtered. The solid was then washed with $CH_2Cl_2$ and dried to afford the product, N2,N2'-((anti)-cyclohexane-1,4-diyl)bis(1,3,4-thiadiazole-2,5-diamine) (UPGL00021), as an off-white, very insoluble solid (113 mg, 33% yield). $^1$HNMR (600 MHz, DMSO-d6) δ 1.21 (m, 4H), 2.03 (apparent d, J=6 Hz, 4H), 3.31 (m, 2H), 6.02 (s, 4H), 6.67 (d, J=7.2, 2H). ATR-IR (cm$^{-1}$) 3363, 3276, 3206, 3134, 3068, 2999, 2933, 2858, 1621, 1580, 1524, 1445, 1372, 1315, 1284, 1130, 1034, 808, 739, 713, 688, 620. LC-MS (ESI) m/z for $C_{10}H_{16}N_8S_2$ calculated: 312.09, observed [M+H]: 313.

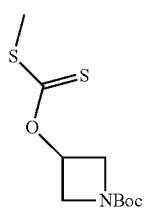 [SMILES: CSC(=S)OC1CN(C(=O)OC(C)(C)C)C1]

Intermediate 4 tert-Butyl 3-(((methylthio)carbonothioyl)oxy)azetidine-1-carboxylate

N-Boc-3-hydroxyazetidine (700 mg, 4.0 mmol) in THF (15 mL) was treated with NaH (60% suspension in mineral oil, 190 mg, 4.84 mmol) at room temperature. After 20 min followed addition of $CS_2$ (460 mg, 0.37 mL, 6.06 mmol) and then after 5 min followed addition of MeI (687 mg, 0.30 mL, 4.85 mmol). The reaction mixture was stirred at room temperature overnight and partitioned between $CH_2Cl_2$ and water. The $CH_2Cl_2$ layer was collected, evaporated and the residue was chromatographed on a silica gel column with 0-20% EtOAC in hexanes gradient to afford the product, tert-butyl 3-(((methylthio)carbonothioyl)oxy)azetidine-1-carboxylate, as a yellowish viscous oil (950 mg, 89% yield). $^1$HNMR (600 MHz, CDCl$_3$) δ1.47 (s, 9H), 2.61 (s, 3H), 4.05 (m, 2H), 4.32 (m, 2H), 5.63 (m, 1H). ATR-IR (cm$^{-1}$) 2975, 2929, 2882, 1698, 1477, 1455, 1389, 1364, 1295, 1253, 1203, 1135, 1103, 1055, 1019, 965, 927, 858, 769.

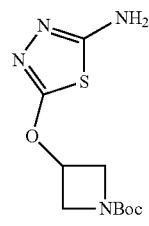 [SMILES: CC(C)(C)OC(=O)N1CC(Oc2nnc(N)s2)C1]

Intermediate 5 tert-Butyl 3-((5-amino-1,3,4-thiadiazol-2-yl)oxy)azetidine-1-carboxylate tert-Butyl 3-(((methylthio)carbonothioyl)oxy)azetidine-1-carboxylate (950 mg, 3.64 mmol) in MeOH (15 mL) was treated with $NH_2NH_2$ (0.137 mL, 140 mg, 4.37 mmol) at room temperature. Upon consumption of the starting material, as judged by TLC, the solvent was evaporated and the residue was re-dissolved in MeOH (approx. 16 mL). Followed addition of Et$_3$N (740 mg, 1.02 mL, 7.28 mmol) and BrCN (430 mg, 4.01 mmol) and the mixture was allowed to stir at room temperature overnight. Next morning the mixture was partitioned between EtOAc and water. The organic layer was then collected, dried over $Na_2SO_4$, filtered and evaporated. The residue was treated with $CH_2Cl_2$ (100 mL) and then the mixture was evaporated to approx. 40 mL in volume to afford a slurry. To this slurry was slowly added hexanes (60 mL). The slurry was filtered, the solid obtained was washed with hexanes and dried to afford the product, tert-Butyl 3-((5-amino-1,3,4-thiadiazol-2-yl)oxy)azetidine-1-carboxylate, as an off-white solid (803 mg, 81% yield). $^1$HNMR (600 MHz, DMSO-d6) δ 1.39 (s, 9H), 3.86 (broad s, 2H), 4.21 (broad s, 2H), 5.25 (m, 1H), 6.85 (s, 2H). ATR-IR (cm$^{-1}$) 3337, 3266, 3087, 2969, 2879, 1716, 1705, 1624, 1553, 1502, 1488, 1401, 1368, 1349, 1296, 1262, 1180, 1136, 1108, 1043, 858, 778, 691. LC-MS (ESI) m/z for $C_{10}H_{16}N_4O_3S$ calculated: 272.09, observed [M−H]: 271.

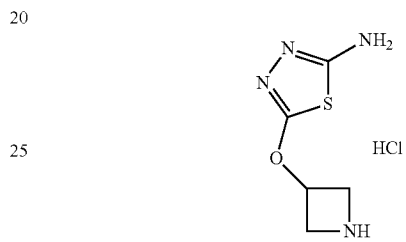

Intermediate 6

5-(Azetidin-3-yloxy)-[1,3,4]thiadiazol-2-ylamine Hydrochloride

To solution of tert-butyl 3-((5-amino-1,3,4-thiadiazol-2-yl)oxy)azetidine-1-carboxylate (800 mg, 2.95 mmol) in dioxane (15 mL) was bubbled HCl at room temperature for 15 seconds. The reaction mixture was capped, stirred for 70 min and then evaporated to a solid. The solid was triturated with hot $CH_2Cl_2$ and hot hexanes to afford the product, 5-(azetidin-3-yloxy)-[1,3,4]thiadiazol-2-ylamine hydrochloride, as a white solid (570 mg, 92% yield). $^1$HNMR (600 MHz, DMSO-d6) δ 4.10 (m, 2H), 4.33 (m, 2H), 5.37 (m, 1H), 8.49 (bs 2H), 9.43 (s, 1H), 9.71 (s, 1H). ATR-IR (cm$^{-1}$) 3274, 2871, 2618, 2552, 2435, 2323, 1635, 1583, 1561, 1426, 1292, 1269, 1239, 1147, 1076, 1002, 950, 881, 864, 786, 751, 686, 625. LC-MS (ESI) m/z for free base $C_5H_8N_4OS$ calculated: 172.04, observed [M+H]: 173.

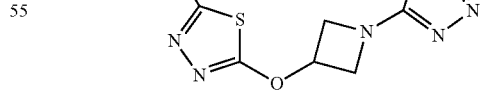

Example 10

5-{3-[(5-amino-1,3,4-thiadiazol-2-yl)oxy]azetidin-1-yl}-1,3,4-thiadiazol-2-amine (UPGL00022)

A solution of 5-(azetidin-3-yloxy)-[1,3,4]thiadiazol-2-ylamine hydrochloride (200 mg, 0.96 mmol), Et$_3$N (388 mg, 0.53 mL, 3.83 mmol), 2-amino-5-bromothiadiazole (180 mg, 1.00 mmol) in EtOH (5 mL) in a sealed vessel was heated at 75° C. for 16 h then cooled and evaporated to minimal volume. Water was then added and the suspension formed was filtered. The solid was collected and suspended in hot methanol (approx. 1 mL), cooled, and an equal amount of $CH_2Cl_2$ was added. This suspension was then filtered and the solid was collected and dried to afford the product, 5-{3-[(5-amino-1,3,4-thiadiazol-2-yl)oxy]azetidin-1-yl}-1,3,4-thiadiazol-2-amine (UPGL00022), as a tan solid (163 mg, 63% yield). $^1$HNMR (600 MHz, DMSO-d6) δ 3.96 (dd, J=9.0, 3.6 Hz, 2H), 4.29 (dd, J=9.0, 6.0 Hz, 2H), 5.41 (m, 1H), 6.56 (s, 2H), 6.86 (s, 2H). ATR-IR (cm$^{-1}$) 3256, 3085, 2954, 2858, 2786, 1631, 1567, 1497, 1455, 1366, 1330, 1237, 1174, 1113, 1060, 968, 760, 679. LC-MS (ESI) m/z for $C_7H_9N_7OS_2$ calculated: 271.03, observed [M+H]: 272.

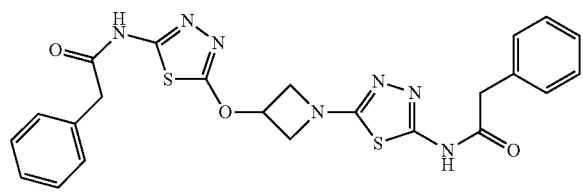 [SMILES: O=C(Cc1ccccc1)Nc1nnc(OC2CN(c3nnc(NC(=O)Cc4ccccc4)s3)C2)s1]

Example 11

2-Phenyl-N-[5-({1-[5-(2-phenylacetamido)-1,3,4-thiadiazol-2-yl]azetidin-3-yl}oxy)-1,3,4-thiadiazol-2-yl]acetamide (UPGL00023)

5-{3-[(5-amino-1,3,4-thiadiazol-2-yl)oxy]azetidin-1-yl}-1,3,4-thiadiazol-2-amine (UPGL00022) (50 mg, 0.18 mmol) in DMF (3 mL) was treated with $Et_3N$ (0.10 mL, 0.72 mmol) and phenylacetyl chloride (110 mg, 0.72 mmol, 0.10 mL). The reaction mixture was stirred overnight at room temperature them concentrated under a stream of nitrogen to a minimal volume and treated with excess of water to afford a suspension that was then filtered. The solid obtained was washed with water, dried and then suspended in hot $CHCl_3$. The hot mixture was then cooled to room temperature, treated with excess of hexanes and filtered and the solid obtained was dried to afford the product, 2-phenyl-N-[5-({1-[5-(2-phenylacetamido)-1,3,4-thiadiazol-2-yl]azetidin-3-yl}oxy)-1,3,4-thiadiazol-2-yl]acetamide (UPGL00023), as an off-white solid (51 mg, 54% yield). $^1$HNMR (600 MHz, DMSO-d6) δ 3.74 (s, 2H), 3.77 (s, 2H), 4.14 (apparent broad d, J=9 Hz, 2H), 4.45 (apparent t, J=7.8 Hz, 2H), 5.57 (bm, 1H), 7.25-7.42 (m, 10H), 12.40 (s, 1H), 12.67 (s, 1H). ATR-IR (cm$^{-1}$) 3175, 3061, 3029, 2869, 1687, 1570, 1494, 1455, 1173, 1137, 1095, 1056, 1030, 969, 813, 758, 720, 694, 645. LC-MS (ESI) m/z for $C_{23}H_{21}N_7O_3S_2$ calculated: 507.11, observed [M+H]: 508.

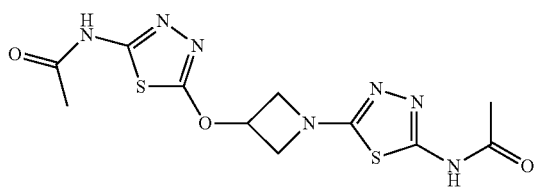 [SMILES: CC(=O)Nc1nnc(OC2CN(c3nnc(NC(C)=O)s3)C2)s1]

Example 12

N-{5-[1-(5-Acetylamino-[1,3,4]thiadiazol-2-yl)-azetidin-3-yloxy]-[1,3,4]thiadiazol-2-yl}-acetamide (UPGL00024)

A solution of 5-{3-[(5-amino-1,3,4-thiadiazol-2-yl)oxy]azetidin-1-yl}-1,3,4-thiadiazol-2-amine (UPGL00022) (50 mg, 0.18 mmol) and $Et_3N$ (0.10 mL, 0.72 mmol) in DMF (3 mL) was treated with acetic acid anhydride (75 mg, 0.07 mL, 0.72 mmol). The mixture was stirred overnight then concentrated under a stream of nitrogen to a very small volume and treated with water (approx. 4 mL). The solid formed was filtered, washed with water and suspended in MeOH. This mixture was then evaporated to dryness and the residue was suspended in $CH_2Cl_2$. This suspension was warmed briefly to a mild reflux, then cooled and filtered and the solid obtained dried to afford the product, N-{5-[1-(5-acetylamino-[1,3,4]thiadiazol-2-yl)-azetidin-3-yloxy]-[1,3,4]thiadiazol-2-yl}-acetamide (UPGL00024), as an off-white solid (35 mg, 53% yield). $^1$HNMR (600 MHz, DMSO-d6) δ 2.12 (s, 3H), 2.15 (s, 3H), 4.16 (dd, J=9.6, 3.6 Hz, 2H), 4.46 (dd, J=9.6, 6.6 Hz, 2H), 5.59 (m, 1H), 12.13 (broad s, 1H), 12.39 (broad s, 1H). ATR-IR (cm$^{-1}$) 3172, 3095, 2871, 2805, 1690, 1573, 1502, 1459, 1370, 1340, 1308, 1278, 1248, 1173, 1147, 1093, 1054, 1007, 967, 823, 696, 662, 649, 604. LC-MS (ESI) m/z for $C_{11}H_{13}N_7O_3S_2$ calculated: 355.05, observed [M+H]: 356.

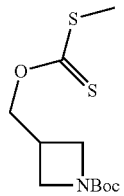 [SMILES: CSC(=S)OCC1CN(C(=O)OC(C)(C)C)C1]

Intermediate 7

3-Methylsulfanylthiocarboxyoxymethyl-azetidine-1-carboxylic Acid tert-butyl Ester 3-Hydroxymethyl-azetidine-1-carboxylic acid tert-butyl ester (980 mg, 5.24 mmol) in THF (25 mL) was treated with NaH (60% suspension in mineral oil, 250 mg, 6.29 mmol). The mixture was stirred for 15 min at room temperature and then $CS_2$ was added (0.48 mL, 598 mg, 7.86 mmol) and 10 min later followed addition of MeI (890 mg, 0.39 mL, 6.29 mmol). The reaction mixture was stirred at room temperature overnight and then partitioned between EtOAc and water. The EtOAc layer was collected, evaporated and the residue chromatographed on a silica gel column with 0-20% EtOAc in hexanes gradient to afford the product, 3-methylsulfanylthiocarboxyoxymethyl-azetidine-1-carboxylic acid tert-butyl ester, as a viscous colorless oil (800 mg, 54% yield). $^1$HNMR (600 MHz, CDCl$_3$) δ 1.45 (s, 9H), 2.56 (s, 3H), 3 (m, 1H), 3.75 (dd, J=9.0, 5.4 Hz, 2H), 4.06 (t, J=8.4 Hz, 2H), 4.71 (d, J=6.6 Hz, 2H). ATR-IR (cm$^{-1}$) 2972, 2883, 1694, 1477, 1455, 1401, 1364, 1297, 1207, 1130, 1053, 966, 936, 859, 770. LC-MS (ESI) m/z for $C_{11}H_{19}NO_3S_2$ calculated: 277.08, observed [M+Na]: 300.

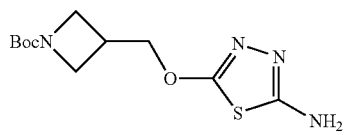 [SMILES: CC(C)(C)OC(=O)N1CC(COc2nnc(N)s2)C1]

Intermediate 8

3-(5-Amino-[1,3,4]thiadiazol-2-yloxymethyl)-azetidine-1-carboxylic Acid tert-butyl Ester A solution of 3-methylsulfanylthiocarboxyoxymethyl-azetidine-1-carboxylic acid tert-butyl ester (800 mg, 2.85 mmol) in 15 mL of MeOH at room temperature was treated with $NH_2NH_2$ (0.11 mL, 3.42 mmol). The mixture was stirred until TLC indicated consumption of the starting material and then evaporated under vacuum. The residue was re-dissolved in MeOH and to the resulting solution was added $Et_3N$ (0.80 mL, 5.70 mmol) and BrCN (320 mg, 3.13 mmol). This mixture was then stirred at room temperature overnight and partitioned between EtOAc and water. The water layer was extracted once more with EtOAc and the combined organic layer was then evaporated. The residue obtained was dissolved in $CHCl_3$ (approx. 17 mL) and the solution was treated with excess of hexanes to afford a precipitate. The precipitate was filtered, washed with hexanes and dried to afford the product, 3-(5-amino-[1,3,4]thiadiazol-2-yloxymethyl)-azetidine-1-carboxylic acid tert-butyl ester, as an off-white solid (560 mg, 69% yield). $^1$HNMR (600 MHz, $CDCl_3$) δ 1.43 (s, 9H), 3.01 (m, 1H), 3.74 (dd, J=9.0, 5.4 Hz, 2H), 4.06 (apparent t, J=9.0 Hz, 2H), 4.54 (d, J=6.6 Hz, 2H). ATR-IR (cm$^{-1}$) 3281, 3099, 2971, 2889, 1692, 1633, 1511, 1502, 1479, 1457, 1402, 1382, 1366, 1349, 1259, 1162, 1132, 1097, 1051, 948, 929, 882, 862, 769, 736, 690. LC-MS (ESI) m/z for $C_{11}H_{18}N_4O_3S$ calculated: 286.11, observed [M−H]: 285.

gen to a minimal volume. Excess of water (approx. 5 mL) was then added and the resulting mixture was condensed under a stream of nitrogen to a small volume (approx. 2 mL) and filtered. The solid obtained was suspended in MeOH. This mixture was evaporated to dryness and the resulting solid was triturated twice with hot $CH_2Cl_2$ and dried to afford the intermediate 5-(3-{[(5-amino-1,3,4-thiadiazol-2-yl)oxy]methyl}azetidin-1-yl)-1,3,4-thiadiazol-2-amine, as a dark brown solid (41 mg, 10% yield). $^1$HNMR (600 MHz, DMSO-d6) δ 3.14 (m, 1H), 3.74 (dd, J=7.2, 6.0 Hz, 2H), 3.99 (apparent t, J=8.4 Hz, 2H), 4.48 (d, J=6.6 Hz, 2H), 6.53 (s, 2H), 6.77 (s, 2H). This intermediate in DMF (2 mL) was treated with $Et_3N$ (0.08 mL, 0.59 mmol) and phenylacetyl chloride (90 mg, 0.57 mmol) and the mixture was stirred at room temperature overnight and then treated with excess of water to afford a gummy solid. All volatiles were evaporated and the residue was treated with MeOH (approximately 2 mL) and excess of water (approx. 6 mL). Upon stirring the gummy solid gradually turned into a fine powder that was collected by filtration and suspended in MeOH. This suspension was then concentrated to dryness and the residue was treated with $CH_2Cl_2$ and hexanes to afford the product, 2-phenyl-N-{5-[1-(5-phenylacetylamino-[1,3,4]thiadiazol-2-yl)-azetidin-3-ylmethoxy]-[1,3,4]thiadiazol-2-yl}-acetamide (UPGL00025), as an off-white solid (42 mg, 5% overall yield). $^1$HNMR (600 MHz, DMSO-d6) δ 3.73 (s, 2H), 3.76 (s, 2H), 3.88 (dd, J=7.8, 6.0 Hz, 2H), 4.13 (t, J=8.4 Hz, 2H), 4.63 (d, J=6.0 Hz), 7.24-7.36 (m, 10H), 12.36 (s, 1H), 12.58 (s, 1H). ATR-IR (cm$^{-1}$) 3182, 2879, 1688, 1571, 1508, 1454, 1359, 1316, 1300, 1257, 1161, 1150, 1074, 1029, 966, 803, 757, 715, 694, 650, 618. LC-MS (ESI) m/z for $C_{24}H_{23}N_7O_3S_2$ calculated: 521.13, observed [M+H]: 522.

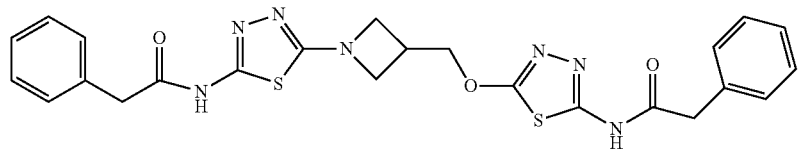 [SMILES: O=C(Cc1ccccc1)Nc1nnc(OCC2CN(c3nnc(NC(=O)Cc4ccccc4)s3)C2)s1]

Example 13

2-Phenyl-N-{5-[1-(5-phenylacetylamino-[1,3,4]thiadiazol-2-yl)-azetidin-3-ylmethoxy]-[1,3,4]thiadiazol-2-yl}-acetamide (UPGL00025)

3-(5-amino-[1,3,4]thiadiazol-2-yloxymethyl)-azetidine-1-carboxylic acid tert-butyl ester (450 mg, 1.39 mmol), was dissolved in 4N HCl in dioxane (5 mL) at room temperature. A white gum precipitated within 5 min of reaction time. The mixture was maintained at room temperature, until no starting material was observed by TLC, and then evaporated to a gummy residue. Followed addition of DMF (approx. 2 mL). This dissolved the residue and afforded a white precipitate that was collected via filtration, air-dried and dissolved in EtOH (10 mL). This solution was then treated with $Et_3N$ (0.76 mL, 5.56 mmol) and 2-amino-5-bromothiadiazole (250 mg, 1.39 mmol), heated at 75° C. in a sealed vessel overnight, cooled and concentrated under a stream on nitro-

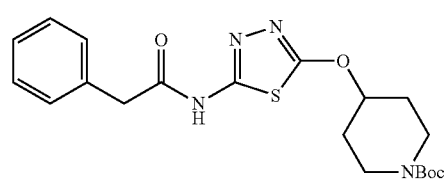 [SMILES: CC(C)(C)OC(=O)N1CCC(Oc2nnc(NC(=O)Cc3ccccc3)s2)CC1]

Intermediate 9

4-(5-Phenylacetylamino-[1,3,4]thiadiazol-2-yloxy)-piperidine-1-carboxylic Acid tert-butyl Ester A solution of tert-butyl 4-((5-amino-1,3,4-thiadiazol-2-yl)oxy)piperidine-1-carboxylate (220 mg, 0.73 mmol) in DMF (3 mL) was added N, N-diisopropylethylamine (0.306 mL, 2.20 mmol) and phenylacetyl chloride (170 mg, 1.10 mmol). The mixture was stirred for 72 h then partitioned between EtOAc and water. The water layer was extracted once more with EtOAc and the combined organic layer was concentrated. The residue was chromatographed on a silica gel column with 0-70% EtOAc in hexanes gradient to afford the product, 4-(5-phenylacetylamino-[1,3,4]thiadiazol-2-yloxy)-piperidine-1-carboxylic acid tert-butyl ester, as a white solid (225 mg, 73% yield). $^1$HNMR (600 MHz, CDCl$_3$) δ 1.44 (s, 9H), 1.83 (broad m, 2H), 2.01 (broad m, 2H), 3.27 (ddd, J=13.8, 10.2, 5.4 Hz), 3.67 (broad m, 2H), 3.90 (s, 2H), 5.14 (m, 1H), 7.29-7.41 (m, 5H). ATR-IR (cm$^{-1}$) 2967, 2950, 2914, 2882, 2799, 2729, 1684, 1567, 1503, 1477, 1453, 1425, 1358, 1328, 1308, 1284, 1262, 1229, 1151, 1130, 1060, 1017, 895, 866, 830, 818, 769, 724, 693, 640. LC-MS (ESI) m/z for C$_{20}$H$_{26}$N$_4$O$_4$S calculated: 418.17, observed [M+H]: 419.

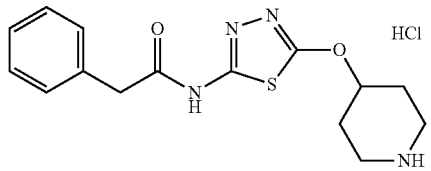 [SMILES: O=C(Cc1ccccc1)Nc1nnc(OC2CCNCC2)s1 ; Cl]

Intermediate 10

2-Phenyl-N-[5-(piperidin-4-yloxy)-[1,3,4]thiadiazol-2-yl]-acetamide hydrochloride salt A solution of 4-(5-phenylacetylamino-[1,3,4]thiadiazol-2-yloxy)-piperidine-1-carboxylic acid tert-butyl ester in dioxane (4 mL) was treated 4N HCl in dioxane (2 mL). Upon consumption of the starting material, as indicated by TLC, the volatiles were evaporated and the solid residue was triturated with CH$_2$Cl$_2$ and hexanes and then dried to afford the product, 2-phenyl-N-[5-(piperidin-4-yloxy)-[1,3,4]thiadiazol-2-yl]-acetamide hydrochloride salt, as a white solid (168 mg, 99% yield). $^1$HNMR (600 MHz, DMSO-d6) δ 1.98 (m, 2H), 2.20 (m, 2H), 3.10 (ddd, J=12.6, 8.4, 3.6 Hz, 2H), 3.23 (ddd, J=12.0, 7.2, 3.6 Hz, 2H), 3.77 (s, 2H), 5.16 (apparent sep, J=3.6 Hz, 1H), 7.25-7.37 (m, 5H), 8.82 (bs, 2H), 12.63 (bs, 1H). LC-MS (ESI) m/z for free base C$_{15}$H$_{18}$N$_4$O$_2$S calculated: 318.12, observed [M+H]: 319.

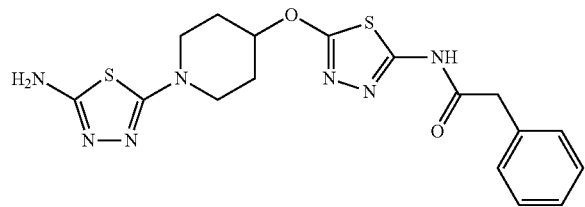 [SMILES: Nc1nnc(N2CCC(Oc3nnc(NC(=O)Cc4ccccc4)s3)CC2)s1]

Example 14

N-{5-[1-(5-Amino-[1,3,4]thiadiazol-2-yl)-piperidin-4-yloxy]-[1,3,4]thiadiazol-2-yl}-2-phenyl-acetamide (UPGL00031)

A solution of 2-phenyl-N-[5-(piperidin-4-yloxy)-[1,3,4] thiadiazol-2-yl]-acetamide hydrochloride salt (168 mg, 0.47 mmol), 2-amino-5-bromothiadiazole (89 mg, 0.49 mmol) and Et$_3$N (0.52 mL, 3.76 mmol) in EtOH (5 mL) was heated in a sealed tube at 75° C. overnight. The reaction mixture was then cooled, the solvent evaporated to a small volume and excess of water (approx. 5 mL) was added. The resulting suspension was filtered. The solid was washed with water, collected, triturated with MeOH, then boiling hexanes and dried to afford the product, N-{5-[1-(5-amino-[1,3,4]thiadiazol-2-yl)-piperidin-4-yloxy]-[1,3,4]thiadiazol-2-yl}-2-phenyl-acetamide, as a white solid (86 mg, 44% yield). $^1$HNMR (600 MHz, DMSO-d6) δ 1.82 (m, 2H), 2.12 (m, 2H), 3.22 (m, 2H), 3.51 (m, 2H), 3.76 (s, 2H), 5.10 (m, 1H), 6.49 (s, 2H), 7.24-7.36 (m, 5H), 12.47 (broad s, 1H). ATR IR (cm$^{-1}$) 3421, 3266, 3141, 2959, 2834, 2747, 1679, 1591, 1558, 1508, 1497, 1463, 1367, 1357, 1299, 1253, 1226, 1194, 1116, 1016, 954, 909, 845, 797, 781, 756, 708, 694, 687, 624. LC-MS (ESI) m/z for C$_{17}$H$_{19}$N$_7$O$_2$S$_2$ calculated: 417.10, observed [M–H]: 416.

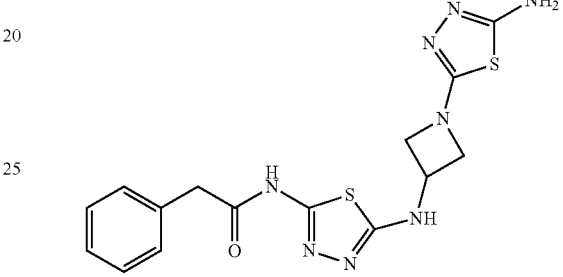

Example 15

N-(5-{[1-(5-amino-1,3,4-thiadiazol-2-yl)azetidin-3-yl]amino}-1,3,4-thiadiazol-2-yl)-2-phenylacetamide (UPGL00050)

A mixture of 1-N-Boc-3-aminoazetidine (520 mg, 3.02 mmol), 2-amino-5-bromothiadiazole (650 mg, 3.61 mmol) and NaHCO$_3$ (380 mg, 4.53 mmol) in EtOH (15 mL) in a sealed vessel was heated at 80° C. until consumption of the limiting reagent was indicated by TLC. The mixture was then cooled and partitioned between EtOAC and water. The water layer was extracted twice more with EtOAc and the combined organic layer was evaporated to a residue that was chromatographed on a silica gel column with 0-100% EtOAC in hexanes to afford a solid that without further characterization was dissolved in DMF (15 mL). This mixture was treated with Et$_3$N (0.84 mL, 6.04 mmol) and phenylacetyl chloride (560 mg, 3.63 mmol) and heated in a sealed vessel at 80° C. for 48 h. The reaction mixture was then cooled and partitioned between CH$_2$Cl$_2$ and water. The aqueous layer was extracted twice more with CH$_2$Cl$_2$ and the combined organic layer evaporated. The residue was chromatographed on a silica gel column with 0-100% EtOAc in hexanes to afford the intermediate tert-butyl 3-((5-(2-phenylacetamido)-1,3,4-thiadiazol-2-yl)amino) azetidine-1-carboxylate as a grey solid (154 mg, 0.39 mmol, 13% yield). $^1$HNMR (600 MHz, CDCl$_3$) δ 1.42 (s, 9H), 3.83 (dd, J=9.0, 4.8 Hz, 2H), 3.92 (s, 2H), 4.27 (dd, J=9.0, 7.8 Hz, 2H), 4.45 (bm, 1H), 5.45 (bs, 1H), 7.26-7.36 (m, 3H), 7.42 (apparent d, J=7.8 Hz, 2H), 12.23 (broad s, 1H). This intermediate was then dissolved in dioxane (1 mL) and treated with 4N HCl in dioxane solution (0.20 mL, 0.80 mmol) and stirred at room temperature for 95 min. Followed addition of another portion of dioxane (1 mL) and 4N HCl in dioxane (0.20 mL, 0.80 mmol). The resulting mixture was stirred for an additional 135 min and evaporated to dryness. The residue was triturated with CH$_2$Cl$_2$ and hexanes to afford the deprotected intermediate, N-(5-(azetidin-3-ylamino)-1,3,4-thiadiazol-2-yl)-2-phenylacetamide hydrochloride (48 mg, 0.15 mmol). This intermediate without any further delay was dissolved in EtOH (2 mL). Followed addition of 2-amino-5-bromothiadiazole (32 mg, 0.18 mmol) and NaHCO$_3$ (49 mg, 0.59 mmol) and the mixture was heated at 80° C. in a sealed vessel for 72 h. The solvent was evaporated to minimal volume and the residue was treated with excess of water (approx. 4 mL). The solid suspension formed was filtered and the solid was collected, dried, washed with CH$_2$Cl$_2$ and chromatographed with a silica gel column and 0-10% MeOH in CH$_2$Cl$_2$. Product containing fractions were collected, evaporated and the residue was triturated with hot CH$_2$Cl$_2$ to afford the product, N-(5-{[1-(5-amino-1,3,4-thiadiazol-2-yl)azetidin-3-yl]amino}-1,3,4-thiadiazol-2-yl)-2-phenylacetamide, as an off-white solid (6 mg, 1% yield overall). $^1$HNMR (600 MHz, DMSO-d6) δ 3.71 (s, 2H), 3.75 (dd, J=7.8, 6.0 Hz, 2H), 4.20 (apparent t, J=7.8 Hz, 2H), 4.57 (m, 1H), 6.52 (s, 2H), 7.22-7.40 (m, 5H), 7.99 (d, J=6.6 Hz, 1H), 12.25 (s, 1H). ATR IR (cm$^{-1}$) 3413, 3357, 3261, 3078, 3062, 2920, 2851, 1666, 1622, 1576, 1351, 1492, 1462, 1311, 1293, 1258, 1180, 1134, 1028, 966, 917, 868, 827, 758, 721, 694, 639. LC-MS (ESI) m/z for C$_{15}$H$_{16}$N$_8$OS$_2$ calculated: 388.09, observed [M+H]: 389.

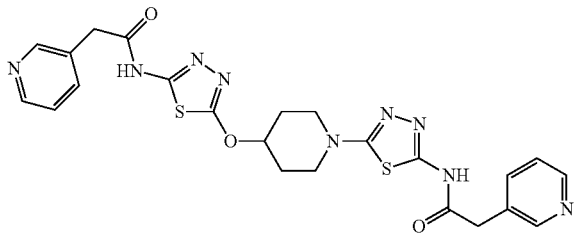 [SMILES: O=C(Cc1cccnc1)Nc1nnc(OC2CCN(c3nnc(NC(=O)Cc4cccnc4)s3)CC2)s1]

Example 16

2-(Pyridin-3-yl)-N-(5-(4-((5-(2-(pyridin-3-yl)acetamido)-1,3,4-thiadiazol-2-yl)oxy)piperidin-1-yl)-1,3,4-thiadiazol-2-yl)acetamide (UPGL00046)

A solution of 5-(4-((5-amino-1,3,4-thiadiazol-2-yl)oxy)piperidin-1-yl)-1,3,4-thiadiazol-2-amine (UPGL00018) (21 mg, 0.07 mmol), 3-pyridineacetic acid (24 mg, 0.18 mmol) and Et$_3$N (0.07 mL, 0.42 mmol) in DMF (1.5 mL) was treated with HATU (59 mg, 2.20 mmol) and stirred at room temperature for 48 h. The mixture was then concentrated to small volume (approx. 0.5 mL) under a stream of nitrogen. Excess of water was added (5 mL) and the precipitate formed was filtered, washed with water and hexanes and dried to afford the the product, 2-(pyridin-3-yl)-N-(5-(4-((5-(2-(pyridin-3-yl)acetamido)-1,3,4-thiadiazol-2-yl)oxy)piperidin-1-yl)-1,3,4-thiadiazol-2-yl)acetamide (UPGL00046), as an off-white solid (23 mg, 61% yield). $^1$HNMR (600 MHz, DMSO-d6) δ 1.85 (m, 2H), 2.14 (m, 2H), 3.38 (m, 2H), 3.66 (m, 2H), 3.85 (s, 2H), 3.88 (s, 2H), 5.15 (m, 1H), 7.48 (apparent t, J=6.6 Hz, 2H), 7.85 (d, J=6.6 Hz, 2H), 8.54 (d, J=4.2 Hz, 2H), 8.56 (s, 2H), 12.39 (s, 1H), 12.66 (s, 1H). ATR IR (cm$^{-1}$) 3149, 3072, 2846, 2743, 1685, 1562, 1496, 1453, 1295, 1258, 1188, 1116, 1018, 955, 840, 707, 632. LC-MS (ESI) m/z for C$_{23}$H$_{23}$N$_9$O$_3$S$_2$ calculated: 537.14, observed [M−H]: 536.

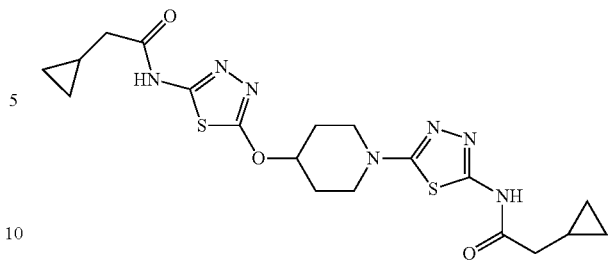

Example 17

2-Cyclopropyl-N-(5-(4-((5-(2-cyclopropylacetamido)-1,3,4-thiadiazol-2-yl)oxy)piperidin-1-yl)-1,3,4-thiadiazol-2-yl)acetamide (UPGL00030)

A solution of 5-(4-((5-amino-1,3,4-thiadiazol-2-yl)oxy)piperidin-1-yl)-1,3,4-thiadiazol-2-amine (UPGL00018) (50 mg, 0.17 mmol) and cyclopropylacetic acid (0.07 mL, 0.68 mmol) in DMF (5 mL) was treated with EDCI (130 mg, 0.68 mmol) and stirred at room temperature for 24 h. Then excess of water was added to the mixture and the solid formed was filtered, washed with water and CHCl$_3$ and dried. The solid was then triturated with MeOH, hexanes, hot CHCl$_3$ and dried to afford the product, 2-cyclopropyl-N-(5-(4-((5-(2-cyclopropylacetamido)-1,3,4-thiadiazol-2-yl)oxy)piperidin-1-yl)-1,3,4-thiadiazol-2-yl)acetamide (UPGL00030), as an off-white/beige solid (40 mg, 51% yield). $^1$HNMR (600 MHz, DMSO-d6) δ 0.18 (broad d, J=4.2 Hz, 4H), 0.47 (broad d, J=3.6 Hz, 4H), 1.02 (broad m, 2H), 1.86 (broad m, 2H), 2.15 (broad m, 2H), 2.29 (d, J=7.2 Hz, 2H), 2.31 (d, J=6.6 Hz), 3.39 (apparent t, J=9.0 Hz, 2H), 3.68 (m, 2H), 5.15 (broad m, 1H), 11.98 (s, 1H), 12.25 (s, 1H). ATR IR (cm$^{-1}$). 3171, 3080, 2998, 2929, 2905, 2854, 2759, 1685, 1678, 1561, 1498, 1458, 1450, 1386, 1375, 1324, 1263, 1250, 1208, 1187, 1115, 1018, 951, 926, 901, 875, 830, 805, 776, 728, 691, 631, 603. LC-MS (ESI) m/z for C$_{19}$H$_{25}$N$_7$O$_3$S$_2$ calculated: 463.15, observed [M+H]: 464.

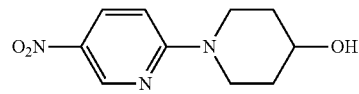 [SMILES: O=[N+]([O-])c1ccc(N2CCC(O)CC2)nc1]

Intermediate 11

1-(5-nitropyridin-2-yl)piperidin-4-ol

A solution of 2-chloro-5-nitropyridine (500 mg, 3.15 mmol), 4-hydroxypiperidine (320 mg, 3.15 mmol) and Et$_3$N (1.34 mL, 9.46 mmol) in EtOH (10 mL) was stirred at 70° C. in a sealed vessel for 6.5 h. The mixture was then cooled, evaporated to a small volume (approx. 3 mL) and treated with excess of water. The suspension obtained was then filtered and the solid was washed with water and dried to the product, 1-(5-nitropyridin-2-yl)piperidin-4-ol, a yellow solid (565 mg, 80% yield). $^1$HNMR (600 MHz, CDCl$_3$) δ 1.54 (d, J=4.2 Hz, 1H) 1.64 (m, 2H), 1.99 (m, 2H), 3.50 (ddd, J=12.6, 8.4, 3.0 Hz, 2H), 4.06 (m, 1H), 4.16 (m, 2H), 6.60 (d, J=11.4 Hz, 1H), 8.19 (dd, J=9.6, 3.0 Hz, 1H), 9.03 (d, J=2.4, 1H). ATR IR (cm$^{-1}$) 3463, 3104, 3084, 2942, 2916, 2873, 1589, 1571, 1514, 1478, 1433, 1338, 1328, 1285, 1243, 1213, 1160, 1129, 1115, 1067, 1016, 995, 976, 950, 933, 919, 819, 761, 744, 722, 638. LC-MS (ESI) m/z for $C_{10}H_{13}N_3O_3$ calculated: 223.10, observed [M+H]: 224.

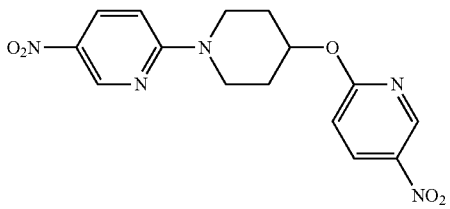 [SMILES: O=[N+]([O-])c1ccc(OC2CCN(c3ccc([N+](=O)[O-])cn3)CC2)nc1]

Intermediate 12

5-nitro-2-{4-[(5-nitropyridin-2-yl)oxy]piperidin-1-yl}pyridine 1-(5-nitropyridin-2-yl)piperidin-4-ol (150 mg, 0.67 mmol) and 2-chloro-5-nitropyridine (110 mg, 0.67 mmol) in THF (6 mL) at room temperature was treated with NaH (60% suspension in mineral oil, 52 mg, 1.30 mmol). Upon completion of the reaction, as judged by TLC, the mixture was partitioned between EtOAc and water. The water layer was extracted twice with EtOAc and the combined organic layer was evaporated. The residue was chromatographed on a silica gel column with a 0-100% EtOAc gradient to afford the product, 5-nitro-2-{4-[(5-nitropyridin-2-yl)oxy]piperidin-1-yl}pyridine, as a yellow solid (110 mg, 47% yield). $^1$HNMR (600 MHz, DMSO-d6) δ 1.74 (m, 2H), 2.11 (m, 2H), 3.67 (m, 2H), 4.16 (m, 2H), 5.45 (apparent sep, J=4.2 Hz, 1H), 7.01 (d, J=9.6 Hz, 1H), 7.03 (d, J=9.0 Hz, 1H), 8.21 (dd, J=9.6, 3.0 Hz, 1H), 8.48 (dd, J=9.6, 3.0 Hz, 1H), 8.96 (d, J=2.4 Hz, 1H), 9.09 (d, J=3.0 Hz, 1H). ATR IR (cm$^{-1}$) 3097, 2967, 2923, 2869, 1594, 1574, 1508, 1471, 1460, 1429, 1399, 1342, 1313, 1291, 1268, 1226, 1165, 1139, 1113, 1095, 1024, 993, 954, 925, 867, 833, 805, 759, 742, 720, 681, 659. LC-MS (ESI) m/z for $C_{15}H_{15}N_5O_5$ calculated: 345.11, observed [M+H]: 346.

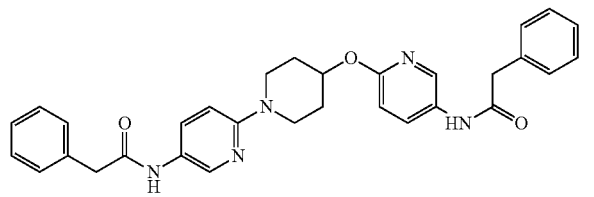 [SMILES: O=C(Cc1ccccc1)Nc1ccc(OC2CCN(c3ccc(NC(=O)Cc4ccccc4)cn3)CC2)nc1]

Example 18

2-Phenyl-N-[6-(4-{[5-(2-phenylacetamido)pyridin-2-yl]oxy}piperidin-1-yl)pyridin-3-yl]acetamide (UPGL00041)

A slurry of 10% Pd/C (34 mg) and 5-nitro-2-{4-[(5-nitropyridin-2-yl)oxy]piperidin-1-yl}pyridine (110 mg, 0.32 mmol) in 1:1 EtOH/EtOAc mixture (20 mL) was hydrogenated under 1 atm of $H_2$ for 160 min. The mixture was then filtered and the catalyst was washed with MeOH until no UV absorption detected in the wash stream. The combined organic layer was evaporated and the residue was chromatographed on a silica gel column with 0-5% MeOH in $CH_2Cl_2$ gradient to afford the corresponding reduced intermediate product (70 mg, 0.25 mmol, 77% yield) as an off-white solid. $^1$HNMR (600 MHz, DMSO-d6) δ 1.57 (m, 2H), 1.96 (m, 2H), 2.98 (ddd, J=13.2, 10.2, 3 Hz, 2H), 3.74 (m, 2H), 4.55 (broad s, 2H), 4.72 (broad s, 2H), 4.92 (apparent sep, J=4.2 Hz, 1H), 6.50 (d, J=9 Hz, 1H), 6.65 (d, J=9.0 Hz, 1H), 6.90 (dd, J=9.0, 3.0 Hz, 1H), 6.98 (dd, J=8.4, 2.4 Hz, 1H), 7.48 (d, J=2.4 Hz, 1H), 7.59 (d, J=3 Hz, 1H). This intermediate diamino pyridine was then dissolved in DMF (3 mL) and the solution was treated with Et$_3$N (0.21 mL, 1.47 mmol), phenylacetic acid (83 mg, 0.61 mmol) and HATU (230 mg, 0.51 mmol), stirred at room temperature overnight and then quenched with excess of water (approx. 5 mL). The slurry obtained from this operation was filtered. The solid was washed with water, triturated with MeOH and then with EtOAc and then dried to afford the product, 2-phenyl-N-[6-(4-{[5-(2-phenylacetamido)pyridin-2-yl]oxy}piperidin-1-yl)pyridin-3-yl]acetamide (UPGL00041), as an off-white solid. $^1$HNMR (600 MHz, DMSO-d6) δ1.61 (m, 2H), 2.01 (m, 2H), 3.23 (ddd, J=13.2, 9.6, 3.0 Hz, 2H), 3.60 (s, 2H), 3.63 (s, 2H), 3.93 (m, 2H), 5.15 (apparent sep, J=4.2 Hz, 1H), 6.76 (d, J=9.0 Hz, 1H), 6.85 (d, J=9.0 Hz, 1H), 7.26 (m, 2H), 7.33 (m, 8H), 7.77 (dd, J=9.0, 2.4 Hz, 1H), 7.89 (dd, J=9.0, 3.0 Hz, 1H), 8.28 (d, J=3.0 Hz, 1H), 8.34 (d, J=2.4 Hz, 1H), 10.01 (s, 1H), 10.20 (s, 1H). ATR IR (cm$^{-1}$) 3214, 3167, 3062, 3028, 2971, 2942, 2844, 1663, 1636, 1600, 1549, 1529, 1484, 1453, 1402, 1387, 1367, 1355, 1303, 1270, 1241, 1225, 1199, 1152, 1116, 1058, 1038, 1015, 983, 967, 930, 908, 844, 817, 767, 735, 710, 692, 647. LC-MS (ESI) m/z for $C_{31}H_{31}N_5O_3$ calculated: 521.24, observed [M+H]: 522.

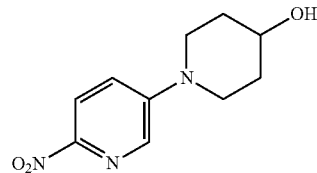 [SMILES: O=[N+]([O-])c1ccc(N2CCC(O)CC2)cn1]

Intermediate 13

1-(6-nitropyridin-3-yl)piperidin-4-ol

A mixture of 2-nitro-5-chloropyridine (500 mg, 3.16 mmol), 4-hydroxypiperidine (320 mg, 3.16 mmol) and $K_2CO_3$ (870 mg, 6.31 mmol) in DMSO (10 mL) in a sealed vessel was stirred at 90° C. overnight, then cooled, concentrated to a small volume (approx. 3 mL) and partitioned between EtOAc and water. The EtOAc layer was collected, evaporated and the residue was chromatographed on a silica gel column with 30-100% EtOAc in hexanes gradient to afford the product, 1-(6-nitropyridin-3-yl)piperidin-4-ol, as a yellow solid (460 mg, 65% yield).). $^1$HNMR (600 MHz, DMSO-d6) δ 1.42 (m, 2H), 1.81 (m, 2H), 3.24 (ddd, J=13.2, 9.6, 3.0 Hz, 2H), 3.75 (m, 1H), 3.83 (m, 2H), 4.78 (d, J=4.2 Hz, 1H), 7.45 (dd, J=9.0, 3.0 Hz, 1H), 8.11 (d, J=9.0 Hz, 1H), 8.23 (d, J=3.0 Hz, 1H). ATR IR (cm$^{-1}$) 3393, 3321, 3107, 3088, 2947, 2930, 2855, 1569, 1507, 1490, 1420, 1382, 1324, 1270, 1260, 1219, 1173, 1101, 1072, 1016, 1003, 962, 901, 824, 745, 692, 664, 629, 615. LC-MS (ESI) m/z for $C_{10}H_{13}N_3O_3$ calculated: 223.10, observed [M+H]: 224.

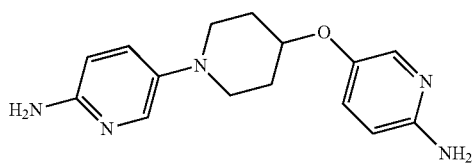 [SMILES: Nc1ccc(OC2CCN(c3ccc(N)nc3)CC2)cn1]

Intermediate 14

5-{4-[(6-aminopyridin-3-yl)oxy]piperidin-1-yl}pyridin-2-amine

A solution of 1-(6-nitropyridin-3-yl)piperidin-4-ol (110 mg, 0.49 mmol), 2-nitro-5-hydroxypyridine (69 mg, 0.49 mmol) and $Ph_3P$ (136 mg, 0.52 mmol) in THF (7 mL) was treated with diisopropyl azodicarboxylate, (0.10 mL, 0.52 mmol) and stirred at room temperature for 4 h. The mixture was then partitioned between $CH_2Cl_2$ and water. The organic layer was evaporated and the residue was chromatographed with a silica gel column and 0-20% acetone in $CH_2Cl_2$ gradient to afford the desired intermediate, 2-nitro-5-{4-[(6-nitropyridin-3-yl)oxy]piperidin-1-yl}pyridine, that without delay was dissolved in EtOH (10 mL). To this solution was added Fe (680 mg, 12.17 mmol), aq. saturated $NH_4Cl$ (4 mL) and the mixture was heated for 15 min at 80° C. then cooled and partitioned between EtOAc and water in the reaction flask. The EtOAC layer was pipetted out from the reaction vessel and the remaining layer was washed in a similar manner with portions of EtOAC until no UV absorption could be detected in the organic phase. The combined organic layer was then dried over $Na_2SO_4$, filtered, concentrated and the residue was chromatographed with a silica gel column and 0-10% MeOH in $CH_2Cl_2$ gradient to afford the product, 5-{4-[(6-aminopyridin-3-yl)oxy]piperidin-1-yl}pyridin-2-amine, an off-white/tan solid. (45 mg, 32% yield). $^1$HNMR (600 MHz, DMSO-d6) δ 1.68 (m, 2H), 1.97 (m, 2H), 2.77 (ddd, J=12.0, 9.6, 3.0 Hz, 2H), 3.22 (m, 2H), 4.19 (apparent sep, J=3.6 Hz, 1H), 5.39 (s, 2H), 5.51 (s, 2H), 6.39 (d, J=8.4 Hz, 1H), 6.41 (d, J=8.4 Hz), 7.16 (dd, J=8.4, 3.0 Hz, 1H), 7.18 (dd, J=9.0, 3.0 Hz, 1H), 7.63 (d, J=3 Hz, 1H), 7.67 (d, J=3 Hz, 1H). ATR IR (cm$^{-1}$) 3414, 3398, 3307, 3167, 3038, 2944, 2817, 1639, 1566, 1489, 1463, 1400, 1372, 1312, 1259, 1232, 1221, 1183, 1162, 1138, 1114, 1062, 1039, 1012, 979, 912, 822, 787, 743, 669, 645. LC-MS (ESI) m/z for $C_{15}H_{19}N_5O$ calculated: 285.16, observed [M+H]: 286.

Example 19

2-Phenyl-N-[5-(4-{[6-(2-phenylacetamido)pyridin-3-yl]oxy}piperidin-1-yl)pyridin-2-yl]acetamide (UPGL00043)

A solution of 5-{4-[(6-aminopyridin-3-yl)oxy]piperidin-1-yl}pyridin-2-amine (45 mg, 0.16 mmol) in DMF (3 mL) was treated with $Et_3N$ (0.13 mL, 0.95 mmol), phenylacetic acid (83 mg, 0.61 mmol) and HATU (230 mg, 0.51 mmol) and stirred at room temperature overnight. Followed addition of excess of water (approx. 5 mL). The suspension obtained from this operation was filtered. The solid obtained was then washed with water, triturated with MeOH and then with EtOAc and dried to afford the product, 2-phenyl-N-[6-(4-{[5-(2-phenylacetamido)pyridin-2-yl]oxy}piperidin-1-yl)pyridin-3-yl]acetamide (UPGL00041), as an off-white solid. $^1$HNMR (400 MHz, DMSO-d6) δ 1.73 (m, 2H), 2.04 (m, 2H), 3.05 (m, 2H), 3.48 (m, 2H), 3.66 (s, 2H), 3.68 (s, 2H), 4.56 (apparent sep, J=4.0 Hz, 1H), 7.20-7.40 (m, 10H), 7.39 (d, J=2.8 Hz, 1H), 7.42 (d, J=3.2 Hz, 1H), 7.47 (d, J=2.8 Hz, 1H); 7.49 (d, J=3.2 Hz, 1H), 7.89 (d, J=8.4 Hz, 1H), 7.98 (d, J=9.2 Hz, 1H), 8.04 (d, J=2.8 Hz, 1H), 8.07 (d, J=2.4 Hz, 1H), 10.42 (s, 1H), 10.55 (s, 1H). ATR IR (cm$^{-1}$) 3392, 3238, 3084, 3059, 3026, 2927, 2825, 1666, 1583, 1508, 1493, 1464, 1390, 1344, 1297, 1278, 1217, 1139, 1030, 962, 910, 830, 764, 720, 693, 631. LC-MS (ESI) m/z for $C_{31}H_{31}N_5O_3$ calculated: 521.24, observed [M+H]: 522.

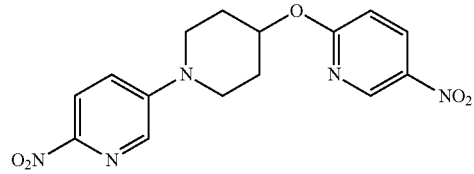

Intermediate 15

2-nitro-5-{4-[(5-nitropyridin-2-yl)oxy]piperidin-1-yl}pyridine

A solution of 1-(6-nitropyridin-3-yl)piperidin-4-ol (150 mg, 0.67 mmol) and 2-chloro-5-nitropyridine (110 mg, 0.67 mmol) in a 5/1 mixture of THF and DMSO (6 mL) was treated at room temperature with NaH (60% suspension in mineral oil, 40 mg, 1.0 mmol). The reaction mixture was then stirred at 50° C. until TLC indicated consumption of starting materials, then cooled to room temperature and partitioned between EtOAc and aq. saturated $NH_4Cl$. The aqueous layer was extracted with EtOAc until no UV absorption detected in the organic layer. The combined organic layer was evaporated and the residue was purified on

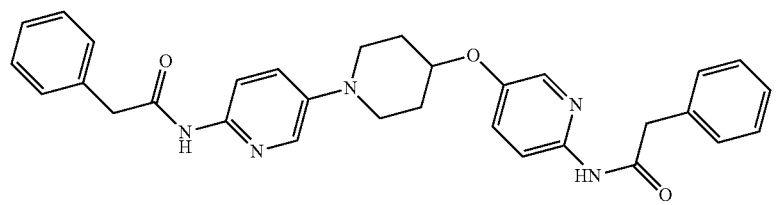 [SMILES: O=C(Cc1ccccc1)Nc1ccc(OC2CCN(c3ccc(NC(=O)Cc4ccccc4)nc3)CC2)cn1]

a silica gel column with 0-80% EtOAc in CH$_2$Cl$_2$ gradient to afford the product, 2-nitro-5-{4-[(5-nitropyridin-2-yl)oxy]piperidin-1-yl}pyridine, as a yellow solid (170 mg, 73% yield). $^1$HNMR (600 MHz, DMSO-d6) δ 1.81 (m, 2H), 2.14 (m, 2H), 3.50 (ddd, J=12.6, 9.0, 3.0 Hz, 2H), 3.90 (m, 2H), 5.44 (apparent sep, J=4.2 Hz 1H), 7.05 (d, J=9.0 Hz, 1H), 7.54 (dd, J=9.6, 3.0 Hz), 8.17 (d, J=7.2 Hz, 1H), 8.31 (d, J=2.4 Hz), 8.50 (dd, J=9.0, 2.4 Hz, 1H), 9.11 (d, J=3.0 Hz, 1H). ATR IR (cm$^{-1}$) 3058, 2963, 2921, 2854, 1684, 1600, 1569, 1502, 1469, 1418, 1399, 1343, 1311, 1283, 1270, 1222, 1182, 1170, 1108, 1090, 1021, 1000, 971, 948, 911, 829, 760, 746, 720, 693, 681, 658, 628. LC-MS (ESI) m/z for C$_{15}$H$_{15}$N$_5$O$_5$ calculated: 345.11, observed [M+H]: 346.

DMSO-d6) δ 1.74 (broad m, 2H), 2.06 (broad m, 2H), 3.03 (apparent broad t, J=10.2 Hz, 2H), 3.50 (m, 2H), 3.63 (s, 2H), 3.67 (s, 2H), 5.09 (broad m, 1H), 6.77 (d, J=9.0 Hz, 1H), 7.22-7.39 (m, 10H), 7.41 (broad d, J=9.0 Hz, 1H), 7.90 (apparent broad d, J=8.4 Hz, 1H), 8.04 (s, 1H), 8.34 (s, 1H), 10.20 (s, 1H), 10.46 (s, 1H). ATR IR (cm$^{-1}$) 3268, 3030, 2934, 2816, 2794, 1659, 1611, 1578, 1522, 1482, 1452, 1410, 1391, 1360, 1340, 1295, 1279, 1248, 1231, 1185, 1144, 1119, 1049, 1034, 1019, 980, 972, 916, 826, 748, 726, 704, 692, 657, 629. LC-MS (ESI) m/z for C$_{31}$H$_{31}$N$_5$O$_3$ calculated: 521.24, observed [M+H]: 522.

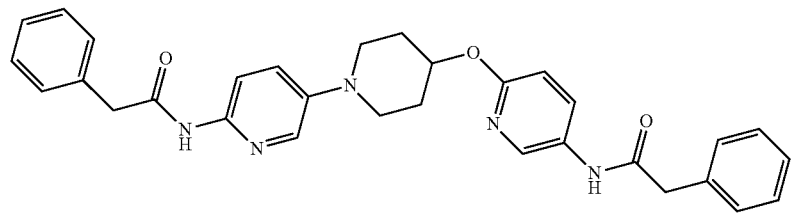 [SMILES: O=C(Cc1ccccc1)Nc1ccc(OC2CCN(c3ccc(NC(=O)Cc4ccccc4)nc3)CC2)nc1]

Example 20

2-Phenyl-N-[6-({1-[6-(2-phenylacetamido)pyridin-3-yl]piperidin-4-yl}oxy)pyridin-3-yl]acetamide (UPGL00044)

A mixture of 2-nitro-5-{4-[(5-nitropyridin-2-yl)oxy]piperidin-1-yl}pyridine (170 mg, 0.49 mmol) and 10% Pd/C (100 mg) in a 1:1 mixture of EtOAc and EtOH (20 mL) was hydrogenated under 1 atm of hydrogen for 4.5 h. The mixture was then filtered and the catalyst was washed with portions of MeOH until no UV absorption was detected in the washings. The combined organic layer was evaporated and the residue was chromatographed on a silica gel column and 0-10% MeOH in CH$_2$Cl$_2$ gradient to afford the intermediate reduction product as an off-white solid (97 mg, 0.34 mmol, 69% yield). $^1$HNMR (400 MHz, DMSO-d6) δ 1.68 (m, 2H), 2.02 (m, 2H), 2.80 (ddd, J=12.4, 9.6, 2.8 Hz, 2H), 3.23 (m, 2H), 4.72 (broad s, 2H), 4.87 (apparent sep, J=4.0 Hz, 1H), 5.37 (broad s, 2H), 6.40 (dd, J=8.8, 0.4 Hz), 6.52 (dd, J=8.8, 0.8 Hz, 1H), 7.00 (dd, J=8.8, 3.2 Hz, 1H), 7.19 (dd, 8.8, 2.8 Hz, 1H), 7.50 (dd, J=2.8, 0.4 Hz, 1H), 7.64 (d, J=2.8 Hz, 1H). This intermediate was then dissolved in DMF (3 mL). The resulting solution was treated with Et$_3$N (0.29 mL, 2.04 mmol), phenylacetic acid (110 mg, 0.85 mmol) and HATU (270 mg, 0.71 mmol), stirred at room temperature overnight, then concentrated to a small volume (approx. 1 mL) under a stream of nitrogen and partitioned between EtOAc and water. The water layer was extracted once more with EtOAc and the combined organic layer was evaporated. The residue was chromatographed on a silica gel column with 0-100% EtOAc in hexanes to afford the product, 2-phenyl-N-[6-({1-[6-(2-phenylacetamido)pyridin-3-yl]piperidin-4-yl}oxy)pyridin-3-yl]acetamide (UPGL00044), as a white solid (115 mg, 65% yield). $^1$HNMR (600 MHz,

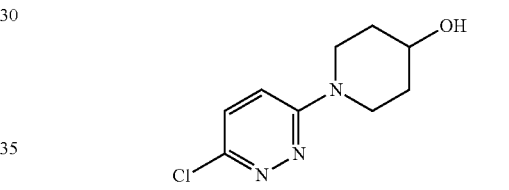

Intermediate 16

1-(6-Chloro-pyridazin-3-yl)-piperidin-4-ol

A mixture of 3,6 dichloropyridazine (500 mg, 3.36 mmol), 4-hydroxypiperidine (340 mg, 3.36 mmol) and Et$_3$N (0.94 mL, 6.72 mmol) in DMSO (5 mL) was stirred at 50° C. overnight. The reaction mixture was then partitioned between EtOAc and water. The water layer was saturated with solid NaCl and extracted with EtOAc portions until no UV absorption was detected in the organic layer. The combined EtOAc layer was then evaporated and the residue was chromatographed on a silica gel column with 0-100% EtOAc in hexanes gradient to afford the product, 1-(6-chloro-pyridazin-3-yl)-piperidin-4-ol, as a white solid (640 mg, 89% yield). $^1$HNMR (600 MHz, CD$_3$OD) δ 1.54 (m, 2H), 1.94 (m, 2H), 3.28 (m, 2H), 3.89 (apparent sep, J=4.2 Hz, 1H), 4.11 (apparent dt, J=13.2, 4.8 Hz, 2H), 7.32 (d, J=9.6 Hz, 1H), 7.4 (d, J=9.6 Hz, 1H). ATR IR (cm$^{-1}$) 3199, 3077, 3008, 2991, 2941, 2847, 1583, 1530, 1429, 1362, 1312, 1298, 1257, 1237, 1224, 1184, 1167, 1148, 1107, 1061, 1032, 1012, 981, 921, 835, 766, 745, 670, 634. (ESI) m/z for C$_9$H$_{12}$ClN$_3$O calculated: 213.07, observed [M+H]: 214.

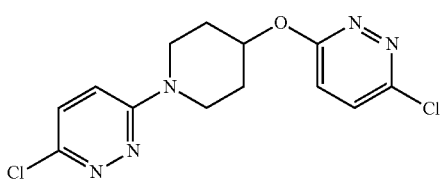 [SMILES: Clc1ccc(OC2CCN(c3ccc(Cl)nn3)CC2)nn1]

Intermediate 17

3-Chloro-6-{4-[(6-chloropyridazin-3-yl)oxy]piperidin-1-yl}pyridazine

A solution of 1-(6-chloro-pyridazin-3-yl)-piperidin-4-ol (200 mg, 0.94 mmol) and 3,6-dichloropyridazine (139 mg, 0.94 mmol) in THF (4 mL) was treated with NaH (60% suspension in mineral oil, 34 mg, 1.41 mmol). The mixture was stirred at room temperature for 30 min, at 50° C. for 23.5 h and then cooled and partitioned between EtOAc and aq. saturated NH$_4$Cl. The aqueous layer was washed with portions of EtOAc until no UV absorption in the organic layer and then the combined organic layer was evaporated. The residue was chromatographed on a silica gel column with 0-100% EtOAc in hexanes gradient to afford the product, 3-chloro-6-{4-[(6-chloropyridazin-3-yl)oxy]piperidin-1-yl}pyridazine, a white solid (254 mg, 82% yield). $^1$HNMR (600 MHz, DMSO-d6) δ 1.76 (m, 2H), 2.14 (m, 2H), 3.50 (ddd, J=13.2, 9.0, 3.6 Hz, 2H), 4.04 (m, 2H), 5.45 (apparent sep, J=4.2 Hz, 1H), 7.34 (d, J=9.6 Hz, 1H), 7.46 (d, J=10.2 Hz, 1H), 7.54 (d, J=9.6 Hz, 1H), 7.82 (d, J=9.0 Hz, 1H). ATR IR (cm$^{-1}$) 3051, 2973, 2958, 2938, 2920, 2858, 1583, 1529, 1440, 1415, 1369, 1330, 1301, 1246, 1236, 1188, 1167, 1150, 1121, 1082, 1047, 1030, 972, 946, 919, 848, 827, 764, 700, 675, 629. LC-MS (ESI) m/z for C$_{13}$H$_{13}$Cl$_2$N$_5$O calculated: 325.05, observed [M+H]: 326.

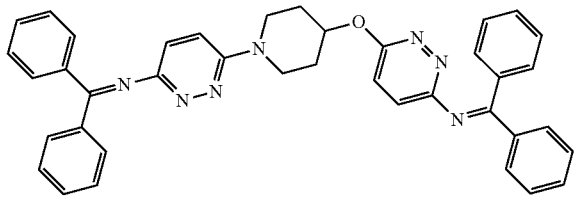 [SMILES: c1ccc(C(=Nc2ccc(OC3CCN(c4ccc(N=C(c5ccccc5)c5ccccc5)nn4)CC3)nn2)c2ccccc2)cc1]

Intermediate 18

N-(diphenylmethylidene)-6-[4-({6-[(diphenylmethylidene)amino]pyridazin-3-yl}oxy)piperidin-1-yl]pyridazin-3-amine A mixture of 3-chloro-6-{4-[(6-chloropyridazin-3-yl)oxy]piperidin-1-yl}pyridazine (150 mg, 0.46 mmol), benzophenone imine (175 mg, 0.97 mmol), (±)-BINAP (86 mg, 0.14 mmol) and Cs$_2$CO$_3$ (1.19 g, 3.68 mmol) in toluene (5 mL) in a sealed tube was degassed via N$_2$ bubbling (approx. 5 min). Followed addition of Pd$_2$(dba)$_3$ (60 mg, 0.07 mmol) sealing of the reaction vessel and stirring at 120° C. for 13.5 h. The reaction mixture was then cooled and filtered. The solids were washed with EtOAC portions until no UV absorption was detected in the washings and the combined EtOAc layer was evaporated. The residue was chromatographed with a silica gel column and 0-100% EtOAc in CH$_2$Cl$_2$ to afford the product, N-(diphenylmethylidene)-6-[4-({6-[(diphenylmethylidene)amino]pyridazin-3-yl}oxy)piperidin-1-yl]pyridazin-3-amine, that after a precipitation out of CH$_2$Cl$_2$ with excess of hexanes was isolated as an off-white solid (80 mg, 30% yield). $^1$HNMR (600 MHz, DMSO-d6) δ 1.62 (m, 2H), 2.04 (m, 2H), 3.25 (apparent t, J=9.6H, 2H), 3.95 (m, 2H), 5.26 (broad m, 1H), 6.88 (d, J=9.6 Hz, 1H), 7.04 (d, J=9.0 Hz, 1H), 7.12 (d, J=9.0 Hz, 1H), 7.16 (m, 4H), 7.21 (d, J=9.6 Hz, 1H), 7.36 (m, 6H), 7.52 (m, 4H), 7.60 (m, 2H), 7.71 (dd, J=13.2, 7.2 Hz, 4H). ATR IR (cm$^{-1}$) 3062, 2987, 2963, 2940, 2917, 1625, 1594, 1571, 1534, 1475, 1444, 1421, 1308, 1297, 1250, 1231, 1176, 1155, 1122, 1097, 1074, 1018, 995, 958, 906, 836, 780, 763, 734, 695, 650, 634. LC-MS (ESI) m/z for C$_{39}$H$_{33}$N$_7$O calculated: 615.27, observed [M+H]: 616.

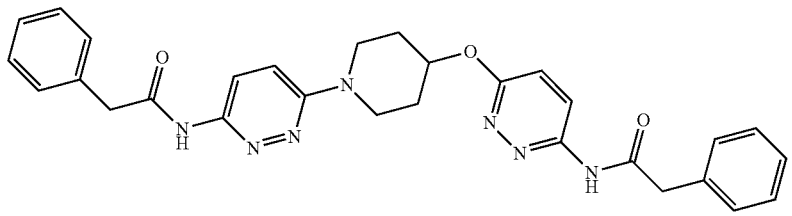 [SMILES: O=C(Cc1ccccc1)Nc1ccc(OC2CCN(c3ccc(NC(=O)Cc4ccccc4)nn3)CC2)nn1]

Example 21

2-Phenyl-N-{6-[1-(6-phenylacetylamino-pyridazin-3-yl)-piperidin-4-yloxy]-pyridazin-3-yl}-acetamide (UPGL00045)

A mixture of N-(diphenylmethylidene)-6-[4-({6-[(diphenylmethylidene)amino]pyridazin-3-yl}oxy)piperidin-1-yl]pyridazin-3-amine (100 mg, 0.16 mmol), hydroxylamine hydrochloride (25 mg, 0.34 mmol) and NaOAc (67 mg, 0.82 mmol) in MeOH (15 mL) was stirred at room temperature for 1 h and then concentrated to dryness. The residue was applied on a silica gel column directly and chromatographed with 0-15% MeOH in CH$_2$Cl$_2$ gradient to afford the desired intermediate 6-{4-[(6-aminopyridazin-3-yl)oxy]piperidin-1-yl}pyridazin-3-amine that was isolated as an off-white solid after precipitation out of CH$_2$Cl$_2$ with excess of hexanes (33 mg, 0.12 mmol, 75% yield). $^1$HNMR (600 MHz, DMSO-d6) δ 1.66 (m, 2H), 2.05 (m, 2H), 3.12 (ddd, J=12.6, 9.6, 2.4 Hz, 2H), 3.77 (m, 2H), 5.13 (apparent sep, J=4.2 Hz, 1H), 5.63 (s, 2H), 5.89 (s, 2H), 6.72 (d, J=9.6 Hz, 1H), 6.84 (apparent q, 2H), 7.16 (d, J=9.6, 1H). This intermediate was then dissolved in DMF (2 mL) and the resulting solution was treated with Et$_3$N (0.08 mL, 0.59 mmol), phenylacetic acid (33 mg, 0.25 mmol) and HATU (95 mg, 0.25 mmol). This solution was stirred at room temperature for 6 h and then partitioned between EtOAc and water. The water layer was extracted once more with EtOAc and the combined organic layer was evaporated. The residue was chromatographed on a silica gel column with 0-100% EtOAc in CH$_2$Cl$_2$ to afford the product, 2-phenyl-N-{6-[1-(6-phenylacetylamino-pyridazin-3-yl)-piperidin-4-yloxy]-pyridazin-3-yl}-acetamide (UPGL00045), as a white solid. $^1$HNMR (600 MHz, DMSO-d6) δ 1.72 (m, 2H), 2.09 (m, 2H), 3.40 (apparent broad t, J=10.2 Hz, 2H), 3.71 (s, 2H), 3.75 (s, 2H), 3.97 (m, 2H), 5.38 (m, 1H), 7.20 (d, J=9.0 Hz, 1H) 7.25 (m, 2H), 7.34 (m, 8H), 7.38 (d, J=9.6 Hz, 1H), 8.00 (d, J=10.2 Hz, 1H), 8.19 (d, J=9.6 Hz, 1H), 10.91 (s, 1H), 11.11 (s, 1H). ATR IR (cm$^{-1}$) 3348, 3221, 3192, 3102, 3059, 3028, 2949, 2919, 2839, 1685, 1509, 1421, 1356, 1313, 1295, 1258, 1234, 1227, 1137, 1119, 1095, 1020, 997, 951, 907, 864, 834, 813, 773, 731, 713, 692, 654, 635, 616. LC-MS (ESI) m/z for C$_{29}$H$_{29}$N$_7$O$_3$ calculated: 523.23, observed [M+H]: 524.

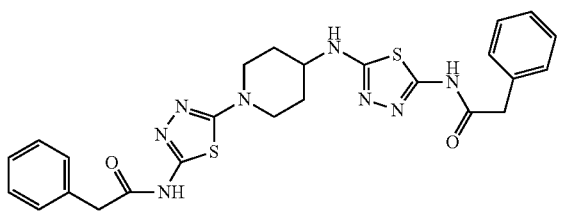 [SMILES: O=C(Cc1ccccc1)Nc1nnc(NC2CCN(c3nnc(NC(=O)Cc4ccccc4)s3)CC2)s1]

Example 22

2-Phenyl-N-(5-(4-((5-(2-phenylacetamido)-1,3,4-thiadiazol-2-yl)amino)piperidin-1-yl)-1,3,4-thiadiazol-2-yl)acetamide (UPGL00004)

To a solution of N2-(1-(5-amino-1,3,4-thiadiazol-2-yl)piperidin-4-yl)-1,3,4-thiadiazole-2,5-diamine (UPGL00005) (34 mg, 0.11 mmol) in DMF (0.3 ml) is added Et$_3$N (0.35 mmol, 0.05 ml) and phenylacetyl chloride (35 mg, 0.23 mmol). When TLC indicated consumption of the starting material excess of water was added. The suspension formed was filtered, and the solid collected and chromatographed with a 0-10% methanol in methylene chloride gradient to afford the product, 2-phenyl-N-(5-(4-((5-(2-phenylacetamido)-1,3,4-thiadiazol-2-yl)amino)piperidin-1-yl)-1,3,4-thiadiazol-2-yl)acetamide (UPGL00004), as a white solid, (34 mg, 55% yield). $^1$H NMR (600 MHz, DMSO-d6) δ 1.46-1.55 (m, 2H), 2.04 (d, J=9.6 Hz, 2H), 3.18 (t, J=10.8 Hz, 2H), 3.68-3.78 (m, 7H), 7.23-7.39 (m, 10H), 12.21 (brd s, 1H), 12.31 (brd s, 1H). ATR IR (cm$^{-1}$) 3389, 3324, 2852, 1682, 1662, 1577, 1493, 1356, 1315, 1299, 1128, 967, 833, 811, 757, 713, 693. LC-MS (APCI), m/z for C$_{25}$H$_{26}$N$_8$O$_2$S$_2$ calculated: 534.16, observed [M+H]: 535.

Example 23

(R)-2-Phenyl-N-(5-(3-((5-(2-phenylacetamido)-1,3,4-thiadiazol-2-yl)amino)pyrrolidin-1-yl)-1,3,4-thiadiazol-2-yl)acetamide (UPGL00011)

To a stirred solution of 2-N-[(3R)-1-(5-amino-1,3,4-thiadiazol-2-yl)pyrrolidin-3-yl]-1,3,4-thiadiazole-2,5-diamine (UPGL00003) (82 mg, 0.29 mmol) in DMF (1.5 mL) is added triethylamine (0.12 ml, 0.86 mmol) and phenylacetyl chloride (0.08 mL, 0.60 mmol). The reaction mixture was stirred at room temperature until TLC indicated consumption of the limiting reagent and then treated with excess of water to afford a suspension. The suspension formed was filtered and the solid was washed with water dried and chromatographed using a 0-15% methanol in methylene chloride gradient, to yield the product (R)-2-phenyl-N-(5-(3-((5-(2-phenylacetamido)-1,3,4-thiadiazol-2-yl)amino)pyrrolidin-1-yl)-1,3,4-thiadiazol-2-yl)acetamide (UPGL00011) as an off-white solid (55 mg, 37% yield). $^1$HNMR (600 MHz, DMSO-d6) δ 2.01-2.06 (m, 1H), 2.25-2.32 (m, 1H), 3.36-3.39 (m, 1H), 3.43-3.53 (m, 2H), 3.67 (m, 1H), 3.71 (s, 2H), 3.72 (s, 2H), 4.32-4.37 (m, 1H), 7.23-7.34 (m, 10H) 7.65 (d, 1H, J=6.0 Hz), 12.21 (brd s, 1H), 12.25 (brd s, 1H). ATR IR (cm$^{-1}$) 3339, 3186, 3061, 3028, 2868, 2799, 2735, 1682, 1662, 1577, 1512, 1457, 1358, 1316, 1296, 1226, 1185, 1160, 1147, 1073, 1029, 967, 842, 801, 755, 713, 693, 640. LC-MS (ESI) m/z for C$_{25}$H$_{26}$N$_8$O$_2$S$_2$ calculated: 520.14, observed [M+H]: 521.

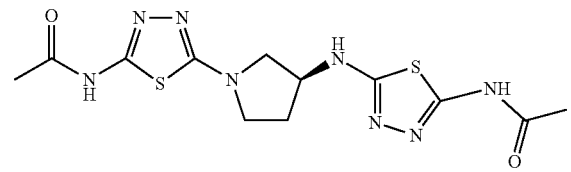

Example 24

N-(5-{[(3S)-1-(5-acetamido-1,3,4-thiadiazol-2-yl)pyrrolidin-3-yl]amino}-1,3,4-thiadiazol-2-yl)acetamide (UPGL00012)

To a stirred solution of (S)—N2-(1-(5-amino-1,3,4-thiadiazol-2-yl) pyrrolidin-3-yl)-1,3,4-thiadiazole-2,5-diamine (UPGL00006) (124 mg, 0.44 mmol) in DMF (2 ml) was added Et$_3$N (0.18 ml, 1.31 mmol) and acetic anhydride (0.08 mL, 0.88 mmol). After stirring at room temperature overnight the reaction mixture was treated with excess of water and the suspension formed was filtered, washed with water and dried to yield the product, (S)—N-(5-(3-((5-acetamido-

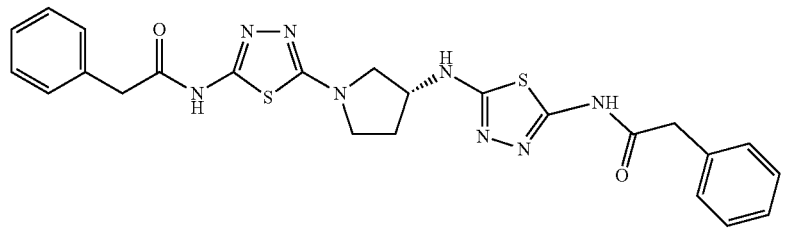 [SMILES: O=C(Cc1ccccc1)Nc1nnc(N[C@@H]2CCN(c3nnc(NC(=O)Cc4ccccc4)s3)C2)s1]

1,3,4-thiadiazol-2-yl)amino)pyrrolidin-1-yl)-1,3,4-thiadiazol-2-yl)acetamide (UPGL00012), as an off-white/tan solid (40 mg, 25% yield). 1HNMR (600 MHz, DMSO-d6) δ 2.08 (multiple overlapping with s, 4H), 2.10 (s, 3H), 2.26-2.34 (m, 1H), 3.41 (dd, J=10.2, 3.6 Hz, 1H), 3.44-3.55 (m, 2H), 3.71 (dd, J=10.2, 6.0 Hz, 1H), 4.32-4.38 (m, 1H), 7.63 (d, J=6.0 Hz, 1H), 11.94 (s, 1H), 11.97 (s, 1H). LC-MS (ESI), m/z for $C_{12}H_{16}N_8O_2S_2$ calculated: 368.08, observed [M+H]: 369.

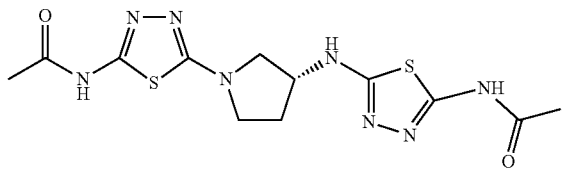 [SMILES: CC(=O)Nc1nnc(N[C@@H]2CCN(c3nnc(NC(C)=O)s3)C2)s1]

Example 25

N-(5-{[(3R)-1-(5-acetamido-1,3,4-thiadiazol-2-yl)pyrrolidin-3-yl]amino}-1,3,4-thiadiazol-2-yl)acetamide (UPGL00013)

To a stirred solution of 2-N-[(3R)-1-(5-amino-1,3,4-thiadiazol-2-yl)pyrrolidin-3-yl]-1,3,4-thiadiazole-2,5-diamine (80 mg, 0.28 mmol) in DMF (1.3 ml) is added Et₃N (0.12 ml, 0.84 mmol) and acetic anhydride (0.053 ml, 0.56 mmol). The reaction was stirred at room temperature overnight and then treated with excess of water. The suspension formed was filtered and the solid was washed with water and dried to yield the product, N-(5-{[(3R)-1-(5-acetamido-1,3,4-thiadiazol-2-yl)pyrrolidin-3-yl]amino}-1,3,4-thiadiazol-2-yl)acetamide (UPGL00013) as an off-white/tan solid (44 mg, 43% yield). 1HNMR (600 MHz, DMSO-d6) δ 2.08 (multiple overlapping with s, 4H), 2.09 (s, 3H), 2.27-2.33 (m, 1H), 3.40 (dd, J=10.2, 3.6 Hz, 1H), 3.45-3.55 (m, 2H), 3.71 (dd, J=10.2, 6.0 Hz, 1H), 4.32-4.38 (m, 1H), 7.63 (d, J=6.0 Hz, 1H), 11.95 (s, 2H). ATR-IR (cm⁻¹) 3305, 3195, 3115, 2876, 2806, 2757, 1673, 1583, 1508, 1464, 1367, 1316, 1252, 1131, 1006, 962, 827, 696, 648, 606. LC-MS (ESI) m/z for $C_{12}H_{16}N_8O_2S_2$ calculated: 368.08, observed [M+H]: 369

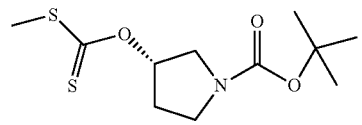 [SMILES: CSC(=S)O[C@H]1CCN(C(=O)OC(C)(C)C)C1]

Intermediate 19 tert-Butyl (3S)-3-{[(methylsulfanyl)methanethioyl]oxy}pyrrolidine-1-carboxylate

To a stirred solution of tert-butyl (S)-3-hydroxypyrrolidine-1-carboxylate (950 mg, 5.074 mmol) in THF (20 ml) was added NaH (244 mg, 6.09 mmol) in portions. This mixture was stirred until the hydrogen evolution subsided and then treated with CS₂ (0.46 ml, 7.61 mmol) and then after 5 min with MeI (0.38 ml, 6.09 mmol). The reaction was stirred at room temperature until TLC indicated consumption of the starting material and then partitioned between CH₂Cl₂ and water. The water layer was extracted with CH₂Cl₂ twice more and then the combined organic layer was evaporated to a residue that was chromatographed with column and 0-20% ethyl acetate in hexanes gradient to yield the product, tert-butyl (3S)-3-{[(methylsulfanyl) methanethioyl]oxy}pyrrolidine-1-carboxylate, as a colorless oil (1.29 g, 92% yield). 1H NMR (600 MHz, CDCl₃) δ 1.47 (s, 9H), 2.11-2.20 (m, 1H), 2.21-2.25 (m, 1H), 2.56 (s, 3H), 3.38-3.51 (m, 1H), 3.52-3.73 (m, 3H), 5.97 (apparent s, 1H). LC-MS (ESI) m/z for $C_{11}H_{19}NO_3S_2$ calculated: 277.08, observed [M+Na]: 300.

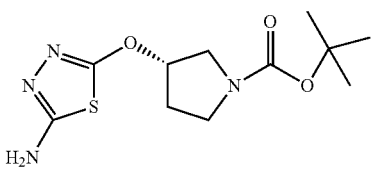 [SMILES: CC(C)(C)OC(=O)N1CC[C@H](Oc2nnc(N)s2)C1]

Intermediate 20 tert-Butyl (S)-3-((5-amino-1,3,4-thiadiazol-2-yl)oxy)pyrrolidine-1-carboxylate

To a stirred solution of tert-butyl (3S)-3-{[(methylsulfanyl)methanethioyl]oxy}pyrrolidine-1-carboxylate (1.29 g, 4.65 mmol) in anhydrous MeOH (15 ml) was added hydrazine (0.22 ml, 6.98 mmol). The reaction was stirred at room temperature for 30 minutes. MeOH was evaporated and the residue was placed under high vacuum for 1 h. The residue was then dissolved in anhydrous MeOH (15 ml), added Et₃N (1.25 ml, 9.12 mmol) and then followed dropwise addition of a solution of BrCN (580 mg, 5.47 mmol) in anhydrous MeOH (15 ml). The reaction was stirred at room temperature overnight and then the reaction mixture was concentrated to a residue that was chromatographed with a 0-5% methanol in ethyl acetate gradient to afford the product, tert-butyl (S)-3-((5-amino-1,3,4-thiadiazol-2-yl)oxy)pyrrolidine-1-carboxylate as an off white solid (379 mg, 28% yield). 1H NMR (600 MHz, DMSO-d₆) δ 1.40 (s, 9H), 2.09-2.18 (m, 2H), 3.24-3.57 (m, 4H), 5.28 (apparent s, 1H), 6.79 (s, 2H). LC-MS (ESI) m/z for $C_{11}H_{18}N_4O_3S$ calculated: 286.11, observed [M+H]: 287.

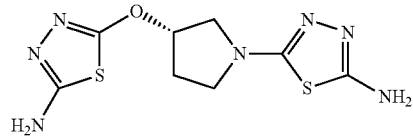 [SMILES: Nc1nnc(O[C@H]2CCN(c3nnc(N)s3)C2)s1]

Example 26

(S)-5-(3-((5-amino-1,3,4-thiadiazol-2-yl)oxy)pyrrolidin-1-yl)-1,3,4-thiadiazol-2-amine (UPGL00014)

To stirred solution of tert-butyl (S)-3-((5-amino-1,3,4-thiadiazol-2-yl)oxy)pyrrolidine-1-carboxylate (379 mg, 1.32 mmol) in CH₂Cl₂ (7 ml) is added TFA (3 ml) and the reaction was stirred until TLC indicated complete consumption of starting material. Excess solid K₂CO₃ was then added to reaction mixture and the suspension formed was stirred for thirty minutes. Reaction mixture was then treated with acetonitrile, filtered and the solids were washed with acetonitrile until there was no UV absorption detected in the wash stream. Organic layer was then evaporated and the residue dissolved in ethanol (7 mL) and treated with NaHCO$_3$ (333 mg, 3.97 mmol) and 2-amino-5-bromo-thiadiazole (262 mg, 1.46 mmol). The reaction was stirred at 80° C. overnight, then cooled and filtered. Solids were then washed with two portions of EtOH (approx. 5 mL) and combined organic layer was evaporated. The residue was washed with water, triturated with boiling MeOH, EtOAc and then dried to yield (S)-5-(3-((5-amino-1,3,4-thiadiazol-2-yl)oxy)pyrrolidin-1-yl)-1,3,4-thiadiazol-2-amine (25 mg, 6% yield) as an off-white tan solid. 1H NMR (600 MHz, DMSO-d$_6$) δ 2.21-2.35 (m, 2H), 3.38-3.44 (m, 2H), 3.53 (d, J=12.0 Hz, 1H), 3.66 (dd, J=11.4, 4.8 Hz, 1H), 5.38-5.43 (m, 1H), 6.37 (s, 2H), 6.80 (s, 2H). ATR IR (cm$^{-1}$) 3275, 3106, 1626, 1577, 1545, 1498, 1474, 1383, 1347, 1315, 1285, 1253, 1239, 1106, 1066, 1025, 890, 852, 754, 689, 618. LC-MS (ESI) m/z for C$_8$H$_{11}$N$_4$OS calculated: 285.05, observed [M−H]284.

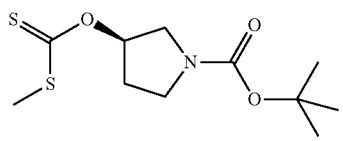 [SMILES: CSC(=S)O[C@@H]1CCN(C(=O)OC(C)(C)C)C1]

Intermediate 21 tert-Butyl (3R)-3-{[(methylsulfanyl)methanethioyl]oxy}pyrrolidine-1-carboxylate

To a stirred solution of tert-butyl (R)-3-hydroxypyrrolidine-1-carboxylate (1.10 g, 5.85 mmol) in anhydrous THF (20 ml) under nitrogen was added NaH (668 mg, 3.46 mmol) portion-wise. The mixture was stirred for 20 minutes and then treated with CS$_2$ (0.53 ml, 8.77 mmol). 5 min later followed dropwise addition of MeI (0.44 ml, 7.02 mmol). The mixture was stirred at room temperature until TLC indicated consumption of the starting material and then partitioned between CH$_2$Cl$_2$ and water. The water layer was extracted twice more with CH$_2$Cl$_2$ and the combined organic layer was dried over Na$_2$SO$_4$ filtered and evaporated to a residue that was chromatographed with a 0-20% ethyl acetate in hexanes gradient to yield the product, tert-butyl (3R)-3-{[(methylsulfanyl)methanethioyl]oxy}pyrrolidine-1-carboxylate, as a yellowish oil (1.43 g, 94% yield). 1HNMR (600 MHz CDC$_3$) δ=1.46 (s, 9H) 2.11-2.21 (m, 1H), 2.22-2.28 (m, 1H), 2.56 (s, 3H), 3.40-3.51 (m, 1H), 3.52-3.73 (m, 3H), 5.96 (apparent s, 1H). LC-MS (ESI) m/z C$_{11}$H$_{19}$NO$_3$S$_2$ calculated: 277.08, observed [M+Na]: 300.

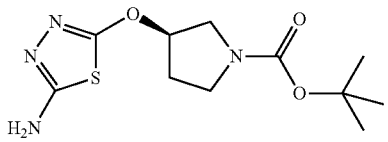 [SMILES: CC(C)(C)OC(=O)N1CC[C@@H](Oc2nnc(N)s2)C1]

Intermediate 22 tert-Butyl (R)-3-((5-amino-1,3,4-thiadiazol-2-yl)oxy)pyrrolidine-1-carboxylate

To a stirred solution of tert-butyl (3R)-3-{[(methylsulfanyl)methanethioyl]oxy}pyrrolidine-1-carboxylate (1.43 g, 5.14 mmol) in anhydrous MeOH (14 ml) is added hydrazine (0.24 ml, 7.71 mmol) at room temperature. The mixture is stirred for 30 minutes and then evaporated. The residue was dissolved in MeOH (approx. 5 mL) and the resulting solution was evaporated again. After repeating this dissolution in MeOH and evaporation cycle two more times the residue was taken in MeOH (20 ml) and the resulting solution was cooled to 0° C., and treated with Et$_3$N (1.43 mL, 10.28 mmol) and BrCN (653 mg, 6.17 mmol). The reaction mixture was allowed to gradually reach room temperature and stirred until TLC indicated consumption of the starting material. The reaction solvent was then evaporated and the residue is partitioned between EtOAc and water. The water layer was extracted with EtOAc twice more and the combined organic layer was dried over Na$_2$SO$_4$ filtered and evaporated to yield a residue was dissolved in a minimum amount of chloroform and precipitated with hexanes, the solid is filtered and dried to yield tert-butyl (R)-3-((5-amino-1,3,4-thiadiazol-2-yl)oxy)pyrrolidine-1-carboxylate, as an off-white solid (703 mg, 48% yield). 1H NMR, 600 MHz, CDCl$_3$, δ=1.46 (s, 9H), 2.09-2.19 (m, 1H), 2.26-2.35 (s, 1H), 3.40-3.79 (m, 4H), 4.63 (s, 2H), 5.49 (apparent s, 1H). LC-MS (ESI) m/z C$_{11}$H$_{18}$N$_4$O$_3$S calculated: 286.35, observed [M−H]: 285.

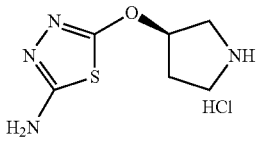

Intermediate 23

5-[(3R)-pyrrolidin-3-yloxy]-1,3,4-thiadiazol-2-amine Hydrochloride

To tert-butyl (R)-3-((5-amino-1,3,4-thiadiazol-2-yl)oxy)pyrrolidine-1-carboxylate (703 mg, 2.45 mmol) in dioxane (approx. 5 mL) was added 4M HCl in dioxane (1.23 ml, 4.91 mmol). The reaction was stirred until TLC showed consumption of starting material and then evaporated to dryness under a stream of nitrogen. The residue was triturated with boiling hexane and CH$_2$Cl$_2$ to yield the product, 5-[(3R)-pyrrolidin-3-yloxy]-1,3,4-thiadiazol-2-amine hydrochloride, as an off-white solid (595 mg, 54% yield). 1H NMR (600 MHz, DMSO-d6), δ=2.18-2.28 (m, 2H), 3.20-3.27 (m, 1H), 3.27-3.36 (m, 1H), 3.42-3.52 (m, 2H), 5.44 (apparent s, 1H), 8.32 (broad s, 2H), 9.51 (s, 1H), 9.56 (s, 1H). ATR IR (cm$^{-1}$), 3223, 2905, 2635, 2589, 1636, 1583, 1560, 1427, 1397, 1369, 1274, 1191, 1131, 1083, 1048, 1026, 948, 896, 857, 796, 741, 691, 669, 635. LC-MS (ESI) m/z for free base C$_6$H$_{10}$N$_4$OS calculated: 186.06, observed [M+H]: 187.

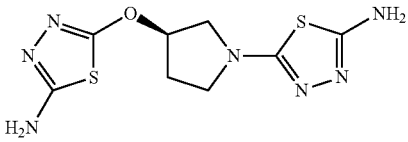 [SMILES: Nc1nnc(O[C@@H]2CCN(c3nnc(N)s3)C2)s1]

Example 27

5-[(3R)-3-[(5-amino-1,3,4-thiadiazol-2-yl)oxy]pyrrolidin-1-yl]-1,3,4-thiadiazol-2-amine (UPGL00026)

To a stirred solution of 5-[(3R)-pyrrolidin-3-yloxy]-1,3,4-thiadiazol-2-amine hydrochloride (595 mg, 1.07 mmol) in EtOH (16 ml) was added 2-amino-5-bromo-thiadiazole (632 mg, 3.51 mmol) and Et$_3$N (1.70 ml, 12.78 mmol) and the reaction was stirred at 77° C. overnight. The reaction mixture was then cooled and evaporated to a residue that was washed with water and triturated in sequence first with boiling MeOH, then boiling DCM, and then boiling hexanes to yield the product, 5-[(3R)-3-[(5-amino-1,3,4-thiadiazol-2-yl)oxy]pyrrolidin-1-yl]-1,3,4-thiadiazol-2-amine (UPGL00026) as an off-white/tan solid (144 mg, 47% yield). 1H NMR (600 MHz, DMSO-d6) δ 2.21-2.26 (m, 1H), 2.28-2.35 (m, 1H), 3.37-3.44 (m, 2H), 3.51-3.55 (m, 1H), 3.63-3.68 (m, 1H), 5.39 (apparent s, 1H), 6.37 (s, 2H), 6.80 (s, 2H). ATR IR (cm$^{-1}$), 3270, 3103, 1626, 1577, 1543, 1503, 1469, 1346, 1286, 1238, 1107, 1064, 688. LC-MS (ESI) m/z for C$_8$H$_{11}$N$_7$OS$_2$ calculated: 285.05, observed [M−H]: 284.

Example 28

2-phenyl-N-(5-{[(3R)-1-[5-(2-phenylacetamido)-1,3,4-thiadiazol-2-yl]pyrrolidin-3-yl]oxy}-1,3,4-thiadiazol-2-yl)acetamide (UPGL00027)

To a stirred solution of 5-[(3R)-3-[(5-amino-1,3,4-thiadiazol-2-yl)oxy]pyrrolidin-1-yl]-1,3,4-thiadiazol-2-amine (UPGL00026) (50 mg, 0.18 mmol) in DMF (2.5 ml) was added Et$_3$N (0.07 ml, 0.53 mmol) and phenylacetyl chloride (0.045 ml, 0.35 mmol). The mixture was stirred at room temperature until TLC indicated consumption of starting material and then evaporated to a residue that was washed with water and the sequentially triturated with hot EtOH, then CH$_2$Cl$_2$ and then hexanes to yield the product, 2-phenyl-N-(5-{[(3R)-1-[5-(2-phenylacetamido)-1,3,4-thiadiazol-2-yl]pyrrolidin-3-yl]oxy}-1,3,4-thiadiazol-2-yl)acetamide (UPGL00027) as an off-white solid (24 mg, 26% yield). 1HNMR (600 MHz, DMSO-d6) δ 2.31-2.40 (m, 2H), 3.48-3.56 (m, 2H), 3.69 (d, J=12.0 Hz, 1H), 3.72 (s, 2H), 3.76 (s, 2H), 3.80 (dd, 1H, J=4.8, 12.0 Hz), 7.23-7.34 (m, 10H), 12.28 (s, 1H) 12.60 (s, 1H). ATR IR (cm$^{-1}$), 3174, 3059, 3030, 2870, 1685, 1673, 1530, 1496, 1454, 1360, 1298, 1256, 1198, 1147, 1079, 1028, 958, 957, 798, 757, 714, 694, 641. LC-MS (ESI) m/z for C$_{24}$H$_{23}$N$_7$O$_3$S$_2$ calculated: 521.13, observed [M+H]: 522.

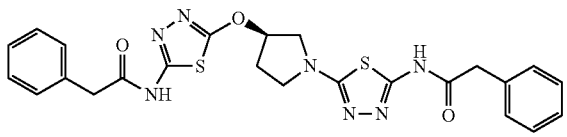 [SMILES: O=C(Cc1ccccc1)Nc1nnc(O[C@@H]2CCN(c3nnc(NC(=O)Cc4ccccc4)s3)C2)s1]

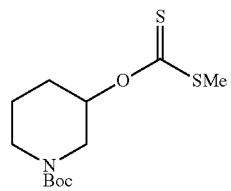 [SMILES: CSC(=S)OC1CCCN(C(=O)OC(C)(C)C)C1]

Intermediate 24 tert-Butyl 3-(((methylthio)carbonothioyl)oxy)piperidine-1-carboxylate

To a solution of tert-butyl 3-hydroxypiperidine-1-carboxylate (823 mg, 4.09 mmol) in anhydrous THF (15 ml) is added NaH (60% dispersion in oil, 196 mg, 4.91 mmol) portion wise. After 15 min followed addition of CS$_2$ (0.369 mL, 6.134 mmol) and then 5 min later addition of MeI (0.31 mL, 4.91 mmol). The reaction mixture was stirred at room temperature for 48 h and then partitioned between CH$_2$Cl$_2$ and water. Water layer extracted thoroughly with CH$_2$Cl$_2$ and the combined CH$_2$Cl$_2$ layer was evaporated. The residue was chromatographed on a silica gel column with a 0-20% EtOAc gradient to afford the product, tert-butyl 3-(((methylthio) carbonothioyl)oxy) piperidine-1-carboxylate as a colorless oil (897 mg, 75% yield). $^1$HNMR (600 MHz, CDCl$_3$) δ 1.44 (s, 9H), 1.56 (s, brd, 1H), 1.81 (s, brd, 1H), 1.93 (s, brd, 2H), 2.53 (s, 3H), 3.18 (s, brd, 1H), 3.46 (s, brd, 1H), 3.71 (s, brd, 1H), 3.92 (s, brd, 1H), 5.53 (s, brd, 1H). LC-MS (ESI) m/z for C$_{12}$H$_{21}$NO$_3$S$_2$ calculated: 291.1, observed [M+Na]: 314.

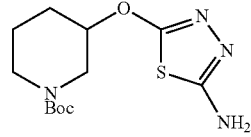 [SMILES: CC(C)(C)OC(=O)N1CCCC(Oc2nnc(N)s2)C1]

Intermediate 25 tert-Butyl 3-((5-amino-1,3,4-thiadiazol-2-yl)oxy)piperidine-1-carboxylate

A solution of tert-butyl 3-(((methylthio)carbonothioyl)oxy)piperidine-1-carboxylate (897 mg 3.07 mmol), in MeOH (10 mL) was treated with anhydrous NH$_2$NH$_2$ (0.15 mL, 4.62 mmol). When the xanthate starting material was consumed, as indicated by TLC, the reaction solvent was evaporated. The residue was re-dissolved in 10 ml of MeOH and the solution was evaporated again. After repeating this methanol dissolution and evaporation process one more time, the residue in MeOH (10 mL) was treated with Et$_3$N (0.858 mL, 6.15 mmol) and solid BrCN (391 mg, 3.69 mmol). After stirring for 18 h at room temperature the solvent was evaporated and the residue was partitioned between EtOAc and water. The organic layer was then collected and evaporated and the residue chromatographed on a silica gel column with 0-40% acetone in CH$_2$Cl$_2$ to afford the product, tert-butyl 3-((5-amino-1,3,4-thiadiazol-2-yl)oxy)piperidine-1-carboxylate, as a white powder (472 mg, 51% yield). $^1$H NMR (600 MHz, DMSO-d$_6$) δ 1.30 (s, brd, 9H), 1.42-1.44 (m, 2H), 1.65 (s, brd, 1H), 1.87 (s, brd, 2H), 2.93 (s, brd, 1H), 3.69 (s, brd, 1H), 4.09 (s, brd, 1H), 4.77 (m, 1H), 6.74 (s, 2H). ATR-IR (cm$^{-1}$) 3326, 3275, 3129, 2953, 2863, 1682, 1623, 1542, 1488, 1422, 1366, 1345, 1277, 1236, 1167, 1150, 1130, 1097, 1073, 1003, 956, 925, 884, 854, 816, 766, 687. LC-MS (ESI) m/z for C$_{12}$H$_{20}$N$_4$O$_3$S calculated: 300.13, observed [M+Na]: 323

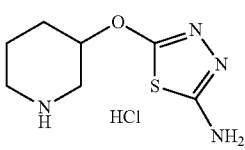

Intermediate 26

5-(piperidin-3-yloxy)-1,3,4-thiadiazol-2-amine Hydrochloride

To tert-butyl 3-((5-amino-1,3,4-thiadiazol-2-yl)oxy)piperidine-1-carboxylate (454 mg, 1.51 mmol) in dioxane (5 mL) was added a solution of 4M HCl in dioxane (9.1 ml, 4.53 mmol). The reaction mixture was stirred until TLC showed consumption of the starting material and then evaporated to dryness under a stream of nitrogen. The solid residue was triturated with boiling $CH_2Cl_2$ then hexanes and then dried to yield the product, 5-(piperidin-3-yloxy)-1,3,4-thiadiazol-2-amine hydrochloride, as a white solid (294 mg, 82% yield). $^1$HNMR (600 MHz, DMSO-$d_6$) 1.69-1.71 (m, 1H), 1.82-1.89 (m, 1H), 1.91-1.99 (m, 2H), 2.90-3.00 (m, 1H), 3.07-3.12 (m, 1H), 3.29-3.36 (m, 2H), 5.11 (s, 1H), 8.53 (s, brd, 2H), 9.00 (s, brd, 1H), 9.54 (s, brd, 1H). ATR-IR (cm$^{-1}$) 3242, 3100, 2958, 2849, 2736, 2496, 2376, 1617, 1569, 1553, 1408, 1361, 1337, 1273, 1198, 1150, 1094, 1053, 1031, 972, 934, 901, 872, 841, 797, 745, 706, 630.

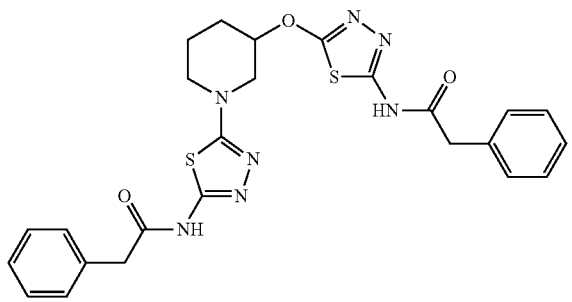 [SMILES: O=C(Cc1ccccc1)Nc1nnc(OC2CCCN(c3nnc(NC(=O)Cc4ccccc4)s3)C2)s1]

Example 29

2-Phenyl-N-(5-(3-((5-(2-phenylacetamido)-1,3,4-thiadiazol-2-yl)oxy)piperidin-1-yl)-1,3,4-thiadiazol-2-yl)acetamide (UPGL00028)

A solution of 5-(piperidin-3-yloxy)-1,3,4-thiadiazol-2-amine hydrochloride (104 mg, 0.44 mmol), 2-amino-5-bromothiadiazole (87 mg, 0.48 mmol) and $Et_3N$ (0.24 mL, 1.76 mmol) in EtOH (3 mL) was heated at 80° C. in a sealed vessel for 48 hrs. The reaction mixture was then cooled and EtOH was evaporated. The solid residue obtained was purified via chromatography and a 0-25% MeOH in $CH_2Cl_2$ to afford the intermediate bis-thiadiazole product as a solid (53 mg). This intermediate without further delay was taken up in DMF (1 mL). The mixture was then treated with $Et_3N$ (0.10 mL, 0.71 mmol) and phenylacetyl chloride (0.06 mL, 0.44 mmol) and the reaction mixture allowed to stir at room temperature until TLC indicated complete consumption of the starting material. Water was then added to the reaction mixture and the solid that precipitated was filtered, washed thoroughly with water dried and chromatographed with a 0-10% MeOH in $CH_2Cl_2$ gradient to afford the product, 2-phenyl-N-(5-(3-((5-(2-phenylacetamido)-1,3,4-thiadiazol-2-yl)oxy)piperidin-1-yl)-1,3,4-thiadiazol-2-yl)acetamide as an off-white solid (54 mg, 57% yield). $^1$H NMR (600 MHz, DMSO-$d_6$) 1.59-1.66 (m, 1H), 1.81-1.88 (m, 1H), 1.90-1.96 (m, 1H), 1.99-2.06 (m, 1H), 3.46-3.51 (m, 1H), 3.71 (s, 2H), 3.76 (s, 2H), 3.66-3.80 (m, 3H), 5.01-5.05 (m, 1H), 7.25-7.34 (m, 10H), 12.28 (s, brd, 1H), 12.57 (s, brd, 1H). ATR-IR (cm$^{-1}$) 3177, 3063, 3029, 2850, 2752, 1684, 1574, 1503, 1454, 1355, 1315, 1252, 1199, 1142, 1073, 1008, 968, 927, 857, 807, 758, 716, 693, 660. LC-MS (ESI) m/z for $C_{25}H_{25}N_7O_3S_2$ calculated: 535.15, observed [M+H]: 536.

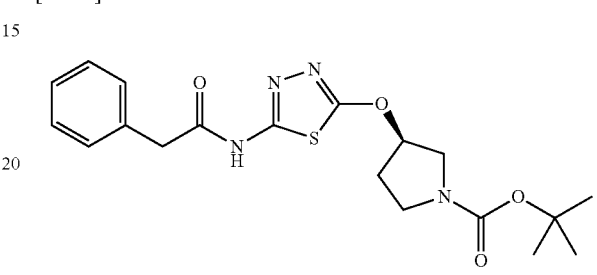

Intermediate 27 tert-Butyl (3R)-3-{[5-(2-phenylacetamido)-1,3,4-thiadiazol-2-yl]oxy}pyrrolidine-1-carboxylate To a stirred solution of tert-butyl (R)-3-((5-amino-1,3,4-thiadiazol-2-yl)oxy)pyrrolidine-1-carboxylate (100 mg, 0.35 mmol) in $CH_2Cl_2$ (2.5 ml) is added $Et_3N$ (0.10 mL, 0.71 mmol) and phenylacetyl chloride (0.06 mL, 0.45 mmol). The reaction mixture was stirred at room temperature until TLC indicated consumption of the starting material and then partitioned between $CH_2Cl_2$ and water. The water layer was extracted twice more with $CH_2Cl_2$ and the combined organic layer was dried over $Na_2SO_4$, filtered and concentrated. The residue was chromatographed with a 0-100% EtOAc/hexanes gradient to afford the product, tert-butyl (3R)-3-{[5-(2-phenylacetamido)-1,3,4-thiadiazol-2-yl]oxy}pyrrolidine-1-carboxylate, as an off-white (100 mg. 71% yield). 1H NMR (600 MHz, CDCl$_3$) δ 1.46 (d, J=10.8 Hz, 9H), 2.10-2.19 (brd m, 1H), 2.28-2.45 (brd m, 1H) 3.46-3.82 (m, 4H), 3.98 (s, 2H), 5.52 (s, 1H) 7.31 (distorted triplet, 1H), 7.36 (t, J=7.2, 2H), 7.43 (d, J=7.8, 2H). LC-MS (ESI) m/z for $C_{19}H_{24}N_4O_4S$ calculated: 404.15, observed [M−H]: 403.

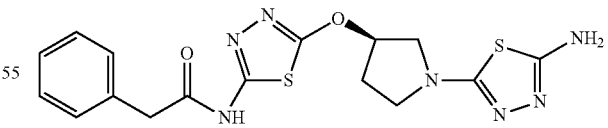

Example 30

N-(5-{[(3R)-1-(5-amino-1,3,4-thiadiazol-2-yl)pyrrolidin-3-yl]oxy}-1,3,4-thiadiazol-2-yl)-2-phenylacetamide (UPGL00029)

tert-Butyl (3R)-3-{[5-(2-phenylacetamido)-1,3,4-thiadiazol-2-yl]oxy}pyrrolidine-1-carboxylate (91 mg, 0.22 mmol) in dioxane (0.10 mL) was treated with 4M HCl in dioxane (total of 0.21 mL, 0.84 mmol). The mixture was stirred at room temperature for 4 h. concentrated under a stream of nitrogen and then washed with hexanes and dried to yield the corresponding deprotected intermediate hydrochloride as a white solid (65 mg, 0.19 mmol, 87% yield).

LC-MS (ESI) m/z for free base $C_{14}H_{16}N_4O_2S$ calculated: 304.10, observed [M+H]: 305.

This intermediate without further delay was dissolved in EtOH (0.5 mL). Followed addition of $Et_3N$ (0.11 mL, 0.76 mmol) and 2-amino-5-bromothiadiazole (38 mg, 0.21 mmol) and the mixture was stirred at 76° C. in a sealed vessel until TLC indicated consumption of the limiting reagent. The mixture was then cooled and evaporated. The solid residue was washed with water, dried and chromatographed with 0-10% $MeOH/CH_2Cl_2$ gradient to yield the product, N-(5-{[(3R)-1-(5-amino-1,3,4-thiadiazol-2-yl)pyrrolidin-3-yl]oxy}-1,3,4-thiadiazol-2-yl)-2-phenylacetamide (UPGL00029), as an off-white solid (30 mg, 40% yield). 1HNMR (600 MHz, DMSO-$d_6$) δ 2.25-2.31 (m, 1H), 2.32-2.39 (m, 1H), 3.43 (dd, J=9.0, 4.8 Hz, 2H), 3.58 (d, J=12.0 Hz, 1H), 3.71 (dd, J=12.0, 4.8 Hz, 1H), 3.76 (s, 2H), 5.54 (apparent s, 1H), 6.37 (s, 2H), 7.22-7.35 (m, 5H), 12.60 (s, 1H). ATR IR (cm$^{-1}$) 3397, 3271, 3160, 3030, 2918, 2848, 2650, 1664, 1564, 1504, 1470, 1366, 1351, 1331, 1313, 1284, 1252, 1190, 1096, 1078, 1031, 985, 949, 917, 850, 790, 752, 727, 714, 692, 644, 609. LC-MS (ESI) m/z for $C_{16}H_{17}N_7O_2S_2$ calculated: 403.09, observed [M−H]: 402.

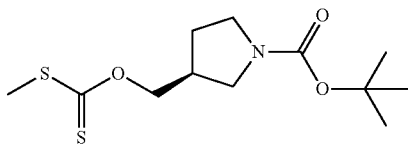 [SMILES: CSC(=S)OC[C@H]1CCN(C(=O)OC(C)(C)C)C1]

Intermediate 28 tert-Butyl (3S)-3-({[(methylsulfanyl)methanethioyl]oxy}methyl)pyrrolidine-1-carboxylate To a stirred solution of commercially available tert-butyl (S)-3-(hydroxymethyl)pyrrolidine-1-carboxylate (580 mg, 2.88 mmol) in anhydrous THF (20 ml) under nitrogen was added NaH (83 mg, 3.46 mmol) in portions. After 20 minutes followed dropwise addition of CS2 (0.26 ml, 4.33 mmol) and then 5 min later dropwise addition of MeI (0.22 ml, 3.46 mmol). The mixture was stirred at room temperature overnight and then partitioned between EtOAc and water. The water layer was extracted with EtOAc two more times and the combined organic layer was dried over $Na_2SO_4$, filtered and concentrated. The residue was purified with a 0-20% ethyl acetate in hexanes gradient to yield the product, tert-butyl (3S)-3-({[(methylsulfanyl)methanethioyl]oxy}methyl) pyrrolidine-1-carboxylate, as a light yellow/brown oil (590 mg, 70% yield). 1HNMR (600 MHz CDCl$_3$) δ 1.47 (s, 9H), 1.69-1.79 (m, 1H), 2.05 (m, 1H), 2.57 (d, 3H, J=8.4 Hz), 2.66-2.76 (m, 1H), 3.09-3.22 (m, 1H), 3.30-3.63 (m, 3H), 4.45-4.54 (m, 1H), 4.55-4.63 (m, 1H). ATR IR (cm$^{-1}$) 2972, 2876, 1687, 1477, 1453, 1400, 1363, 1212, 1166, 1130, 1058, 965, 921, 882, 770.

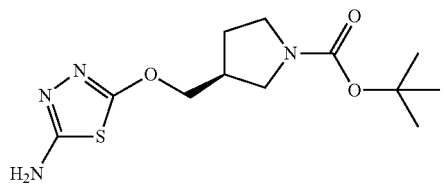

Intermediate 29 tert-Butyl (3S)-3-{[(5-amino-1,3,4-thiadiazol-2-yl)oxy]methyl}pyrrolidine-1-carboxylate To a stirred solution of tert-butyl (3S)-3-({[(methylsulfanyl)methanethioyl]oxy}methyl)-pyrrolidine-1-carboxylate (590 mg, 2.03 mmol) in anhydrous MeOH (20 ml) is added hydrazine (0.10 ml, 3.04 mmol) and the mixture was stirred for 30 minutes. The solvent was then evaporated, and the residue was redissolved in MeOH (approx. 5 mL) and the mixture was evaporated again. This MeOH dilution and evaporation sequence was repeated two more times and then the residue in MeOH (30 ml) was treated with $Et_3N$ (0.56 ml, 4.04 mmol). Followed cooling to 0° C. and then dropwise addition of 3M BrCN in $CH_2Cl_2$ solution (0.81 ml, 2.43 mmol). This mixture was allowed to gradually warm up to room temperature and stirred until consumption of the starting material was observed by TLC. Followed evaporation of the volatiles and the resulting residue was partitioned between EtOAc and water. The water layer was extracted two more times with EtOAc and the combined organic layer was dried over $Na_2SO_4$, filtered and evaporated. The residue obtained was chromatographed with a 0-8% methanol in methylene chloride gradient to yield the product, tert-butyl (3S)-3-{[(5-amino-1,3,4-thiadiazol-2-yl)oxy] methyl}pyrrolidine-1-carboxylate, as an off-white solid (375 mg, 62% yield). 1HNMR (600 MHz CDCl$_3$) δ 1.46 (s, 9H), 1.68-1.79 (m, 1H), 2.00-2.09 (m, 1H), 2.64-2.73 (m, 1H), 3.10-3.25 (m, 1H), 3.30-3.61 (m, 3H), 4.31-4.38 (m, 1H), 4.22 (dd, J=10.2, 6.6 Hz, 1H), 4.66 (s, 2H). ATR IR (cm$^{-1}$) 3328, 3275, 3119, 2974, 1681, 1625, 1549, 1497, 1459, 1412, 1392, 1364, 1331, 1252, 1167, 1136, 1087, 969, 888, 877, 770, 684.

LC-MS (ESI) m/z for $C_{12}H_{20}N_4O_3S$ calculated: 300.13, observed [M−H]: 299.

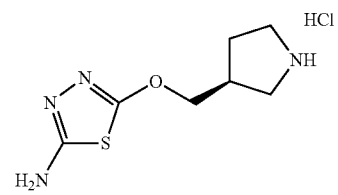 [SMILES: Cl ; Nc1nnc(OC[C@H]2CCNC2)s1]

Intermediate 30

5-[(3S)-pyrrolidin-3-ylmethoxy]-1,3,4-thiadiazol-2-amine Hydrochloride

To a stirred solution tert-butyl (3S)-3-{[(5-amino-1,3,4-thiadiazol-2-yl)oxy]methyl}pyrrolidine-1-carboxylate (180 mg, 0.60 mmol) in 1 mL of dioxane was added a solution of 4M HCl in dioxane (0.32 ml, 1.26 mmol). The mixture was stirred at room temperature until TLC indicated consumption of starting material and then evaporated to dryness under a stream of N₂. The solid obtained was triturated with boiling hexanes and then CH₂Cl₂ to yield the product, 5-[(3S)-pyrrolidin-3-ylmethoxy]-1,3,4-thiadiazol-2-amine hydrochloride, as an off-white solid (141 mg, 100% yield). 1H NMR (600 MHz DMSO-d6) δ=1.71-1.77 (m, 1H), 2.02-2.13 (m, 1H), 2.72-2.79 (m, 1H), 2.97-3.05 (m, 1H), 3.10-3.18 (m, 1H), 3.20-32 (m, 2H), 4.35-4.42 (m, 2H), 8.65 (brd s, 2H), 9.37 (s, 2H). ATR IR (cm⁻¹) 3297, 2914, 2751, 2590, 2477, 1646, 1562, 1455, 1421, 1390, 1364, 1278, 1249, 1116, 1082, 1047, 952, 923, 891, 868, 780, 740, 700, 638, 615. LC-MS (ESI) m/z for the free base C₇H₁₂N₄OS calculated: 200.07, observed [M+H]: 201.

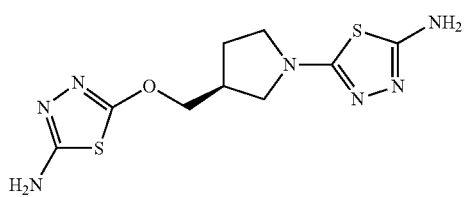 [SMILES: Nc1nnc(OC[C@H]2CCN(c3nnc(N)s3)C2)s1]

Example 31

5-[(3S)-3-{[(5-Amino-1,3,4-thiadiazol-2-yl)oxy]methyl}pyrrolidin-1-yl]-1,3,4-thiadiazol-2-amine (UPGL00032)

A solution of 5-[(3S)-pyrrolidin-3-ylmethoxy]-1,3,4-thiadiazol-2-amine hydrochloride (141 mg, 0.60 mmol) was added 2-amino-5-bromothiadiazole (119 mg, 0.66 mmol) and Et₃N (0.32 ml, 2.40 mmol) in EtOH (1 ml) was stirred at 77° C. in a sealed vessel until TLC indicated consumption of starting material. The mixture was then cooled and evaporated under a stream of nitrogen to afford a solid. This solid was washed with water, triturated with boiling EtOH, dried and chromatographed with a 0-25% methanol in methylene chloride gradient to yield the product, 5-[(3S)-3-{[(5-amino-1,3,4-thiadiazol-2-yl)oxy]methyl}pyrrolidin-1-yl]-1,3,4-thiadiazol-2-amine (UPGL00032), as an off-white/tan solid (91 mg, 50% yield). 1H NMR (600 MHz DMSO-d6) δ 1.78-1.85 (m, 1H), 2.06-2.14 (m, 1H), 2.73-2.82 (m, 1H), 3.13 (dd, J=9.6, 6.6 Hz, 1H), 3.34-3.42 (m, 1H), 3.45 (dd, J=9.6, 7.8, 1H), 4.25-4.36 (m, 2H), 6.31 (s, 2H), 6.75 (s, 2H). ATR IR (cm⁻¹) 3251, 3099, 2931, 1614, 1567, 1503, 1469, 1398, 1298, 1270, 1255, 1061, 1033, 1006, 989, 747, 682, 626. LC-MS (ESI) m/z for C₉H₁₃N₇OS₂ calculated: 299.06, observed: 300.

Example 32

2-Phenyl-N-{5-[(3S)-3-({[5-(2-phenylacetamido)-1,3,4-thiadiazol-2-yl]oxy}methyl)pyrrolidin-1-yl]-1,3,4-thiadiazol-2-yl}acetamide (UPGL00033)

To a stirred solution of 5-[(3S)-3-{[(5-amino-1,3,4-thiadiazol-2-yl)oxy]methyl}pyrrolidin-1-yl]-1,3,4-thiadiazol-2-amine (UPGL00032) (66 mg, 0.22 mmol) in DMF (0.5 ml) was added Et₃N (0.13 mL 0.90 mmol) and phenylacetyl chloride (0.09 mL, 0.67 mmol) at room temperature. The mixture was stirred until TLC indicated consumption of the limiting reagent and then evaporated to a residue that was washed with water, triturated sequentially with boiling CH₂Cl₂, then EtOAc and then hexanes to yield the product, 2-phenyl-N-{5-[(3S)-3-({[5-(2-phenylacetamido)-1,3,4-thiadiazol-2-yl]oxy}methyl)pyrrolidin-1-yl]-1,3,4-thiadiazol-2-yl}acetamide (UPGL00033), as an off-white solid (46 mg, 39% yield). 1HNMR (600 MHz, DMSO-d6) δ 1.84-1.92 (m, 1H), 2.11-2.19 (m, 1H), 2.83-2.92 (m, 1H), 3.24 (dd, J=9.6, 6.6 Hz, 1H), 3.38-3.43 (m, 1H), 3.47-3.52 (m, 1H), 3.56 (dd, J=9.6, 7.8 Hz, 1H), 3.72 (s, 2H), 3.76 (s, 2H), 4.41-4.49 (m, 2H), 7.23-7.36 (m, 10H) 12.24 (s, 1H), 12.56 (s, 1H). ATR IR (cm⁻¹) 3176, 3063, 3030, 2866, 1686, 1575, 1505, 1454, 1394, 1358, 1294, 1268, 1162, 1074, 1031, 968, 812, 753, 720, 694, 646. LC-MS (ESI) m/z for C₂₃H₂₅N₇OS₂ calculated: 535.15, observed [M+H]: 536.

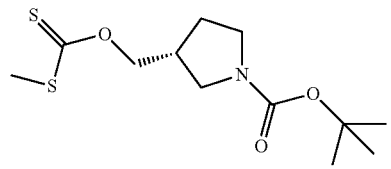

Intermediate 31 tert-Butyl (3R)-3-({[(methylsulfanyl)methanethioyl]oxy}methyl)pyrrolidine-1-carboxylate To a stirred solution of commercially available tert-butyl (R)-3-(hydroxymethyl)pyrrolidine-1-carboxylate (612 mg, 3.45 mmol) in anhydrous THF (40 ml) under nitrogen was added NaH (87.5 mg, 3.65 mmol) in portions. After 20 minutes followed dropwise addition of CS₂ (0.28 ml, 4.56 mmol) and then 5 min later dropwise addition of MeI (0.23 ml, 3.45 mmol). The mixture was stirred at room temperature overnight and then partitioned between EtOAc and water. The water layer was extracted with EtOAc two more times and the combined organic layer was dried over Na₂SO₄, filtered and concentrated. The residue was purified with a 0-20% ethyl acetate in hexanes gradient to yield the product, tert-butyl (3R)-3-({[(methylsulfanyl)meth-

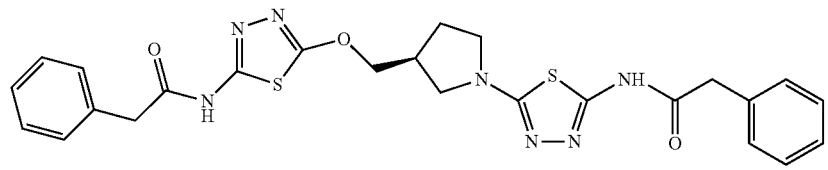 [SMILES: O=C(Cc1ccccc1)Nc1nnc(OC[C@H]2CCN(c3nnc(NC(=O)Cc4ccccc4)s3)C2)s1]

anethioyl]oxy}methyl)pyrrolidine-1-carboxylate, as a light yellow/brown oil (660 mg, 75% yield). 1HNMR (600 MHz CDCl$_3$) δ 1.47 (s, 9H), 1.68-1.76 (m, 1H), 2.01-2.10 (m, 1), 2.57 (s, 3H), 2.66-2.76 (m, 1H), 3.09-3.22 (m, 1H), 3.28-3.65 (m, 3H), 4.49-4.55 (m, 1H), 4.57-4.2 (m, 1H). ATR IR (cm$^{-1}$) 2972, 2876, 1687, 1477, 1453, 1400, 1363, 1212, 1166, 1130, 1058, 965, 882, 770. LC-MS (ESI) m/z for C$_{12}$H$_{21}$NO$_3$S$_2$ calculated: 291.09, observed [M+Na]: 314.

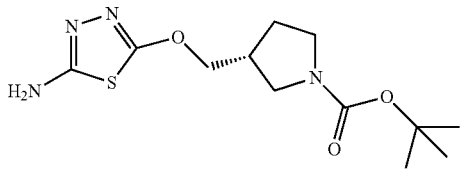 [SMILES: CC(C)(C)OC(=O)N1CC[C@@H](COc2nnc(N)s2)C1]

Intermediate 32 tert-Butyl (3R)-3-{[(5-amino-1,3,4-thiadiazol-2-yl)oxy]methyl}pyrrolidine-1-carboxylate To a stirred solution of tert-butyl (3R)-3-({[(methylsulfanyl)methanethioyl]oxy}methyl)-pyrrolidine-1-carboxylate (652 mg, 2.23 mmol) in anhydrous MeOH (40 ml) is added hydrazine (0.106 ml, 3.36 mmol) and the mixture was stirred for 30 minutes. The solvent was then evaporated, and the residue was redissolved in MeOH (approx. 5 mL) and the mixture was evaporated again. This MeOH dilution and evaporation sequence was repeated two more times and then the residue in MeOH (40 ml) was treated with Et$_3$N (0.625 ml, 4.48 mmol). Followed cooling to 0° C. and then dropwise addition of 3M BrCN in CH$_2$Cl$_2$ solution (0.896 ml, 2.69 mmol). This mixture was allowed to gradually warm up to room temperature and stirred until consumption of the starting material was observed by TLC. Followed evaporation of the volatiles and the resulting residue was partitioned between EtOAc and water. The water layer was extracted two more times with EtOAc and the combined organic layer was dried over Na$_2$SO$_4$, filtered and evaporated. The residue obtained was chromatographed with a 0-5% methanol in methylene chloride gradient to yield the product, tert-butyl (3R)-3-{[(5-amino-1,3,4-thiadiazol-2-yl)oxy]methyl}pyrrolidine-1-carboxylate, as an off-white solid (342 mg, 51% yield). 1-NMR (600 MHz CDCl$_3$) δ 1.43 (s, 9H), 1.68-1.76 (m, 1H), 1.98-2.07 (m, 1H), 2.65-2.73 (m, 1H), 3.10-3.21 (m, 1H), 3.30-3.62 (m, 3H) 4.29-4.33 (m, 1H), 4.41 (dd, J=10.2, 6.6 Hz, 1H), 5.32 (s, 2H). ATR IR (cm$^{-1}$) 3324, 3105, 2970, 2878, 1684, 1623, 1555, 1495, 1459, 1408, 1364, 1256, 1170, 1136, 1113, 992, 962, 939, 885, 772, 687, 605. LC-MS (ESI) m/z for C$_{12}$H$_{20}$N$_4$O$_3$S calculated: 300.13, observed [M+H]: 301.

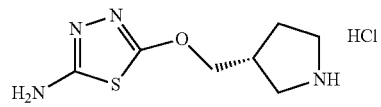 [SMILES: Nc1nnc(OC[C@@H]2CCNC2)s1 ; Cl]

Intermediate 33

5-[(3R)-pyrrolidin-3-ylmethoxy]-1,3,4-thiadiazol-2-amine Hydrochloride tert-Butyl (3R)-3-{[(5-amino-1,3,4-thiadiazol-2-yl)oxy]methyl}pyrrolidine-1-carboxylate (160 mg, 0.53 mmol) in dioxane (1 mL) was treated with 4M HCl in dioxane (total of 0.33 mL, 0.83 mmol), The mixture was stirred at room temperature, until TLC indicated consumption of the starting material and then evaporated to dryness under a stream of nitrogen. The solid was triturated with hot methylene chloride and then boiling hexanes and dried to afford the product, 5-[(3R)-pyrrolidin-3-ylmethoxy]-1,3,4-thiadiazol-2-amine hydrochloride, as an off-white solid (126 mg, 100%). 1H NMR (600 MHz, DMSO-d6) δ 1.71-1.76 (m, 1H), 2.05-2.10 (m, 1H), 2.74-2.78 (m, 1H), 2.98-3.03 (m, 1H), 3.09-3.19 (m, 1H), 3.20-3.33 (m, 2H), 4.33-4.39 (m, 2H), 8.38 (broad s, 2H), 9.30 (s, 2H). ATR IR (cm$^{-1}$) 2902, 2603, 1634, 1584, 1547, 1460, 1390, 1263, 1134, 1050, 963, 938, 911, 805, 738, 691. LC-MS (ESI) m/z for free base C$_7$H$_{12}$N$_4$OS calculated: 200.07, observed [M+H]201.

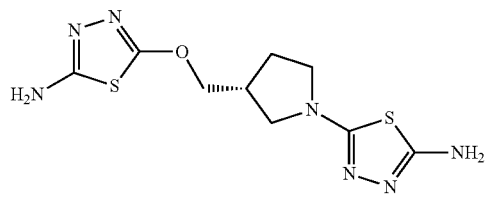 [SMILES: Nc1nnc(OC[C@@H]2CCN(c3nnc(N)s3)C2)s1]

Example 33

5-[(3R)-3-{[(5-amino-1,3,4-thiadiazol-2-yl)oxy]methyl}pyrrolidin-1-yl]-1,3,4-thiadiazol-2-amine (UPGL00036)

5-[(3R)-pyrrolidin-3-ylmethoxy]-1,3,4-thiadiazol-2-amine hydrochloride (120 mg, 0.60 mmol) in DMF (1 mL) was treated with 2-amino-5-bromothiadiazole (118.8 mg, 0.66 mmol) and Et$_3$N (0.33 mL, 2.40 mmol) and the mixture was stirred at 80° C. in a sealed vessel for 18 hr. The mixture was then cooled and evaporated. The solid residue was washed with water triturated sequentially with boiling ethyl acetate then methanol and hexanes and dried to yield the product, 5-[(3R)-3-{[(5-amino-1,3,4-thiadiazol-2-yl)oxy]methyl}pyrrolidin-1-yl]-1,3,4-thiadiazol-2-amine (UPGL00036) as an off-white solid (30 mg, 16% yield). 1HNMR (600 MHz DMSO-d6) δ 1.78-1.85 (m, 1H), 2.06-2.14 (m, 1H), 2.73-2.82 (m, 1H), 3.14 (dd, J=9.6, 6.6 Hz, 1H), 3.28-3.33 (m, 1H), 3.36-3.42 (m, 1H), 3.42-3.49 (dd, J=9.6, 7.8 Hz, 1H), 4.25-4.35 (m, 2H), 6.31 (s, 2H), 6.75 (s, 2H). LC-MS (ESI) m/z for C$_9$H$_{13}$N$_7$OS$_2$ calculated: 299.06, observed [M+H]: 300.

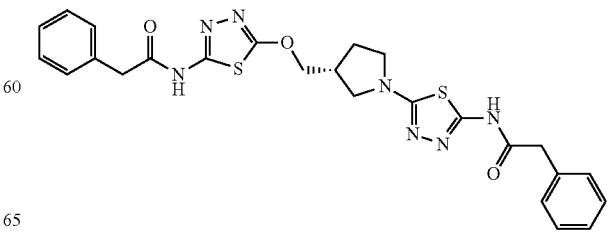

Example 34

2-phenyl-N-{5-[(3R)-3-({[5-(2-phenylacetamido)-1,3,4-thiadiazol-2-yl]oxy}methyl)pyrrolidin-1-yl]-1,3,4-thiadiazol-2-yl}acetamide (UPGL00037)

5-[(3R)-3-{[(5-amino-1,3,4-thiadiazol-2-yl)oxy]methyl}pyrrolidin-1-yl]-1,3,4-thiadiazol-2-amine (UPGL00036) (30 mg, 0.10 mmol) in dry DMF (1 mL) was treated with Et₃N (0.04 mL, 0.31 mmol) and phenylacetyl chloride (0.03 mL, 0.20 mmol) at room temperature. The mixture was stirred at room temperature until TLC indicated consumption of the limiting reagent and then treated with of excess of water. The suspension formed was filtered and the solid was washed with water and then triturated with boiling ethyl acetate, methanol, methylene chloride and then hexanes and dried to afford the product, 2-phenyl-N-{5-[(3R)-3-({[5-(2-phenylacetamido)-1,3,4-thiadiazol-2-yl]oxy}methyl)pyrrolidin-1-yl]-1,3,4-thiadiazol-2-yl}acetamide (UPGL00037) as an off-white solid (20 mg, 37% yield). 1H NMR (600 MHz, DMSO-d6) δ 1.84-1.92 (m, 1H), 2.11-2.19 (m, 1H), 2.83-2.92 (m, 1H), 3.26 (dd, J=9.6, 6.6 Hz, 1H), 3.38-3.43 (m, 1H), 3.47-3.52 (m, 1H), 3.56 (dd, J=9.6, 7.8 Hz, 1H), 3.72 (s, 2H), 3.76 (s, 2H), 4.41-4.49 (m, 2H), 7.23-7.35 (m, 10H), 12.21 (brd s, 1H), 12.55 (brd s, 1H). ATR IR (cm⁻¹) 3178, 2918, 2850, 1685, 1583, 1505, 1452, 1394, 1354, 1253, 1159, 1074, 966, 811, 719, 692, 645. LC-MS (ESI) m/z for $C_{25}H_{25}N_7O_2S_2$ calculated: 535.64, observed [M+H]536.

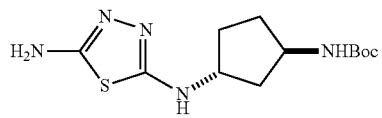

Intermediate 34

(±)-(anti)-3-[(5-Amino-[1,3,4]thiadiazol-2-ylamino)-cyclopentyl]-carbamic Acid tert-butyl Ester

To a stirred solution of (±)-(anti)-(3-amino-cyclopentyl)-carbamic acid tert-butyl ester (prepared as described by Qian Y. et al. in Biorg. Med. Chem. Letter 2013, 23, 4216-4220) (478 mg, 2.38 mmol) in EtOH (12 ml) was added NaHCO₃ (300 mg, 3.57 mmol) and 2-amino-5-bromothiadiazole (515 mg, 2.86 mmol). The mixture was stirred in a sealed vessel at 80° C. until TLC showed consumption of the limiting reagent. The reaction mixture was then cooled and evaporated under a stream of nitrogen to a residue that was then partitioned between EtOAc and water. The water layer was extracted with EtOAc two more times and the combined organic layer was dried over Na₂SO₄ and evaporated. The residue obtained was chromatographed with 0-30% methanol in methylene chloride gradient to yield the product, (±)-(anti)-3-[(5-amino-[1,3,4]thiadiazol-2-ylamino)-cyclopentyl]-carbamic acid tert-butyl ester as an off-white/tan solid (170 mg, 24% yield). 1HNMR (600 MHz, MeOD) δ 1.41 (s, 9H), 1.47-1.54 (m, 2H), 1.85 (apparent t, J=6.6 Hz, 2H), 2.03-2.09 (m, 1H), 2.11-2.19 (m, 1H), 3.95-4.06 (m, 2H). LC-MS (ESI) m/z for $C_{12}H_{21}N_5O_2S$ calculated: 299.14, observed [M+H]: 300.

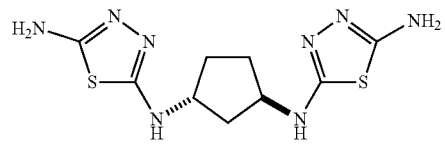 [SMILES: Nc1nnc(N[C@@H]2CC[C@@H](Nc3nnc(N)s3)C2)s1]

Example 35

(±)-(anti)-2-N-[3-[(5-Amino-1,3,4-thiadiazol-2-yl)amino]cyclopentyl]-1,3,4-thiadiazole-2,5-diamine

To a stirred solution of (±)-(anti)-3-[(5-amino-[1,3,4]thiadiazol-2-ylamino)-cyclopentyl]-carbamic acid tert-butyl ester (170 mg, 0.57 mmol) in dichloromethane (7 mL) was treated with trifluoroacetic acid (3 mL) at 0° C. The reaction mixture was then allowed to warm slowly to room temperature stirred for 1 h and then evaporated under vacuo. The residue was then dissolved in EtOH (3 ml). Followed addition of NaHCO₃ (167 mg, 1.98 mmol) and 2-amino-5-bromo-thiadiazole (122 mg, 0.68 mmol). The mixture was stirred in a sealed vessel at 80° C. until consumption of the limiting reagent then cooled and evaporated. The residue was suspended in water then filtered, dried and chromatographed with a 0-20% methanol in methylene chloride gradient to afford the intermediate, (±)-(anti)-2-N-[3-[(5-amino-1,3,4-thiadiazol-2-yl)amino]cyclopentyl]-1,3,4-thiadiazole-2,5-diamine, (91 mg, 54% yield). 1HNMR (600 MHz DMSO-d6) δ 1.41-1.48 (m, 2H), 1.83 (t, J=6.0 Hz, 2H), 2.02-2.08 (m, 2H), 3.91-3.96 (m, 2H), 6.21 (s, 4H), 6.81 (d, J=6.6 Hz, 2H).

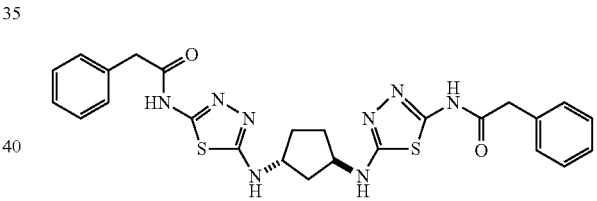

Example 36

(±)-(anti)-2-Phenyl-N-{5-[3-(5-phenylacetylamino-[1,3,4]thiadiazol-2-ylamino)-cyclopentylamino]-[1,3,4]thiadiazol-2-yl}-acetamide (UPGL00010)

To a stirred solution of (±)-(anti)-2-N-[3-[(5-amino-1,3,4-thiadiazol-2-yl)amino]cyclopentyl]-1,3,4-thiadiazole-2,5-diamine (90 mg, 0.30 mmol) in anhydrous DMF (3 ml) was added Et₃N (0.13 ml, 0.91 mmol) and phenylacetyl chloride (0.08 ml, 0.60 mmol). The mixture was stirred at room temperature overnight. Followed slow addition of excess of water. The suspension formed was filtered and the solid was chromatographed with a 0-10% methanol in methylene chloride gradient to yield the product, (±)-(anti)-2-phenyl-N-{5-[3-(5-phenylacetylamino-[1,3,4]thiadiazol-2-ylamino)-cyclopentylamino]-[1,3,4]thiadiazol-2-yl}-acetamide (UPGL00010), as an off white solid (13 mg, 5% yield). 1HNMR (600 MHz, DMSO-d₆) δ 1.47-1.53 (m, 2H), 1.88-1.91 (m, 2H), 2.09-2.20 (m, 2H), 3.70 (s, 4H), 4.05-4.11 (m, 2H), 7.23-7.41 (m, 12H), 12.14 (s, 2H). ATR IR (cm⁻¹) 3214, 3062, 3015, 1655, 1574, 1531, 1494, 1414, 1350, 1296, 1191, 1074, 1029, 970, 844, 802, 756, 707, 693. LC-MS (ESI) m/z for $C_{25}H_{26}N_8O_2S_2$ calculated: 534.16, observed [M+H]: 535.

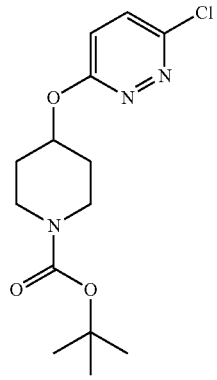 [SMILES: CC(C)(C)OC(=O)N1CCC(Oc2ccc(Cl)nn2)CC1]

Intermediate 35

4-(6-Chloro-pyridazin-3-yloxy)-piperidine-1-carboxylic Acid tert-butyl Ester

To a solution of t-butyl 4-hydroxypiperidine-1-carboxylate and (500 mg, 2.48 mmol) and 3,6-dichloropyridazine (370 mg, 2.48 mmol) in anhydrous THF (13 mL) was added DMSO (3 mL). This was followed by the addition of NaH (60% dispersion in mineral oil, 150 mg, 3.75 mmol). The reaction mixture was stirred at room temp for 20 min and then at 50° C. for 18 h. THF was evaporated to a small volume and the reaction mixture was diluted with EtOAc and washed with aq. saturated $NH_4Cl$. The aqueous layer extracted three times with EtOAc and the combined organic layer, dried over $Na_2SO_4$ and evaporated. The residue was chromatographed with silica gel column and 0-100% EtOAc in hexanes to afford the product, 4-(6-chloro-pyridazin-3-yloxy)-piperidine-1-carboxylic acid tert-butyl ester, as a white solid (570 mg, 73% yield). $^1$HNMR (600 MHz DMSO-d6) δ 1.41 (s, 9H), 1.58-1.63 (m, 2H), 1.98-2.02 (m, 2H), 3.15-3.26 (m, 2H), 3.67-3.71 (m, 2H), 5.31-5.34 (m, 1H), 7.32 (d, J=9.6 Hz, 1H), 7.80 (d, J=9.6 Hz, 1H). ATR IR (cm$^{-1}$) 2967, 1672, 1581, 1480, 1421, 1363, 1293, 1274, 1231, 1165, 1127, 1075, 1022, 938, 858, 764, 715, 673, 620 cm$^{-1}$. LC MS (ESI) m/z calculated for $C_{14}H_{20}ClN_3O_3$: 313.12, observed [M+Na]: 336.

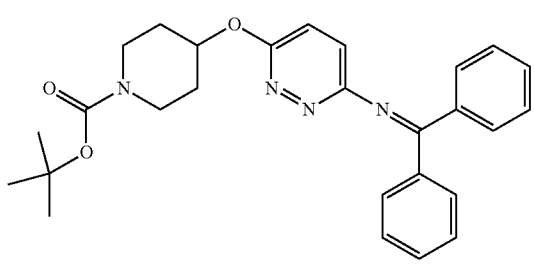 [SMILES: CC(C)(C)OC(=O)N1CCC(Oc2ccc(N=C(c3ccccc3)c3ccccc3)nn2)CC1]

Intermediate 36

4-[6-(Benzhydrylidene-amino)-pyridazin-3-yloxy]-piperidine-1-carboxylic Acid tert-butyl Ester To a sealed tube containing, tert-butyl 4-((6-chloropyridazin-3-yl)oxy) piperidine-1-carboxylate (517 mg, 1.65 mmol), diphenylmethanimine (313 mg, 1.73 mmol), (±)-BINAP (154 mg, 0.248 mmol) and $Cs_2CO_3$ (2.15 g, 6.60 mmol) was added anhydrous toluene (10 ml). After bubbling this mixture with $N_2$ for 5 minutes followed addition of $Pd_2(dba)_3$ (114 mg, 0.124 mmol). The vial was sealed, the mixture heated to 90° C. for 18 h, then cooled and filtered. The solids washed with small portions of ethyl acetate until no UV absorption was detected in the wash stream and the combined filtrate was evaporated. The residue was purified with a silica gel column and 0-100% EtOAc in hexanes to afford an orange solid that was dissolved in boiling MeOH. This solution was then cooled, filtered and evaporated to afford the desired product, 4-[6-(benzhydrylidene-amino)-pyridazin-3-yloxy]-piperidine-1-carboxylic acid tert-butyl ester, as a bright yellow solid (560 mg, 74% yield).
$^1$HNMR (600 MHz DMSO-d6) δ 1.39 (s, 9H), 1.49-1.52 (m, 2H), 1.92-1.96 (m, 2H), 3.10-3.12 (m, 2H), 3.68-3.70 (m, 2H), 5.19-5.20 (m, 1H), 7.02 (d, 1H, J=9.0 Hz), 7.10 (d, 1H, J=9.0 Hz), 7.14-7.15 (m, 2H), 7.34-7.35 (m, 3H), 7.51 (t, J=7.2 Hz, 2H), 7.59 (t, J=7.2 Hz, 1H) 7.70 (d, J=7.8 Hz, 2H). ATR IR (cm$^{-1}$) 3058, 2976, 2961, 2935, 2850, 1686, 1624, 1597, 1578, 1476, 1425, 1363, 1331, 1293, 1269, 1237, 1163, 1132, 1091, 1027, 957, 842, 818, 773, 697, 658. LC-MS (ESI) m/z calculated for $C_{27}H_{30}N_4O_3$: 458.23, observed [M+H]: 459

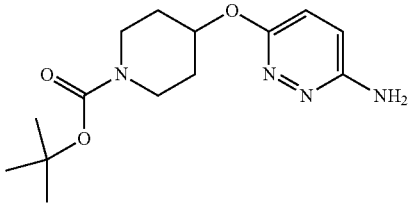 [SMILES: CC(C)(C)OC(=O)N1CCC(Oc2ccc(N)nn2)CC1]

Intermediate 37

4-(6-Amino-pyridazin-3-yloxy)-piperidine-1-carboxylic acid tert-butyl Ester

A solution of 4-[6-(benzhydrylidene-amino)-pyridazin-3-yloxy]-piperidine-1-carboxylic acid tert-butyl ester (552 mg, 1.20 mmol), hydroxylamine hydrochloride (92 mg, 1.32 mmol) and NaOAc (246 mg, 3.00 mmol) in MeOH was stirred at room temperature until TLC indicated consumption of the limiting reagent. Followed solvent evaporation to a solid residue that was chromatographed with a silica gel column and 0-10% MeOH in $CH_2Cl_2$ gradient to afford the product, 4-(6-amino-pyridazin-3-yloxy)-piperidine-1-carboxylic acid tert-butyl ester, as a foamy off-white solid (248 mg, 70% yield). $^1$HNMR (600 MHz, DMSO-d$_6$) δ 1.40 (s, 9H), 1.50-1.56 (m, 2H) 1.92-1.96 (m, 2H) 3.12-3.19 (m, 2H), 3.65-3.70 (m, 2H), 5.09-5.12 (m, 1H), 5.89 (s, 2H), 6.82-6.86 (m, 2H). ATR-IR (cm$^{-1}$) 3448, 3349, 3214, 3068, 2966, 2936, 2858, 1662, 1626, 1555, 1454, 1423, 1365, 1345, 1322, 1271, 1242, 1164, 1136, 1101, 1045, 1016, 970, 946, 860, 840, 816, 806, 775, 651, 617. LC-MS (ESI) m/z for $C_{14}H_{22}N_4O_3$ calculated: 294.35, observed [M+H]: 295.

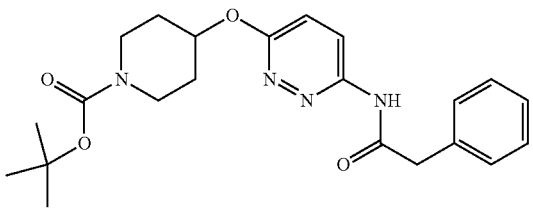 [SMILES: CC(C)(C)OC(=O)N1CCC(Oc2ccc(NC(=O)Cc3ccccc3)nn2)CC1]

Intermediate 38

4-(6-Phenylacetylamino-pyridazin-3-yloxy)-piperidine-1-carboxylic acid tert-butyl Ester tert-Butyl 4-[(6-aminopyridazin-3-yl)oxy]piperidine-1-carboxylate (230 mg, 0.78 mmol), phenylacetic acid (148 mg, 1.09 mmol), and HATU (356 mg, 0.94 mmol) are taken in 3 mL of dry DMF. DIEA (0.41 mL, 2.34 mmol) was then added and the reaction mixture was stirred at room temperature until TLC indicated consumption of the starting material. Reaction was then diluted with $H_2O$ and extracted thrice with EtOAc. The combined organic layer was evaporated and the residue was chromatographed with a silica gel column and 0-5% MeOH in $CH_2Cl_2$ gradient to afford the product, 4-(6-phenylacetylamino-pyridazin-3-yloxy)-piperidine-1-carboxylic acid tert-butyl ester, as a white solid (218 mg, 68% yield). $^1$HNMR (600 MHz DMSO-d6) δ 1.41 (d, 9H) 1.56-1.62 (m, 2H) 1.98-2.0 (m, 2H) 3.21 (broad s, 2H) 3.67-3.70 (m, 2H) 3.74 (s, 2H), 5.29-5.31 (m, 1H), 7.19 (d, 1H, J=9.6 Hz), 7.24-7.38 (m, 5H), 8.20 (d, J=9.6 Hz, 1H), 11.12 (s, 1H). ATR IR ($cm^{-1}$) 2977, 1687, 1568, 1522, 1497, 1477, 1423, 1379, 1364, 1344, 1302, 1268, 1235, 1165, 1134, 1103, 1074, 1022, 970, 936, 864, 844, 814, 768, 713, 695, 633. LC-MS (ESI) m/z calculated for $C_{22}H_{28}N_4O_4$: 412.21, observed [M+H]: 413.

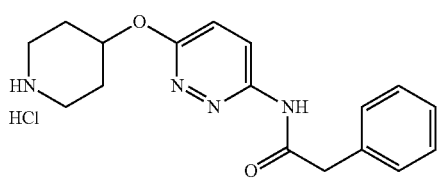 [SMILES: Cl ; O=C(Cc1ccccc1)Nc1ccc(OC2CCNCC2)nn1]

Intermediate 39

2-Phenyl-N-[6-(piperidin-4-yloxy)-pyridazin-3-yl]-acetamide hydrochloride

A solution of 4-(6-amino-pyridazin-3-yloxy)-piperidine-1-carboxylic acid tert-butyl ester (200 mg, 0.49 mmol) in dioxane (0.6 mL) was treated with 4N HCl solution in dioxane (0.97 mmol, 0.242 mL) and the resulting mixture was stirred at room temperature for 1 hour. Then followed addition of another portion of 4N HCl in dioxane (0.12 mL, 0.49 mmol), stirring for 1 h more and evaporation of the volatiles to dryness. The resulting solid was triturated with hot hexanes (3× approx. 5 ml), collected and dried to afford the product, 2-phenyl-N-[6-(piperidin-4-yloxy)-pyridazin-3-yl]-acetamide hydrochloride, as a white solid (117 mg, 70% yield). $^1$HNMR (600 MHz DMSO-d6) δ 1.93-196 (m, 2H) 2.17-2.20 (m, 2H), 3.10-3.13 (broad m, 2H) 3.21-3.23 (broad m, 2H), 3.75 (s, 2H), 5.36-5.38 (m, 2H), 7.24 (d, J=9.6 Hz, 2H), 7.31-7.35 (m, 5H), 8.23 (d, J=9.6 Hz, 1H), 8.91 (broad s, 2H), 11.16 (s, 1H). ATR IR ($cm^{-1}$) 2690, 1701, 1602, 1554, 1497, 1447, 1379, 1363, 1334, 1292, 1235, 1187, 1141, 1013, 982, 953, 868, 838, 768, 718, 694. LC-MS (ESI) m/z calculated for free base $C_{17}H_{20}N_4O_2$: 312.16, observed [M+H]: 313.

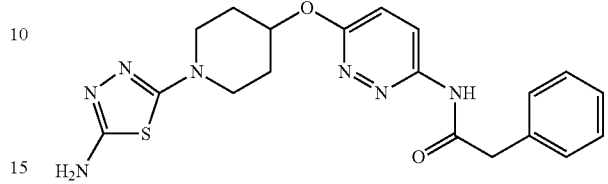

Example 37

N-{6-[1-(5-Amino-[1,3,4]thiadiazol-2-yl)-piperidin-4-yloxy]-pyridazin-3-yl}-2-phenyl-acetamide To a solution of 2-phenyl-N-(6-(piperidin-4-yloxy)pyridazin-3-yl) acetamide hydrochloride (91 mg, 0.26 mmol), $Et_3N$ (1.04 mmoles, 0.15 ml) and 2-amino-5-bromothiadiazol (57 mg, 0.32 mol) in DMF (1 mL) was stirred at 85° C. for 20 h. The DMF was then evaporated under a stream of nitrogen and the residue was treated with water (approx. 3 mL). The brown suspension that was formed was filtered and the solid was collected, dried and purified with a silica gel column and 0-20% MeOH in $CH_2Cl_2$ to afford the product, N-{6-[1-(5-amino-[1,3,4]thiadiazol-2-yl)-piperidin-4-yloxy]-pyridazin-3-yl}-2-phenyl-acetamide, as a tan solid (91 mg, 85% yield). $^1$HNMR (600 MHz DMSO-d6) δ 1.76-1.80 (m, 2H) 2.09-2.13 (m, 2H), 3.22-3.30 (m, 2H) 3.52-3.54 (m, 2H), 3.74 (s, 2H), 5.32-5.37 (m, 1H), 6.48 (s, 2H), 7.21-7.34 (m, 6H), 8.21 (d, J=10.2 Hz, 1H) 11.13 (s, 1H). ATR IR ($cm^{-1}$) 2992, 1695, 1593, 1521, 1485, 1464, 1435, 1380, 1339, 1306, 1266, 1255, 1223, 1193, 1142, 1119, 1101, 1032, 963, 942, 895, 857, 813, 770, 756, 722, 697, 668, 620. LC-MS (ESI) m/z calculated for $C_{19}H_{21}N_7O_2S$: 411.15, observed [M+H]: 412.

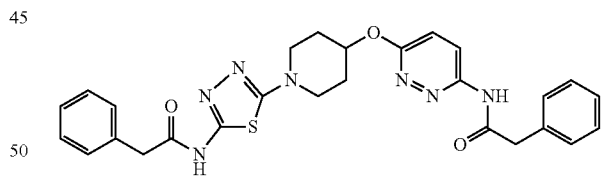

Example 38

2-Phenyl-N-{6-[1-(5-phenylacetylamino-[1,3,4]thiadiazol-2-yl)-piperidin-4-yloxy]-pyridazin-3-yl}-acetamide (UPGL00057)

A solution of N-(6-{[1-(5-amino-1,3,4-thiadiazol-2-yl)piperidin-4-yl]oxy}pyridazin-3-yl)-2-phenylacetamide (84 mg, 0.20 mmol), phenyl acetic acid (36 mg 0.27 mmol), HATU (93 mg, 0.25 mmol) and DIEA (0.15 mL, 0.82 mmol) in DMF (1.5 mL) was stirred at room temperature for 20 h. Solvent was then evaporated under a stream of nitrogen and the residue was treated with excess of water (approx. 4 mL) to afford a suspension. The suspended solid was filtered, washed with water and then dried to afford the product, 2-phenyl-N-{6-[1-(5-phenylacetylamino-[1,3,4]thiadiazol-2-yl)-piperidin-4-yloxy]-pyridazin-3-yl}-acetamide (UPGL00057), as an off-white solid (45 mg, 42% yield). $^1$HNMR (600 MHz DMSO-d6) δ 1.75-1.80 (m, 2H), 2.09-2.11 (m, 2H), 3.35-3.42 (m, 2H), 3.64-3.68 (m, 2H), 3.72 (s, 2H), 3.73 (s, 2H), 5.33-5.35 (m, 1H), 7.20 (d, J=9.6 Hz, 1H), 7.23-7.25 (m, 2H), 7.28-7.33 (m, 8H), 8.19 (d, J=9.6 Hz, 1H), 11.12 (s, 1H), 12.29 (s, 1H). ATR-IR (cm$^{-1}$) 2838, 1688, 1580, 1499, 1437, 1385, 1350, 1320, 1296, 1257, 1181, 1129, 1100, 1033, 962, 861, 759, 712, 693, 645, 627. LC-MS (ESI) m/z calculated for $C_{27}H_{27}N_7O_3S$: 529.19, observed [M+H]: 530.

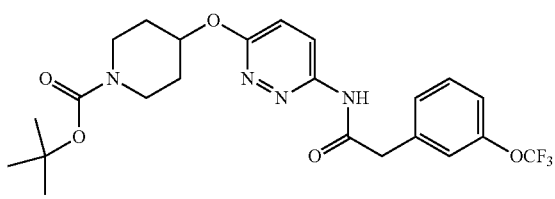 [SMILES: CC(C)(C)OC(=O)N1CCC(Oc2ccc(NC(=O)Cc3cccc(OC(F)(F)F)c3)nn2)CC1]

Intermediate 40

4-{6-[2-(3-Trifluoromethoxy-phenyl)-acetylamino]-pyridazin-3-yloxy}-piperidine-1-carboxylic Acid tert-butyl Ester A solution of 4-(6-amino-pyridazin-3-yloxy)-piperidine-1-carboxylic acid tert-butyl ester (86 mg, 0.29 mmol), DIEA (0.16 mL, 0.88 mmol), HATU (122 mg, 0.32 mmol) and 3-trifluoromethoxyphenylacetic acid (71 mg, 0.32 mmol) in DMF (1 mL) was stirred at room temperature overnight and then partitioned between EtOAc and water. The EtOAc layer was washed with brine, dried over Na$_2$SO$_4$ and evaporated to a residue that was chromatographed with a silica gel column and 0-10% MeOH in CH$_2$Cl$_2$ to afford the product, 4-{6-[2-(3-trifluoromethoxy-phenyl)-acetylamino]-pyridazin-3-yloxy}-piperidine-1-carboxylic acid tert-butyl ester, as an off-white/beige solid (91 mg, 63% yield). $^1$HNMR (600 MHz, DMSO-d$_6$) δ 1.41 (s, 9H), 1.56-1.61 (m, 2H), 1.96-2.02 (m, 2H) 3.16-3.24 (m, 2H), 3.83 (s, 2H) 5.29-5.32 (m, 1H), 7.20 (d J=9.6 Hz, 1H), 7.26 (d, J=7.8 Hz, 1H), 7.36 (d, J=12 Hz, 2H), 7.47 (t, J=8.4, 7.8 Hz, 1H), 8.20 (d, J=9.6 Hz, 1H) 11.17 (s, 1H). ATR-IR (cm$^{-1}$) 3131, 3064, 2981, 2933, 2861, 1697, 1677, 1610, 1588, 1520, 1433, 1401, 1367, 1346, 1301, 1257, 1240, 1212, 1153, 1130, 1102, 1025, 969, 946, 872, 848, 828, 761, 700, 634. LC-MS (ESI) m/z for $C_{23}H_{27}F_3N_4O_5$ calculated: 496.19, observed [M+H]: 497.

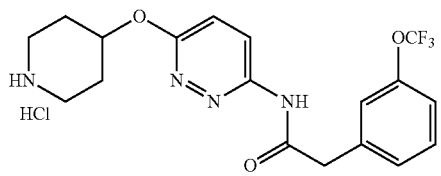 [SMILES: Cl ; O=C(Cc1cccc(OC(F)(F)F)c1)Nc1ccc(OC2CCNCC2)nn1]

Intermediate 41

N-[6-(Piperidin-4-yloxy)-pyridazin-3-yl]-2-(3-trifluoromethoxy-phenyl)-acetamide hydrochloride 4-{6-[2-(3-trifluoromethoxy-phenyl)-acetylamino]-pyridazin-3-yloxy}-piperidine-1-carboxylic acid tert-butyl ester in dioxane (0.3 mL) was treated with a solution of 4N HCl in dioxane (0.1 mL). This mixture was stirred at room temperature for 2 h and 45 min and then evaporated to dryness. The residue was triturated with hot hexanes twice and then dried to afford the product, N-[6-(piperidin-4-yloxy)-pyridazin-3-yl]-2-(3-trifluoromethoxy-phenyl)-acetamide hydrochloride, as a white solid (65 mg, 85% yield). $^1$HNMR (600 MHz, DMSO-d$_6$) δ 1.89-1.96 (m, 2H), 2.15-2.22 (m, 2H), 3.08-3.16 (m, 2H), 3.20-3.28 (m, 2H), 3.84 (s, 2H) 5.35-5.41 (m, 1H), 7.22-7.28 (m, 2H), 7.33-7.39 (m, 2H), 7.43-7.50 (m, 1H), 8.22 (d, J=9 Hz, 1H), 8.88 (s, 2H), 11.21 (s, 1H). ATR-IR (cm$^{-1}$) 2926, 2712, 2491, 1707, 1647, 1596, 1551, 1494, 1436, 1365, 1293, 1244, 1211, 1144, 1082, 1022, 943, 864, 798, 701, 633, 614. LC-MS (ESI) m/z for free base $C_{18}H_{19}F_3N_4O_3$ calculated: 396.14, observed [M+H]: 397.

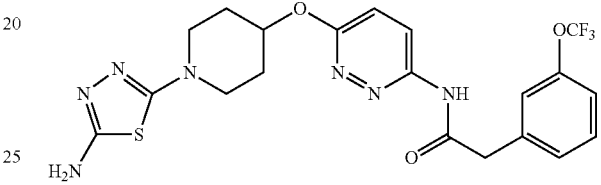

Example 39

N-{6-[1-(5-Amino-[1,3,4]thiadiazol-2-yl)-piperidin-4-yloxy]-pyridazin-3-yl}-2-(3-trifluoromethoxy-phenyl)-acetamide To a solution of N-[6-(piperidin-4-yloxy)-pyridazin-3-yl]-2-(3-trifluoromethoxy-phenyl)-acetamide hydrochloride, (62 mg, 0.14 mmol), Et$_3$N (0.08 mL, 0.57 mmol) and 2-amino-5-bromothiadiazole (31 mg, 0.17 mmol) in DMF (1.5 mL) was stirred at 85° C. for 72 h. The DMF was then evaporated under a stream of nitrogen and the residue was treated with water (approx. 3 mL). The brown suspension that was formed was filtered and the solid was collected, dried and purified with a silica gel column and 0-10% MeOH in CH$_2$Cl$_2$ to afford the product, N-{6-[1-(5-amino-[1,3,4]thiadiazol-2-yl)-piperidin-4-yloxy]-pyridazin-3-yl}-2-(3-trifluoromethoxy-phenyl)-acetamide, as a tan solid (26 mg, 37% yield). $^1$HNMR (600 MHz, MeOD-d6) δ 1.89-1.94 (m, 2H), 2.11-2.20 (m, 2H), 3.34-3.39 (m, 2H), 3.60-3.69 (m, 2H) 3.83 (s, 2H), 5.32-5.39 (m, 1H), 7.16 (dd, J=9.6, 1.8 Hz, 1H), 7.19 (d, J=7.8 Hz, 1H), 7.31 (s, 1H), 7.37 (d, J=7.8 Hz, 1H), 7.42-7.45 (m, 1H), 8.29 (d, J=9.6 Hz, 1H).
ATR-IR (cm$^{-1}$) 3279, 3169, 3136, 3066, 2926, 2852, 1691, 1608, 1492, 1432, 1379, 1299, 1248, 1210, 1147, 1024, 947, 893, 842, 700, 632. LC-MS (ESI) m/z for $C_{20}H_{20}F_3N_7O_3S$ calculated: 495.13, observed [M+H]: 496.

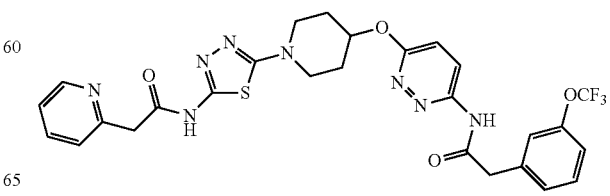

Example 40

N-(6-{1-[5-(2-Pyridin-2-yl-acetylamino)-[1,3,4]thiadiazol-2-yl]-piperidin-4-yloxy}-pyridazin-3-yl)-2-(3-trifluoromethoxy-phenyl)-acetamide (UPGL00056)

A solution of N-{6-[1-(5-amino-[1,3,4]thiadiazol-2-yl)-piperidin-4-yloxy]-pyridazin-3-yl}-2-(3-trifluoromethoxy-phenyl)-acetamide (24 mg, 0.05 mmol), 2-pyridineacetic acid (11 mg 0.06 mmol), HATU (22 mg, 0.06 mmol) and DIEA (0.04 mL, 0.19 mmol) in DMF (0.7 mL) was stirred at room temperature overnight. Followed evaporation of the mixture and treatment of the residue with water (approx. 1-2 mL) to afford a suspension. This suspension was then filtered and the solid washed with water, dried and chromatographed on a silica gel column with a 0-10% MeOH in $CH_2Cl_2$ gradient to afford the product, N-(6-{1-[5-(2-pyridin-2-yl-acetylamino)-[1,3,4]thiadiazol-2-yl]-piperidin-4-yloxy}-pyridazin-3-yl)-2-(3-trifluoromethoxy-phenyl)-acetamide (UPGL00056), as an off-white/beige solid (15 mg, 50% yield). $^1$HNMR (600 MHz, DMSO-$d_6$) δ 1.78-1.83 (m, 2H), 2.09-2.15 (m, 2H), 3.38-3.44 (m, 2H), 3.67-3.72 (m, 2H), 3.83 (s, 2H), 3.94 (s, 2H), 5.32-5.40 (m, 1H), 7.22 (d, J=9.6 Hz, 1H), 7.23-7.29 (m, 2H) 7.35-7.39 (m, 3H), 7.45-7.48 (m, 1H), 7.75-7.78 (m, 1H) 8.21 (d, J=9.6 Hz, 1 Hz), 8.48-8.49 (m, 1H), 11.19 (s, 1H) 12.32 (s, 1H). ATR-IR (cm$^{-1}$) 2932, 1685, 1571, 1511, 1432, 1341, 1250, 1210, 1146, 1101, 1029, 973, 847, 742, 701, 619. LC-MS (ESI) m/z for $C_{27}H_{25}F_3N_8O_4S$ calculated: 614.17, observed [M+H]: 615

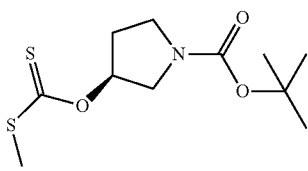 [SMILES: CSC(=S)O[C@H]1CCN(C(=O)OC(C)(C)C)C1]

Intermediate 42 tert-Butyl (3S)-3-{[(methylsulfanyl)methanethioyl]oxy}pyrrolidine-1-carboxylate

To a solution of N-Boc-(S)-3-hydroxypyrrolidine (4.10 mmol, 767 mg) in anhydrous THF (15 mL) was added NaH (60% suspension in mineral oil, 4.92 mmol, 196 mg) in two portions. After effervescence of hydrogen gas subsided, carbon disulfide (6.15 mmol, 0.37 mL) was added and then 5 min later methyl iodide (4.91 mmol, 0.31 mL) were added and the mixture was left to stir at room temperature for 18 h. The THF was then evaporated to half volume and the mixture was partitioned in dichloromethane and water. The aqueous layer was extracted with dichloromethane twice more and the combined organic layer dried over sodium sulfate, filtered and evaporated to a residue that after column chromatography with 0-50% EtOAc in hexanes afforded the product, tert-butyl (3S)-3{[(methylsulfanyl)methanethioyl]oxy}pyrrolidine-1-carboxylate, as a colorless oil (983 mg, 86.5% yield). $^1$HNMR (600 MHz, CDCl$_3$) δ 1.47 (s, 9H), 2.11-2.20 (m, 1H), 2.21-2.28 (m, 1H), 2.56 (s, 3H), 3.43-3.50 (m, 1H), 3.53-3.71 (m, 3H), 5.97 (s, 1H). ATR-IR (cm$^{-1}$) 2975, 2929, 2880, 1690, 1477, 1397, 1207, 1160, 1112, 1086, 1042, 985, 956, 922, 876, 831, 769. LC-MS (ESI) m/z calculated for $C_{11}H_{19}NO_3S_2$: 277.08, observed [M+Na]: 300.

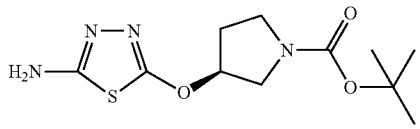 [SMILES: CC(C)(C)OC(=O)N1CC[C@H](Oc2nnc(N)s2)C1]

Intermediate 43 tert-Butyl (3S)-3-[(5-amino-1,3,4-thiadiazol-2-yl)oxy]pyrrolidine-1-carboxylate

A solution of tert-butyl (3S)-3 {[(methylsulfanyl)methanethioyl]oxy}pyrrolidine-1-carboxylate, (3.54 mmol, 983 mg) in MeOH (10 mL) was treated with hydrazine (5.31 mmol, 0.17 mL) at room temperature. After stirring for 30 min the mixture was evaporated. The residue was re-dissolved in MeOH and the solution was evaporated again. After repeating this dissolution-evaporation cycle once more, the residue in MeOH (15 mL) was treated with triethylamine (7.08 mmol, 0.99 mL) and cyanogen bromide (3M in dichloromethane 4.25 mmol, 1.4 mL). This mixture was stirred at room temperature for 18 hours, evaporated and the residue partitioned between EtOAc and water. The aqueous layer was extracted with EtOAc twice and the combined EtOAc layer was dried over sodium sulfate, filtered and evaporated. The residue obtained from this operation was then dissolved in a small amount of CHCl$_3$ (approx. 5 mL) and the resulting solution was treated with hexanes to precipitate the desired product, which was then collected via filtration. Evaporation of the filtrate and purification of the resulting residue with column and 0-5% MeOH gradient afforded a second crop of desired product that was combined with the product obtained from the precipitation step. The combined product was dissolved in CHCl$_3$ and the solution was treated with excess of hexanes to afford the desired compound, tert-butyl (3S)-3-[(5-amino-1,3,4-thiadiazol-2-yl)oxy]pyrrolidine-1-carboxylate, as an off-white, light pink solid (555 mg, 55% yield). $^1$HNMR (600 MHz, CDCl$_3$) δ 1.46 (s, 9H), 2.12-2.16 (m, 1H), 2.25-2.37 (m, 1H), 3.44-3.77 (m, 4H), 4.63 (s, 2H), 5.49 (s, 1H). ATR-IR (cm$^{-1}$) 3340, 3090, 2969, 2885, 1702, 1686, 1627, 1555, 1502, 1490, 1413, 1366, 1346, 1283, 1252, 1210, 1161, 1108, 1042, 968, 957, 930, 891, 875, 848, 765, 696.

LC-MS (ESI) m/z calculated for $C_{11}H_{18}N_4O_3S$: 286.11, observed [M−H]: 285.

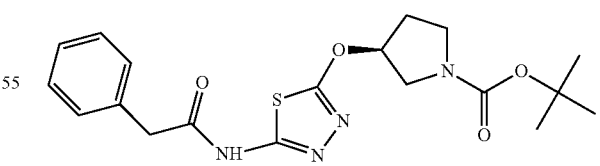

Intermediate 44 tert-Butyl (3S)-3-{[5-(2-phenylacetamido)-1,3,4-thiadiazol-2-yl]oxy}pyrrolidine-1-carboxylate tert-Butyl (3S)-3-[(5-amino-1,3,4-thiadiazol-2-yl)oxy]pyrrolidine-1-carboxylate (0.69 mmol, 196 mg) in anhydrous CH$_2$Cl$_2$ (4 mL) was treated with triethylamine (2.05 mmol, 0.28 mL) and phenyl acetyl chloride (1.64 mmol, 0.21 mL). The mixture was stirred at room temperature until consumption of the limiting reagent was observed by TLC and then partitioned between CH$_2$Cl$_2$ and water. The water layer was extracted with CH$_2$Cl$_2$ once more and the combined organic layer was dried over sodium sulfate, filtered and evaporated to a residue that after column chromatography with a 0-100% EtOAc in hexanes gradient afforded the product, tert-butyl (3S)-3-{[5-(2-phenylacetamido)-1,3,4-thiadiazol-2-yl]oxy}pyrrolidine-1-carboxylate, as an off white solid (211 mg, 76% yield). $^1$HNMR (600 MHz, DMSO-d6) δ 1.39 (d, J=6.6 Hz), 2.16-2.19 (m, 2H), 3.20-3.30 (m, overlapping with H$_2$O of DMSO, 1H), 3.41-3.45 (m, 1H), 3.49-3.61 (m, 2H), 3.76 (s, 2H), 5.43 (broad s, 1H), 7.24-7.27 (m, 1H), 7.29-7.34 (m, 4H), 12.59 (s, 1H). AT-IR (cm$^{-1}$) 2974, 1689, 1570, 1502, 1458, 1410, 1362, 1328, 1306, 1262, 1174, 1148, 1120, 960, 885, 850, 771, 749, 725, 694, 647. LC-MS (ESI) m/z calculated for C$_{19}$H$_{24}$N$_4$O$_4$S: 404.15, observed [M−H]: 403.

Intermediate 45

2-phenyl-N-{5-[(3S)-pyrrolidin-3-yloxy]-1,3,4-thiadiazol-2-yl}acetamide hydrochloride tert-Butyl (3S)-3-{[5-(2-phenylacetamido)-1,3,4-thiadiazol-2-yl]oxy}pyrrolidine-1-carboxylate (0.52 mmol, 211 mg) was treated with 4M HCl in dioxane (2.60 mmol, 0.60 mL). The mixture was stirred at room temperature until TLC showed complete consumption of starting material. The mixture was then evaporated to dryness and the solid residue was triturated twice with boiling CH$_2$Cl$_2$ and dried to afford the product, 2-phenyl-N-{5-[(3S)-pyrrolidin-3-yloxy]-1,3, 4-thiadiazol-2-yl}acetamide hydrochloride, as a white solid (79 mg, 50% yield].

$^1$HNMR (600 MHz, DMSO-d6) δ 2.25-2.28 (m, 2H), 3.25-3.33 (m, 2H, buried under H$_2$O of DMSO), 3.46-3.56 (m, 2H), 3.77 (s, 2H), 5.56 (s, brd, 1H), 7.25-7.27 (m, 1H), 7.30-7.34 (m, 4H), 9.39 (s, 2H), 12.67 (s, 1H). ATR-IR (cm$^{-1}$) 3324, 3034, 2976, 2850, 2748, 2657, 2605, 2489, 1655, 1579, 1492, 1415, 1353, 1260, 1193, 1055, 1029, 952, 793, 762, 726, 700, 630. LC-MS (ESI) m/z calculated for free base C$_{14}$H$_{16}$N$_4$O$_2$S: 304.10, observed [M+H]: 305.

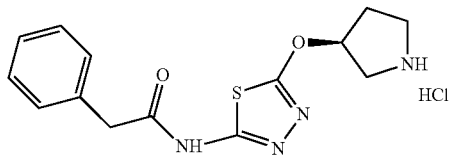 [SMILES: O=C(Cc1ccccc1)Nc1nnc(O[C@H]2CCNC2)s1 ; Cl]

Example 41

N-(5-{[(3S)-1-(5-amino-1,3,4-thiadiazol-2-yl)pyrrolidin-3-yl]oxy}-1,3,4-thiadiazol-2-yl)-2-phenylacetamide (UPGL00035)

A solution of 2-phenyl-N-{5-[(3S)-pyrrolidin-3-yloxy]-1, 3,4-thiadiazol-2-yl}acetamide hydrochloride (0.26 mmol, 79.5 mg), 2-amino-5-bromothiadiazole (0.29 mmol, 52 mg) and triethylamine (1.04 mmol, 0.14 mL) in EtOH (1 mL) was stirred at 76° C. for 18 hours. The mixture was then cooled to room temperature, evaporated to a minimal volume under a stream of N$_2$ and treated with excess of water to produce a suspension. Filtration and collection of the precipitate followed by column chromatography with 0-10% MeOH in CH$_2$Cl$_2$ gradient afforded the product, N-(5-{[(3S)-1-(5-amino-1,3,4-thiadiazol-2-yl)pyrrolidin-3-yl]oxy}-1,3,4-thiadiazol-2-yl)-2-phenylacetamide (UPGL00035), as a tan/brown solid (34.4 mg, 32.8% yield). $^1$HNMR (600 MHz, DMSO-d6) δ 2.27-2.34 (m, 1H), 2.35-2.39 (m, 2H), 3.43 (dd, 2H, J=9 &4.8 Hz), 3.58 (d, 1H, J=12 Hz), 3.71 (dd, 1H, J=12.0& 4.8 Hz), 3.76 (s, 2H), 5.53-5.57 (m, 1H), 6.38 (s, 2H), 7.25-7.34 (m, 5H), 12.60 (s, 1H). ATR-IR (cm$^{-1}$) 3400, 3275, 3157, 2847, 1664, 1562, 1494, 1470, 1365, 1351, 1331, 1313, 1284, 1252, 1217, 1190, 1157, 1096, 1078, 1055, 1031, 948, 850, 790, 752, 726, 713, 692, 643. LC-MS (ESI) m/z calculated for C$_{16}$H$_{17}$N$_7$O$_2$S$_2$: 403.09, observed [M+H]: 404.

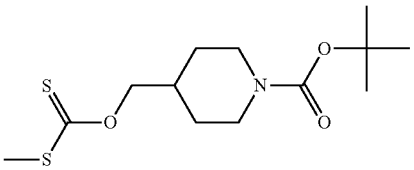

Intermediate 46 tert-butyl-4-({[(methylsulfanyl)methanethioyl]oxy}methyl)piperidine-1-carboxylate tert-Butyl 4-(hydroxymethyl)piperidine-1-carboxylate (1.66 mmol, 358 mg) in anhydrous THF (12 mL) was treated with NaH (60% suspension in mineral oil, 1.99 mmol, 80 mg) and the mixture was stirred until the effervescence of hydrogen gas subsided. Then followed addition of carbon disulfide (2.49 mmol, 0.15 mL) and then, after approximately 5 min, addition of methyl iodide (1.99 mmol, 0.13 mL). The mixture was stirred at room temperature for 18 hours then evaporated to half volume under a stream of nitrogen and partitioned between EtOAc and water. The water layer was extracted with EtOAc four times and the combined organic layer was evaporated to a residue that after chromatography with a 0-50% EtOAc in hexanes gradient afforded the product, tert-butyl-4-({[(methylsulfanyl)methanethioyl]oxy}methyl) piperidine-1-carboxylate, as a colorless oil (420 mg, 82% yield).

$^1$HNMR (600 MHz, CDCl$_3$) δ 1.22-1.29 (m, 2H), 1.46 (s, 9H), 1.74 (d, J=12.6 Hz, 2H), 1.98-2.05 (m, 1H), 2.56 (s, 3H), 2.72 (s, brd, 2H), 4.14 (s, brd, 2H), 4.46 (d, J=6.6 Hz, 2H). ATR-IR (cm$^{-1}$) 2973, 2927, 2852, 1685, 1448, 1418, 1364, 1288, 1274, 1213, 1165, 1139, 1060, 997, 970, 863, 768. LC-MS (ESI) m/z calculated for C$_{13}$H$_{23}$NO$_3$S$_2$: 305.11, observed [M+Na]: 328.

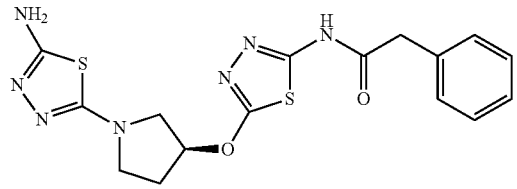 [SMILES: Nc1nnc(N2CC[C@H](Oc3nnc(NC(=O)Cc4ccccc4)s3)C2)s1]

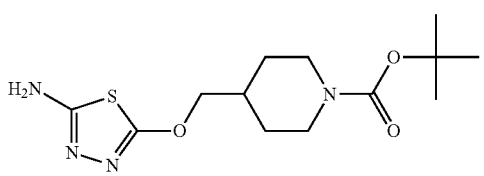 [SMILES: CC(C)(C)OC(=O)N1CCC(COc2nnc(N)s2)CC1]

Intermediate 47

4-(5-Amino-[1,3,4]thiadiazol-2-yloxymethyl)-piperidine-1-carboxylic Acid tert-butyl Ester A mixture of tert-butyl-4-({[(methylsulfanyl)methanethioyl]oxy}methyl) piperidine-1-carboxylate, (1.38 mmol, 420 mg) and hydrazine (2.06 mmol, 0.07 mL) in MeOH (20 mL) was stirred at room temperature for 60 minutes and then evaporated. The residue was re-dissolved in methanol and the resulting solution was evaporated again. After repeating this dissolution-evaporation cycle once more the residue in MeOH (20 mL), was treated with triethylamine (2.75 mmol, 0.38 mL) and then at 0° C. with cyanogen bromide (3M solution in dichloromethane, 4.25 mmol, 1.4 mL). The mixture was allowed to warm up to room temperature, stirred for 48 h and evaporated. The residue was partitioned between EtOAc and water. The aqueous layer was extracted with EtOAc twice more and the combined organic layer was evaporated to a residue that chromatographed using a 0-10% MeOH in dichloromethane gradient. Product containing fractions were evaporated to dryness. The residue was then dissolved in a small volume of dichloromethane. Treatment of this solution with excess of hexanes led to the precipitation of the product, 4-(5-amino-[1,3,4]thiadiazol-2-yloxymethyl)-piperidine-1-carboxylic acid tert-butyl ester, as an off-white, light pink solid (133 mg, 31% yield). $^1$HNMR (600 MHz, DMSO-d6) δ 1.10 (ddd, J=24.6, 12.6, 4.2 Hz, 2H), 1.39 (s, 9H), 1.67 (d, J=12.6 Hz, 2H), 1.92-1.94 (m, 1H), 2.70 (broad s, 2H), 3.95 (broad s, 2H), 4.14 (d, J=6.6 Hz, 2H), 6.73 (s, 2H). ATR-IR (cm$^{-1}$) 3296, 3103, 2974, 2928, 1680, 1625, 1559, 1513, 1498, 1458, 1433, 1383, 1363, 1302, 1262, 1233, 1175, 1132, 1092, 1068, 998, 979, 931, 902, 867, 827, 764, 686. LC-MS (ESI) m/z calculated for $C_{13}H_{22}N_4O_3S$: 314.14, observed [M+H]: 315.

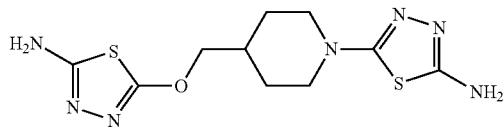 [SMILES: Nc1nnc(OCC2CCN(c3nnc(N)s3)CC2)s1]

Example 42

5-(4-{[(5-amino-1,3,4-thiadiazol-2-yl)oxy]methyl}piperidin-1-yl)-1,3,4-thiadiazol-2-amine To a solution 4-(5-amino-[1,3,4]thiadiazol-2-yloxymethyl)-piperidine-1-carboxylic acid tert-butyl ester (134 mg, 0.43 mmol) in dioxane (1 ml) was added 4M HCl in dioxane (1.27 mmol, 0.32 mL) and the reaction mixture stirred at room temperature until TLC indicated complete consumption of the starting material. Dioxane was then evaporated to dryness using a stream of $N_2$ and the solid residue triturated with boiling dichloromethane and hexanes and dried. This intermediate without further purification was taken up in ethanol (1 mL). The resulting mixture was treated with Et$_3$N (1.70 mmol, 0.23 mL) and 2-amino-5-bromothiadiazole (0.47 mmol, 84 mg) and stirred at 80° C. in a sealed tube until TLC indicated complete consumption of the limiting reagent. The reaction mixture was then cooled, evaporated to a minimum volume (approximately 0.2 mL) and treated with excess of water to afford a precipitate that was filtered, then washed with water, dried, triturated with boiling dichloromethane and hexanes and dried again to afford the product 5-(4-{[(5-amino-1,3,4-thiadiazol-2-yl)oxy] methyl}piperidin-1-yl)-1,3,4-thiadiazol-2-amine as a tan solid (35 mg, 26% yield). $^1$HNMR (600 MHz, DMSO-d$_6$) δ 1.33 (ddd, J=4.8 Hz, 12.6 Hz, 16.8 Hz, 2H), 1.73 (d, J=12.6 Hz, 2H), 1.93-2.02 (m, 1H), 2.88-2.95 (m, 2H), 3.63 (d, J=13.2 Hz, 2H), 4.17 (d, J=6.0 Hz, 2H), 6.43 (s, 2H), 6.74 (s, 2H). ATR-IR (cm$^{-1}$) 3260, 3112, 2946, 1616, 1551, 1492, 1457, 1384, 1328, 1291, 1262, 1215, 1049, 1000, 983, 959, 894, 834, 760, 685. LC-MS (ESI) m/z for $C_{10}H_{15}N_7OS_2$ calculated: 313.08, observed [M−H]312.

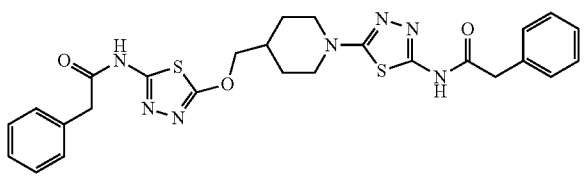 [SMILES: O=C(Cc1ccccc1)Nc1nnc(OCC2CCN(c3nnc(NC(=O)Cc4ccccc4)s3)CC2)s1]

Example 43

2-Phenyl-N-{5-[1-(5-phenylacetylamino-[1,3,4]thiadiazol-2-yl)-piperidin-4-ylmethoxy]-[1,3,4]thiadiazol-2-yl}-acetamide (UPGL00034)

A mixture of 5-(4-{[(5-amino-1,3,4-thiadiazol-2-yl)oxy]methyl}piperidin-1-yl)-1,3,4-thiadiazol-2-amine (0.07 mmol, 21 mg) and triethylamine (0.20 mmol, 0.03 mL) in DMF (1 mL) was treated with phenylacetyl chloride (0.15 mmol, 0.02 mL) and stirred at room temperature for 36 h. The mixture was then treated with excess of water and the resulting precipitate was filtered, washed with water, dried and chromatographed with a 0-15% MeOH in CH$_2$Cl$_2$ gradient to afford the product, 2-phenyl-N-{5-[1-(5-phenylacetylamino-[1,3,4]thiadiazol-2-yl)-piperidin-4-ylmethoxy]-[1,3,4]thiadiazol-2-yl}-acetamide (UPGL00034), as an off-white solid (19 mg, 52% yield). $^1$HNMR (600 MHz, DMSO-d6) δ 1.36 (ddd, J=15.6, 12.6, 3.6 Hz, 2H), 1.78 (d, J=12.6 Hz, 2H), 2.07-2.08 (m, 1H), 3.04 (t, J=12 Hz, 2H), 3.72 (s, 2H), 3.75 (s, 2H), 3.82 (d, J=13.2 Hz, 2H), 4.29 (d, J=6.6 Hz, 2H), 7.25-7.34 (m, 10H), 12.28 (s, 1H), 12.56 (s, 1H). ATR IR (cm$^{-1}$) 3389, 3264, 3156, 2849, 1693, 1563, 1494, 1255, 969, 693, 646. LC-MS (ESI) m/z calculated for $C_{26}H_{27}N_7O_3S_2$: 549.16, observed [M+H]: 550.

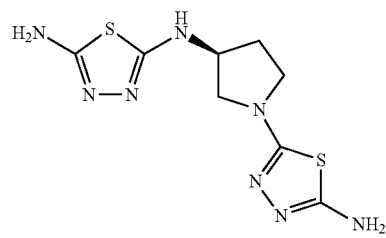 [SMILES: Nc1nnc(N[C@H]2CCN(c3nnc(N)s3)C2)s1]

Example 44

(S)—N2-(1-(5-amino-1,3,4-thiadiazol-2-yl) pyrrolidin-3-yl)-1,3,4-thiadiazole-2,5-diamine (UPGL00006)

A solution of 2-amino-5-bromothiadiazole (399 mg, 2.22 mmol), (S)-pyrrolidin-3-amine (96 mg, 1.11 moles) and NaHCO$_3$ (559 mg, 6.66 mmol) in EtOH (10 mL) in a sealed tube was heated at 80° C. for 48 h. The mixture was then cooled, concentrated to a small volume via a stream of N$_2$, filtered and evaporated to a residue that was purified via column and 0-30% MeOH in CH$_2$Cl$_2$ gradient to afford the product, (S)—N2-(1-(5-amino-1,3,4-thiadiazol-2-yl) pyrrolidin-3-yl)-1,3,4-thiadiazole-2,5-diamine, as a tan solid (307 mg, 97% yield). $^1$HNMR (600 MHz, DMSO-d$_6$) δ 1.93-1.98 (m, 1H), 2.19-2.24 (m, 1H), 3.24 (dd, J=10.2, 3.6 Hz, 1H), 3.31-3.37 (m, 1H), 3.39-3.44 (m, 1H), 3.56 (dd, J=10.2, 6.0 Hz, 1H), 4.18-4.20 (m, 1H), 6.31 (s, 2H), 6.32 (s, 2H), 7.10 (d, J=6 Hz, 1H). ATR-IR (cm$^{-1}$) 3252, 3136, 2860, 1606, 1563, 1492, 1470, 1334, 1299, 1235, 1188, 1117, 1028, 744, 671. LC-MS (ESI) m/z for C$_8$H$_{12}$N$_8$S$_2$ calculated: 284.06, observed [M+H]: 285.

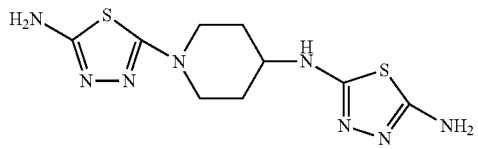 [SMILES: Nc1nnc(NC2CCN(c3nnc(N)s3)CC2)s1]

Example 45

N2-(1-(5-amino-1,3,4-thiadiazol-2-yl) piperidin-4-yl)-1,3,4-thiadiazole-2,5-diamine (UPGL00005)

A solution of 2-amino-5-bromothiadiazole (399 mg, 2.22 mmoles), 4-aminopiperidine (0.12 ml, 1.11 moles) and NaHCO$_3$ (559 mg, 6.66 mmoles) in EtOH (10 mL) in a sealed tube was heated at 80° C. for 48 h. The mixture was then cooled, filtered and evaporated. The residue was purified via column with a 0-35% MeOH in CH$_2$Cl$_2$ gradient to afford the product, N2-(1-(5-amino-1,3,4-thiadiazol-2-yl) piperidin-4-yl)-1,3,4-thiadiazole-2,5-diamine (UPGL00005), as a tan solid (144 mg, 43% yield). $^1$HNMR (600 MHz, DMSO-d$_6$) δ 1.43-1.529 (m, 2H), 1.95-2.01 (m, 2H), 3.01-3.08 (apparent triplet, 2H), 3.53-3.63 (m, 2H), 6.32 (s, 2H), 6.47 (s, 2H), 6.86 (s, 1H). ATR-IR (cm$^{-1}$) 3257, 3137, 2926, 1611, 1560, 1490, 1445, 1375, 1359, 1309, 1263, 1220, 1121, 1082, 1029, 979, 900, 841, 803, 747, 669. LC-MS (ESI) m/z for C$_9$H$_{14}$N$_8$S$_2$ calculated: 298.08, observed [M+H]: 299.

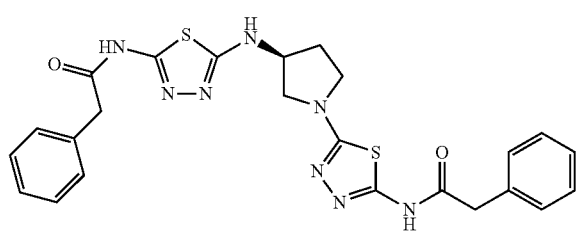 [SMILES: O=C(Cc1ccccc1)Nc1nnc(N[C@H]2CCN(c3nnc(NC(=O)Cc4ccccc4)s3)C2)s1]

Example 46

(S)-2-phenyl-N-(5-(3-((5-(2-phenylacetamido)-1,3,4-thiadiazol-2-yl)amino) pyrrolidin-1-yl)-1,3,4-thiadiazol-2-yl) acetamide (UPGL00009)

A solution of (S)—N2-(1-(5-amino-1,3,4-thiadiazol-2-yl) pyrrolidin-3-yl)-1,3,4-thiadiazole-2,5-diamine (UPGL00006) (100 mg, 0.35 mmol) and Et$_3$N (0.147 ml, 1.06 mmol) in anhydrous DMF (1 mL) was treated with phenylacetyl chloride (0.09 mL, 0.71 mmol). After stirring for 24 h at room temperature, DMF was evaporated to a minimum volume and water added to the reaction of mixture. The solid that precipitated was filtered, washed with water, dried and purified via column and a 0-30% MeOH in CH$_2$Cl$_2$ gradient to afford the product, (S)-2-phenyl-N-(5-(3-((5-(2-phenylacetamido)-1,3,4-thiadiazol-2-yl)amino) pyrrolidin-1-yl)-1,3,4-thiadiazol-2-yl) acetamide, as an off-white solid (76 mg, 41% yield).

$^1$HNMR (600 MHz, DMSO-d$_6$) δ 1.99-2.06 (m, 1H), 2.24-2.32 (m, 1H), 3.35-3.39 (m, 1H), 3.42-3.54 (m, 2H), 3.71 (singlet overlapping with a multiplet, 5H), 4.30-4.36 (m, 1H), 7.22-7.26 (m, 2H), 7.27-7.34 (m, 8H), 7.65 (broad s, 1H), 12.21 (s, 1H), 12.24 (s, 1H). ATR-IR (cm$^{-1}$) 3188, 2861, 1681, 1578, 1509, 1459, 1342, 1312, 1291, 1235, 1192, 1134, 1073, 1030, 970, 833, 756, 718, 693, 646. LC-MS (ESI) m/z for C$_{24}$H$_{24}$N$_8$O$_2$S$_2$ calculated: 520.15, observed [M−H]: 519.

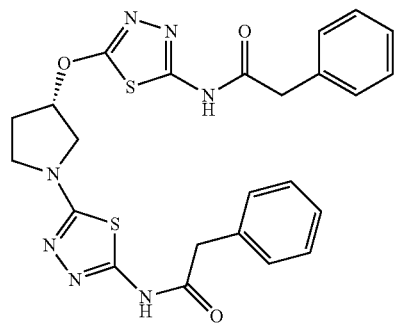 [SMILES: O=C(Cc1ccccc1)Nc1nnc(O[C@H]2CCN(c3nnc(NC(=O)Cc4ccccc4)s3)C2)s1]

Example 47

(S)-2-phenyl-N-(5-(3-((5-(2-phenylacetamido)-1,3,4-thiadiazol-2-yl)oxy) pyrrolidin-1-yl)-1,3,4-thiadiazol-2-yl) acetamide (UPGL00015)

A solution of (S)-5-(3-((5-amino-1,3,4-thiadiazol-2-yl)oxy)pyrrolidin-1-yl)-1,3,4-thiadiazol-2-amine (UPGL00014) (26 mg, 0.09 mmol) and Et$_3$N (0.05 mL, 0.36 mmol) in anhydrous DMF (1 mL) was treated with phenylacetyl chloride (0.03 mL, 0.23 mmol). After stirring for 48 h at room temperature, DMF was evaporated to a minimum volume and water added to the reaction of mixture. The solid that precipitated was filtered, washed with water, dried and chromatographed via column and 0-20% MeOH in CH$_2$Cl$_2$ gradient. Product containing fractions were combined, and evaporated and the resulting residue was triturated with boiling hexanes and then dried to afford the product, (S)-2-phenyl-N-(5-(3-((5-(2-phenylacetamido)-1,3,4-thiadiazol-2-yl)oxy) pyrrolidin-1-yl)-1,3,4-thiadiazol-2-yl), as an off-white light pink solid (10 mg, 21% yield). $^1$HNMR (600 MHz, DMSO-d$_6$) δ 2.31-2.42 (m, 2H), 3.48-3.57 (m, 2H), 3.69 (d, J=12 Hz, 1H), 3.72 (s, 2H), 3.75 (s, 2H), 3.79 (dd, J=12.0, 4.2 Hz, 1H), 5.55-5.56 (m, 1H), 7.25-7.33 (m, 10H), 12.29 (broad s, 1H), 12.59 (broad s, 1H). ATR-IR (cm$^{-1}$) 3179, 3060, 3031, 2915, 2851, 2808, 2750, 1684, 1573, 1530, 1495, 1454, 1360, 1298, 1256, 1198, 1147, 1080, 1028, 957, 857, 758, 714, 694, 640. LC-MS (ESI) m/z for $C_{24}H_{23}N_7O_3S_2$ calculated: 521.13, observed [M+H]522.

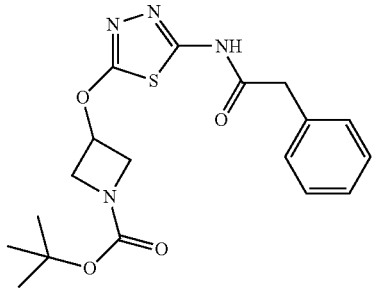 [SMILES: CC(C)(C)OC(=O)N1CC(Oc2nnc(NC(=O)Cc3ccccc3)s2)C1]

Intermediate 48 tert-butyl 3-((5-(2-phenylacetamido)-1,3,4-thiadiazol-2-yl)oxy)azetidine-1-carboxylate A solution of tert-butyl 3-((5-amino-1,3,4-thiadiazol-2-yl)oxy)azetidine-1-carboxylate (300 mg, 1.10 mmol) and Et$_3$N (0.46 ml, 3.31 mmol) in anhydrous dichloromethane (5 mL) was treated with phenylacetyl chloride (0.22 mL, 1.65 mmol). After stirring for 18 h at room temperature, the reaction mixture is diluted with water and extracted with dichloromethane. The organic solvent was collected and evaporated to dryness and the residue was chromatographed via column and 0-100% EtOAc in hexanes gradient to afford the product, tert-butyl 3-((5-(2-phenylacetamido)-1,3,4-thiadiazol-2-yl)oxy)azetidine-1-carboxylate, as a white solid. (110 mg, 45% yield). $^1$HNMR (600 MHz, DMSO-d$_6$) δ 1.38 (s, 9H), 3.77 (s, 2H), 3.91 (broad s, 2H), 4.25 (broad s, 2H), 5.35-5.37 (m, 1H), 7.26-7.34 (m, 5H), 12.65 (s, 1H). ATR-IR (cm$^{-1}$) 3162, 2971, 2926, 2888, 2815, 1700, 1688, 1565, 1504, 1480, 1453, 1392, 1349, 1308, 1273, 1176, 1137, 1089, 1022, 1005, 972, 948, 872, 857, 839, 813, 766, 723, 693, 648. LC-MS (ESI) m/z for $C_{18}H_{22}N_4O_4S$ calculated: 390.14, observed [M+Na]: 413.

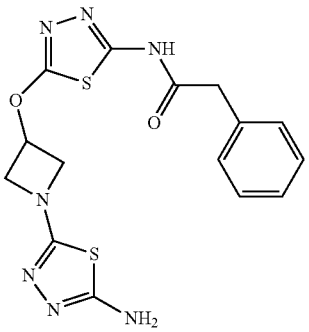 [SMILES: Nc1nnc(N2CC(Oc3nnc(NC(=O)Cc4ccccc4)s3)C2)s1]

Example 48

N-(5-((1-(5-amino-1,3,4-thiadiazol-2-yl)azetidin-3-yl)oxy)-1,3,4-thiadiazol-2-yl)-2-phenylacetamide (UPGL00038)

To a solution of tert-butyl 3-((5-(2-phenylacetamido)-1,3,4-thiadiazol-2-yl)oxy)azetidine-1-carboxylate (111 mg, 0.28 mmol) in dioxane (0.5 mL) is added 4M HCl in dioxane (0.50 mL). The reaction mixture stirred until TLC indicated complete consumption of starting material and then evaporated to a residue that was triturated with boiling hexanes and then dried. This intermediate without further delay was then taken up in in ethanol (3 mL). The resulting mixture was treated with Et$_3$N (0.16 ml, 1.14 mmol) and 2-amino-5-bromothiadiazole (50 mg, 0.28 mmol) and stirred at 100° C. in a sealed vessel until TLC indicated complete consumption of the limiting reagent. The mixture was then cooled, evaporated to a minimum volume (approximately 0.5 mL) and treated with water to afford a precipitate that was then filtered, washed with water, dried and chromatographed via column and 0-20% MeOH in CH$_2$Cl$_2$ gradient to afford the product, N-(5-((1-(5-amino-1,3,4-thiadiazol-2-yl)azetidin-3-yl)oxy)-1,3,4-thiadiazol-2-yl)-2-phenylacetamide, as a tan solid (27 mg, 25% yield). $^1$HNMR (600 MHz, DMSO-d$_6$) δ 3.77 (s, 2H), 4.01 (dd, J=9.6, 3.6 Hz, 2H), 4.34 (dd, J=9.0, 6.6 Hz, 2H), 5.52-5.53 (m, 1H), 6.56 (s, 2H), 7.25-7.34 (m, 5H), 12.66 (s, 1H). ATR-IR cm$^{-1}$ 3408, 3277, 3137, 3089, 2919, 2868, 1686, 1567, 1493, 1457, 1350, 1308, 1264, 1155, 1103, 1047, 975, 951, 881, 828, 748, 725, 692, 644. LC-MS (ESI) m/z for $C_{15}H_{15}N_7O_2S2$ calculated: 389.07, observed [M+H]: 390.

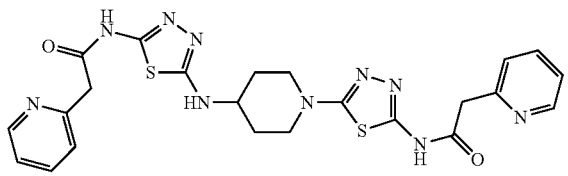 [SMILES: O=C(Cc1ccccn1)Nc1nnc(NC2CCN(c3nnc(NC(=O)Cc4ccccn4)s3)CC2)s1]

Example 49

2-(Pyridin-2-yl)-N-{5-[(1-{5-[2-(pyridin-2-yl)acetamido]-1,3,4-thiadiazol-2-yl}piperidin-4-yl)amino]-1,3,4-thiadiazol-2-yl}acetamide (UPGL00060)

A mixture of 2-N-[1-(5-amino-1,3,4-thiadiazol-2-yl)piperidin-4-yl]-1,3,4-thiadiazole-2,5-diamine (100 mg, 0.34 mmol), 2-pyridylacetic acid hydrochloride (128 mg, 0.74 mmol), DIEA (0.35 mL, 2.01 mmol) and HATU (383 mg, 1.00 mmol) in anhydrous DMF (2 ml) was stirred at room temperature until consumption of the limiting reagent was complete. The mixture was then evaporated to a solid residue that was purified by column chromatography (0-15% MeOH in CH$_2$Cl$_2$) to afford a solid that after precipitation out of MeOH with EtOAc afforded the product, 2-(pyridin-2-yl)-N-{5-[(1-{5-[2-(pyridin-2-yl)acetamido]-1,3,4-thiadiazol-2-yl}piperidin-4-yl)amino]-1,3,4-thiadiazol-2-yl}acetamide, as a tan solid (26 mg, 15%). $^1$H NMR (600 MHz, DMSO-d6) δ 1.48-1.56 (m, 2H), 2.02-2.07 (m, 2H), 3.17-3.23 (apparent t, 2H), 3.72-3.78 (m, 3H), 3.91 (s, 2H), 3.94 (s, 2H), 7.25-7.30 (m, 2H), 7.33-7.39 (m, 3H), 7.73-7.78 (m, 2H), 8.45-8.50 (m, 2H), 12.10-12.40 (broad s, 2H). ATR IR cm$^{-1}$ 3314, 3154, 2953, 1685, 1677, 1583, 1561, 1501, 1462, 1438, 1407, 1378, 1345, 1288, 1260, 1195, 1148, 1128, 1079, 1008, 959, 940, 906, 859, 843, 765, 750, 720, 699, 680, 651, 614, 600. LCMS (ESI) m/z for $C_{23}H_{24}N_{10}O_2S_2$ calculated: 536.15, observed [M+H]: 537.

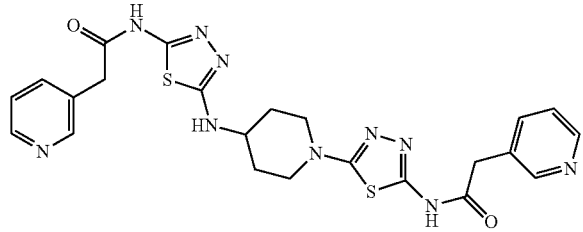 [SMILES: O=C(Cc1cccnc1)Nc1nnc(NC2CCN(c3nnc(NC(=O)Cc4cccnc4)s3)CC2)s1]

Example 50

2-(Pyridin-3-yl)-N-{5-[(1-{5-[2-(pyridin-3-yl)acet-amido]-1,3,4-thiadiazol-2-yl}piperidin-4-yl)amino]-1,3,4-thiadiazol-2-yl}acetamide (UPGL00061)

A mixture of 2-N-[1-(5-amino-1,3,4-thiadiazol-2-yl)piperidin-4-yl]-1,3,4-thiadiazole-2,5-diamine (100 mg, 0.34 mmol), 3-pyridylacetic acid (101 mg, 0.74 mmol), and HATU (319 mg, 0.84 mmol) in anhydrous DMF (2 ml) was treated with DIEA (0.24 mL, 1.34 mmol) and the resulting mixture was stirred at room temperature until consumption of the limiting reagent was complete. The mixture was then evaporated to a solid residue to which water was added. The suspension that resulted was then filtered to afford a yellow solid that was dried, triturated with boiling MeOH (X2) and dried again to afford the product, 2-(pyridin-3-yl)-N-{5-[(1-{5-[2-(pyridin-3-yl)acetamido]-1,3,4-thiadiazol-2-yl}piperidin-4-yl)amino]-1,3,4-thiadiazol-2-yl}acetamide, as a tan solid (24 mg, 14%). $^1$H NMR (600 MHz, DMSO-d6) δ 1.47-1.54 (m, 2H), 2.01-2.06 (m, 2H), 3.16-3.22 (m, 2H), 3.72-3.77 (m, 3H), 3.77 (s, 2H), 3.80 (s, 2H), 7.33-7.39 (m, 3H), 7.69-7.73 (m, 2H), 8.45-8.51 (m, 4H), 12.23 (s, 1H), 12.35 (s, 1H). ATR IR cm$^{-1}$ 3314, 3154, 2953, 1685, 1677, 1583, 1561, 1524, 1501, 1462, 1438, 1407, 1378, 1345, 1288, 1260, 1195, 1148, 1128, 1079, 1008, 959, 940, 906, 859, 843, 811, 798, 765, 750, 720, 699, 680, 651, 614, 600. LCMS (ESI) m/z for $C_{23}H_{24}N_{10}O_2S_2$ calculated: 536.15, observed [M+H]: 537.

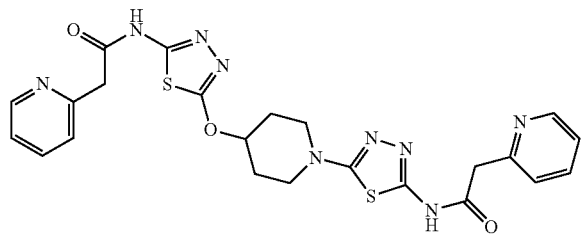 [SMILES: O=C(Cc1ccccn1)Nc1nnc(OC2CCN(c3nnc(NC(=O)Cc4ccccn4)s3)CC2)s1]

Example 51

2-(Pyridin-2-yl)-N-{5-[(1-{5-[2-(pyridin-2-yl)acet-amido]-1,3,4-thiadiazol-2-yl}piperidin-4-yl)oxy]-1,3,4-thiadiazol-2-yl}acetamide (UPGL00063)

5-{4-[(5-amino-1,3,4-thiadiazol-2-yl)oxy]piperidin-1-yl}-1,3,4-thiadiazol-2-amine (63 mg, 0.21 mmol), 2-pyridylacetic acid hydrochloride (80 mg, 0.46 mmol) and HATU (200 mg, 0.53 mmol) in anhydrous DMF (1.5 ml) was treated with DIEA (0.22 mL, 1.26 mmol) and the mixture was stirred at room temperature until consumption of the limiting reagent was complete. The mixture was then evaporated to a solid residue to which was added water. The suspension formed was filtered to afford a yellow solid that was then dried and chromatographed with column and 0-15% MeOH in CH$_2$Cl$_2$ gradient as eluent to afford the product, 2-(pyridin-2-yl)-N-{5-[(1-{5-[2-(pyridin-2-yl)acet-amido]-1,3,4-thiadiazol-2-yl}piperidin-4-yl)oxy]-1,3,4-thiadiazol-2-yl}acetamide, as a pale-yellow solid (55 mg, 49%). $^1$H NMR (600 MHz, DMSO-d6) δ 1.81-1.89 (m, 2H), 2.11-2.18 (m, 2H), 3.34-3.41 (m, 2H), 3.63-3.69 (m, 2H), 3.94 (s, 2H), 3.97 (s, 2H), 7.26-7.30 (m, 2H), 7.38 (dd, 2H, J=7.8, 3.0 Hz), 7.76 (t, J=7.8 Hz, 2H), 8.49 (d, J=4.2 Hz, 2H) 12.33 (s, 1H), 12.60 (s, 1H).

ATR IR cm$^{-1}$ 3242, 3187, 3089, 3033, 2992, 2945, 2840, 1668, 1583, 1561, 1491, 1460, 1433, 1409, 1381, 1352, 1325, 1303, 1286, 1248, 1191, 1166, 1122, 1053, 1021, 947, 900, 854, 788, 769, 747, 685, 651, 621. LCMS (ESI) m/z for $C_{23}H_{23}N_9O_3S_2$ calculated: 537.14, observed: [M+H]: 538.

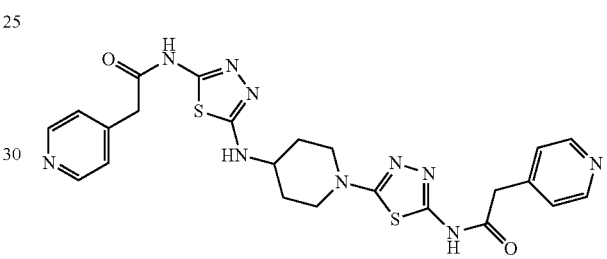

Example 52

2-(Pyridin-4-yl)-N-{5-[(1-{5-[2-(pyridin-4-yl)acet-amido]-1,3,4-thiadiazol-2-yl}piperidin-4-yl)amino]-1,3,4-thiadiazol-2-yl}acetamide (UPGL00062)

A mixture of 2-N-[1-(5-amino-1,3,4-thiadiazol-2-yl)piperidin-4-yl]-1,3,4-thiadiazole-2,5-diamine (100 mg, 0.34 mmol), 4-pyridylacetic acid hydrochloride (128 mg, 0.74 mmol) and HATU (319 mg, 0.84 mmol) in anhydrous DMF (2 ml) was treated with DIEA (0.35 mL, 2.01 mmol) and stirred at room temperature until consumption of the limiting reagent was complete. The mixture was then evaporated to a solid residue to which was added water. The suspension formed was then filtered to afford a reddish solid that was then dried, triturated with boiling EtOAc then boiling CH$_2$Cl$_2$ and then boiling MeOH and then chromatographed with column and 0-30% MeOH in CH$_2$Cl$_2$ gradient as eluent to afford the product, 2-(pyridin-4-yl)-N-{5-[(1-{5-[2-(pyridin-4-yl)acetamido]-1,3,4-thiadiazol-2-yl}piperidin-4-yl) amino]-1,3,4-thiadiazol-2-yl}acetamide, as a yellow solid (8 mg, 5% yield). $^1$H NMR (600 MHz, DMSO-d6) δ 1.47-1.55 (m, 2H), 2.01-2.07 (m, 2H), 3.17-3.22 (m, 2H), 3.72-3.78 (m, 3H), 3.78 (s, 2H), 3.80 (s, 2H), 7.31 (distorted t, 4H), 7.40 (d, J=6.6 Hz, 1H), 8.50 (apparent d, J=3.6 Hz, 4H), 12.25 (s, 1H), 12.37 (s, 1H). ATR IR cm$^{-1}$ 2849, 1681, 1575, 1506, 1447, 1417, 1359, 1324, 1268, 1224, 1129, 1083, 1069, 1002, 968, 842, 698, 671, 617.

LCMS (ESI) m/z for $C_{23}H_{24}N_{10}O_2S_2$ calculated: 536.15, observed [M−H]: 535.

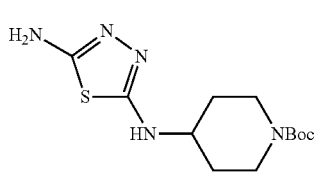

Intermediate 49 tert-Butyl 4-[(5-amino-1,3,4-thiadiazol-2-yl)amino]piperidine-1-carboxylate

A solution of 4-amino-1-N-Boc-piperidine (200 mg, 1.00 mmol), in EtOH (11 mL) was treated with NaHCO$_3$ (336 mg, 4.00 mmol), and 2-amino-5-bromothiadiazole (180 mg, 1.00 mmol) and the resulting mixture was stirred in a sealed vessel at 80° C. until consumption of the starting materials was indicated by TLC. The mixture was then cooled and evaporated to dryness. The residue was treated with water to yield a suspension that was then filtered to afford a yellow solid. The solid was washed with water, dried and chromatographed with column and 0-15% MeOH in CH$_2$Cl$_2$ gradient as eluent to afford the product, tert-butyl 4-[(5-amino-1,3,4-thiadiazol-2-yl)amino]piperidine-1-carboxylate, as a pale-yellow solid (135 mg, 45% yield). $^1$H NMR (600 MHz, DMSO-d6) δ 1.21-1.29 (m, 2H), 1.39 (s, 9H), 1.87-1.92 (m, 2H), 2.81-2.98 (broad s, 2H), 3.51-3.58 (m, 1H), 3.76-3.83 (m, 2H), 6.24 (s, 2H), 6.75 (d, J=7.2 Hz, 1H). ATR IR cm$^{-1}$ 3421, 3364, 3274, 3205, 3136, 3077, 3006, 2973, 2932, 2856, 1680, 1619, 1593, 1528, 1467, 1449, 1428, 1365, 1288, 1273, 1236, 1146, 1079, 1037, 1002, 978, 940, 867, 817, 768, 689, 652, 612. LCMS (ESI) m/z for C$_{12}$H$_{19}$N$_5$O$_2$S calculated: 299.14, observed [M+H]: 300

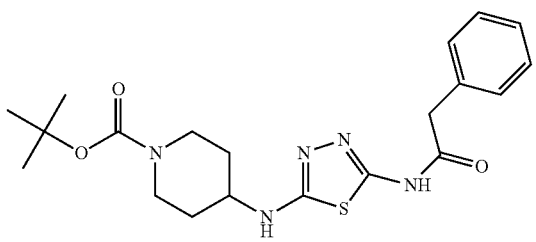 [SMILES: CC(C)(C)OC(=O)N1CCC(Nc2nnc(NC(=O)Cc3ccccc3)s2)CC1]

Intermediate 50 tert-Butyl 4-{[5-(2-phenylacetamido)-1,3,4-thiadiazol-2-yl]amino}piperidine-1-carboxylate A solution of tert-butyl 4-[(5-amino-1,3,4-thiadiazol-2-yl)amino]piperidine-1-carboxylate (118 mg, 0.39 mmol), phenylacetic acid (59 mg, 0.43 mmol), and HATU (225 mg, 0.59 mmol) in anhydrous DMF (1.5 ml) was treated with DIEA (0.21 mL, 1.18 mmol) and the resulting mixture was stirred at room temperature until consumption of the limiting reagent was complete. The mixture was then evaporated to a residue to which water was added. The suspension formed was filtered to afford a reddish-yellow solid that was dried and chromatographed with column and 0-100% EtOAc in hexanes gradient as eluent to give the product, tert-butyl 4-{[5-(2-phenylacetamido)-1,3,4-thiadiazol-2-yl]amino}piperidine-1-carboxylate, as a pale-white solid (101 mg, 62% yield). $^1$H NMR (600 MHz, DMSO-d6) δ 1.23-1.29 (m, 2H), 1.39 (s, 9H), 1.90-1.95 (m, 2H), 2.89 (broad s, 2H), 3.63-3.69 (m, 1H), 3.70 (s, 2H), 3.76-3.84 (m, 2H), 7.25 (distorted t, J=7.2 Hz, 1H), 7.28-7.34 (m, 4H). ATR IR cm$^{-1}$ 3192, 3109, 3007, 2974, 2929, 2849, 1692, 1647, 1581, 1558, 1508, 1452, 1414, 1361, 1319, 1297, 1272, 1239, 1176, 1136, 1090, 1028, 1005, 971, 943, 874, 844, 802, 754, 712, 618. LCMS (ESI) m/z for C$_{20}$H$_{27}$N$_5$O$_3$S calculated: 417.18, observed [M+H]: 418.

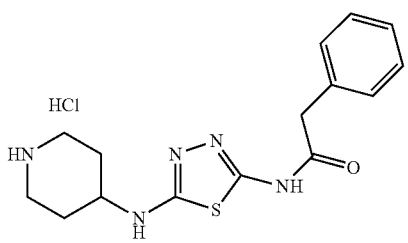 [SMILES: O=C(Cc1ccccc1)Nc1nnc(NC2CCNCC2)s1 ; Cl]

Intermediate 51

2-Phenyl-N-{5-[(piperidin-4-yl)amino]-1,3,4-thiadiazol-2-yl}acetamide hydrochloride A solution of tert-butyl 4-{[5-(2-phenylacetamido)-1,3,4-thiadiazol-2-yl]amino}piperidine-1-carboxylate (85 mg, 0.20 mmol), in anhydrous dioxane (0.5 ml) was treated with a solution of 4M HCl in dioxane (0.25 ml, 1.01 mmol) and stirred at room temperature until consumption of the starting material was complete. The mixture was then evaporated to dryness and the solid residue that was obtained was triturated with hot CH$_2$Cl$_2$ (X2) and with hot hexanes (X2) and then dried to afford the product, 2-phenyl-N-{5-[(piperidin-4-yl)amino]-1,3,4-thiadiazol-2-yl}acetamide hydrochloride, as a white solid (65 mg, 90%). $^1$H NMR (600 MHz, DMSO-d6) δ 1.65-1.73 (m, 2H), 2.07-2.14 (m, 2H), 2.93-3.01 (m, 2H), 3.24-3.31 (m, 2H), 3.74 (s, 2H), 3.82-3.88 (m, 1H), 7.24-7.35 (m, 5H), 8.75-8.89 (m, 2H) 12.47 (s, 1H). ATR IR cm$^{-1}$ 2897, 2774, 2705, 2498, 1683, 1622, 1579, 1486, 1453, 1430, 1389, 1297, 1251, 1218, 1152, 1090, 1037, 973, 936, 902, 843, 799, 782, 749, 718, 694, 618. LCMS (ESI) m/z for free base C$_{15}$H$_{19}$N$_5$OS calculated: 317.13, observed [M+H]: 318.

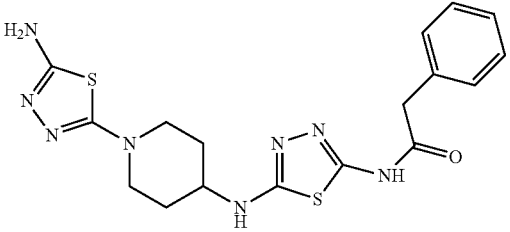 [SMILES: Nc1nnc(N2CCC(Nc3nnc(NC(=O)Cc4ccccc4)s3)CC2)s1]

Example 53

N-(5-{[1-(5-Amino-1,3,4-thiadiazol-2-yl)piperidin-4-yl]amino}-1,3,4-thiadiazol-2-yl)-2-phenylacetamide (UPGL00065)

A mixture of 2-phenyl-N-{5-[(piperidin-4-yl)amino]-1,3,4-thiadiazol-2-yl}acetamide hydrochloride (57 mg, 0.16 mmol), NaHCO$_3$ (67 mg, 0.81 mmol) and 2-amino-5-bromothiadiazole (32 mg, 0.18 mmol) in EtOH (2 ml) was stirred in a sealed vessel at 80° C. until the consumption of the limiting reagent was complete. The mixture was then cooled and evaporated to a solid residue that was treated with water to afford a suspension. Filtration of the suspension afforded a reddish-brown solid that was dried and chromatographed with column and a 0-15% MeOH in CH$_2$Cl$_2$ gradient as eluent to afford the product, N-(5-{[1-(5-amino-1,3,4-thiadiazol-2-yl)piperidin-4-yl]amino}-1,3,4-thiadiazol-2-yl)-2-phenylacetamide, as an orange solid (38 mg, 57% yield). $^1$H NMR (600 MHz, DMSO-d6) δ 1.45-1.53 (m, 2H), 1.98-2.03 (m, 2H), 3.02-3.09 (m, 2H), 3.54-3.60 (m, 2H), 3.70 (s, 2H), 3.69-3.75 (m, 1H), 6.46 (s, 2H), 7.23-7.37 (m, 6H), 12.17 (s, 1H). ATR-IR cm$^{-1}$ 3306, 3240, 3140, 3050, 3027, 2934, 2914, 2843, 2739, 2693, 1649, 1567, 1527, 1489, 1467, 1441, 1386, 1317, 1244, 1218, 1195, 1124, 1098, 1046, 1018, 971, 922, 884, 843, 814, 789, 756, 721, 693, 634.

LCMS (ESI) m/z for C$_{17}$H$_{20}$N$_8$OS$_2$ calculated: 416.12, observed [M−H]: 415.

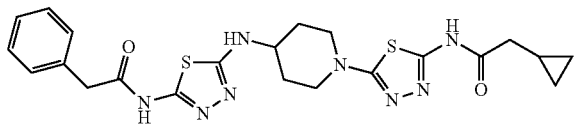 [SMILES: O=C(Cc1ccccc1)Nc1nnc(NC2CCN(c3nnc(NC(=O)CC4CC4)s3)CC2)s1]

Example 54

2-Cyclopropyl-N-[5-(4-{[5-(2-phenylacetamido)-1,3,4-thiadiazol-2-yl]amino}piperidin-1-yl)-1,3,4-thiadiazol-2-yl]acetamide (UPGL00064)

A mixture of N-(5-{[1-(5-amino-1,3,4-thiadiazol-2-yl)piperidin-4-yl]amino}-1,3,4-thiadiazol-2-yl)-2-phenylacetamide (28 mg, 0.07 mmol), cyclopropylacetic acid (7 mg, 0.07 mmol) and HATU (38 mg 0.10 mmol) in anhydrous DMF (0.5 ml) was treated with DIEA (0.20 mmol, 0.04 ml) and stirred at room temperature until consumption of limiting reagents was complete. The reaction mixture was then evaporated to a residue to which water was added. The suspension formed was filtered to afford a pale yellow solid which was then dried and chromatographed with column and 0-15% MeOH in CH$_2$Cl$_2$ gradient as eluent to afford the product, 2-cyclopropyl-N-[5-(4-{[5-(2-phenylacetamido)-1,3,4-thiadiazol-2-yl]amino}piperidin-1-yl)-1,3,4-thiadiazol-2-yl]acetamide, as a pale yellow solid (10 mg, 30%). $^1$H NMR (600 MHz, DMSO-d6) δ 0.15-0.19 (m, 2H), 0.44-0.48 (m, 2H), 0.99-1.05 (m, 1H), 1.48-1.55 (m, 2H), 2.02-2.08 (m, 2H), 2.28 (d, J=6.6 Hz, 2H), 3.17-3.23 (m, 2H), 3.70 (s, 2H), 3.73-3.79 (m, 3H), 7.23-7.34 (m, 5H), 7.37 (d, J=6.6 Hz, 1H), 11.95 (s, 1H), 12.18 (s, 1H). ATR IR cm$^{-1}$ 3330, 2950, 2925, 2837, 2769, 1671, 1561, 1507, 1460, 1380, 1325, 1288, 1255, 1190, 1126, 1104, 967, 927, 831, 752, 695. LCMS (ESI) m/z for C$_{22}$H$_{26}$N$_8$O$_2$S$_2$ calculated: 498.16, observed [M+H]: 499.

Example 55

Biochemical, Cell and Human Liver Microsome (HLM) Stability Assays

Cell culture media and serum were obtained from Invitrogen (Carlsbad, Calif.). All other reagents were obtained from Fisher Scientific (Pittsburgh, Pa.) or Sigma Aldrich (St. Louis, Mo.). MDA-MB-231 cells were purchased from ATCC (Manassas, Va.), and were cultured at 35° C., in 5% CO$_2$, using RPMI-1640 media supplemented with 10% FBS, unless otherwise specified.

Recombinant GAC was expressed in E. coli and purified. Briefly, human GAC (residues 72-603) was cloned into the pET28a vector from Novagen, and was expressed as a His$_6$-tagged fusion protein in E. coli. It was then purified by ion exchange and size exclusion chromatography.

Biochemical assays: The GAC inhibitors were solvated in DMSO. Assay vessels were charged with 1 μL of inhibitor in order to effect the reported final concentration. To each vessel was added 95 μL of an aqueous solution containing 48 mM Tris-acetate (pH 8.6), 21 mM glutamine, and 50 nM recombinant GAC. Fifteen μL of either water or 1 M potassium phosphate, pH 8.2, were added to the mixture to begin the reaction. The assay reagents were incubated for 10 minutes at room temperature, at which point 10 μL of ice-cold 2.4 M hydrochloric acid was added to quench the enzymatic reaction. A second reaction vessel contained 218 μL of an aqueous solution containing 114 mM Tris-HCl (pH 9.4), 0.35 mM ADP, 1.7 mM β-NAD, 238 mM hydrazine, and 1.3 units of glutamate dehydrogenase. A third reaction vessel contained an identical solution except that it lacked NAD$^+$. Forty μL of the initial reaction mixture were added to each of the second and third vessels, which were then incubated at room temperature for one hour. The absorbance of both the second and third reactions was recorded at 340 nM. The third reaction was treated as a baseline, and its absorbance was subtracted from that of the second reaction prior to further data analysis. All experiments were performed a minimum of two times. Dose curves and IC$_{50}$ values were determined in Sigmaplot, using the built-in four parameter logistic function.

Cell assays: MDA-MB-231 cells were cultured in RPMI-1640 media supplemented with 10% FBS. Prior to initiating the assay, cells that were 70-80% confluent were trypsinized. These cells were diluted, counted, and dispensed into 12-well culture plates at a density of 2×10$^4$ cells per well. Each well was then brought to 1 mL of media, total. The cells were allowed to adhere to the wells overnight, at which point they were recounted (day 0 of the assay). At this time, and every 48 hours thereafter, media was exchanged for media containing either the indicated amount of a given inhibitor, diluted from an appropriate DMSO stock, or an equivalent amount of DMSO without inhibitor (0.33% DMSO by volume). Cells were counted on the 6th day of culture. Cell counting was performed by aspirating media, rinsing the cells with room temperature PBS, and then incubating at 37° C. for 5 minutes in 0.5 mL trypsin-EDTA solution. The culture plates were then agitated to fully dissociate cells from the plate surfaces, and 0.5 mL of RPMI-1640 complete media were added to quench trypsin activity. Cells were then counted on a hemocytometer, with 3 readings taken and averaged per sample. All experiments were performed in triplicate. Dose curves and IC$_{50}$ values were determined in Sigmaplot, using the built-in four parameter logistic function.

Human liver microsome (HLM) assay: The method for human liver microsome assays were adapted from Di et al (Journal of biomolecular screening 8.4 (2003): 453-462) and/or Xu et al Journal of the American Society for Mass Spectrometry 13.2 (2002): 155-165). Briefly, test compounds (diluted to final 1 μM (0.4% MeOH/0.1% DMSO)) were tested for metabolic stability by incubation against 1 mg protein/ml of pooled male human liver microsomes for 0 and 30 minutes at 37° C. in the presence and absence of 1 mM NADPH. The reactions are terminated by addition of acetonitrile. Samples are centrifuged and the supernatant fractions analyzed by LC-MS/MS. The instrument responses (i.e. peak areas, heights) at 30 min are referenced to the zero time-point samples to determine the percentage of compound remaining. Appropriate control compounds with known hepatic clearance are included in each assay such as, for instance, metoprolol (control for moderate hepatic clearance), verapamil or testosterone (high hepatic clearance) warfarin (control for low hepatic clearance) etc. The dynamic range for these controls in the microsome preparations provide a reference point for assessing hepatic clearance for unknowns.

In view of the many possible embodiments to which the principles of the disclosed compounds, compositions and methods may be applied, it should be recognized that the illustrated embodiments are only preferred examples of the invention and should not be taken as limiting the scope of the invention.

What is claimed is:

1. A compound, or a pharmaceutically acceptable salt thereof, of structure:

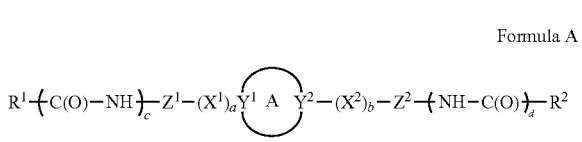

Formula A wherein A is a piperidinyl;
Y$^1$ and Y$^2$ are each independently N or C with the proper valency;
X$^1$ and X$^2$ are each independently —NH—, —O—, —CH$_2$—O—, provided that when at least one of X$^1$ and X$^2$ is —CH$_2$—O—, then the —CH$_2$— is directly connected to A;
a and b are each independently 0 or 1;
c and d are each independently 0 or 1;
Z$^1$ and Z$^2$ are each independently selected from thiadiazole, pyridazine, or pyridine; and
R$^1$ and R$^2$ are each independently optionally substituted alkyl, optionally substituted aralkyl, optionally substituted cycloalkyl, amino, optionally substituted heteroaralkyl, optionally substituted alkylalkoxy, optionally substituted alkylaryloxy, optionally substituted aryl, optionally substituted heteroaryl, or optionally substituted heterocycloalkyl;
provided that if Y$^1$ is N and Y$^2$ is C, then a=0 and b=1;
provided that if Y$^1$ is C and Y$^2$ is N, then a=1 and b=0;
provided that if c=0 and d=0, then R$^1$ and R$^2$ are both amino;
provided that if c is 1 and d is 1, then both R$^1$ and R$^2$ are not amino;
provided that if c is 0 and d is 1, then R$^1$ is amino and R$^2$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl; and
provided that if c is 1 and d is 0, then R$^2$ is amino and R$^1$ is optionally substituted alkyl, optionally substituted aralkyl, optionally substituted cycloalkyl, optionally substituted heteroaralkyl, optionally substituted alkylalkoxy, optionally substituted alkylaryloxy, optionally substituted aryl, optionally substituted heteroaryl, or optionally substituted heterocycloalkyl.

2. The compound of claim 1, wherein A is selected from:

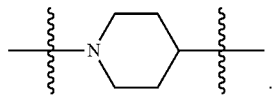

3. The compound of claim 1, wherein at least one of a orb is 1.
4. The compound of claim 1, wherein at least one of X$^1$ or X$^2$ is —NH—, —O—, or —CH$_2$—O—.
5. The compound of claim 1, wherein a is 1, b is 0, and X$^1$ is —NH—, —O—, or —CH$_2$—O—.
6. The compound of claim 1, wherein a is 0, b is 1, and X$^2$ is —NH—, —O—, or —CH$_2$—O—.
7. The compound of claim 1, wherein Z$^1$ and Z$^2$ are each the same.
8. The compound of claim 1, wherein Z$^1$ and Z$^2$ are each independently selected from:

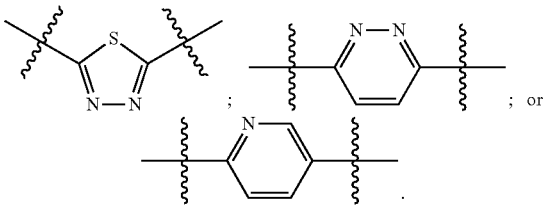

9. The compound of claim 1, wherein c and d are each 1.
10. The compound of claim 1, wherein at least one of R$^1$ and R$^2$ is benzyl or optionally-substituted benzyl, methyl, pyridinylmethyl, or cyclopropylmethyl.
11. The compound of claim 1, wherein c and d are each 0, and R$^1$ and R$^2$ are each —NH$_2$.
12. The compound of claim 1, wherein c is 1, R$^1$ is optionally-substituted benzyl, methyl, pyridinylmethyl, or cyclopropylmethyl, d is 0, and R$^2$ is —NH$_2$.
13. The compound of claim 1, wherein c is 0, R$^1$ is —NH$_2$, d is 1, and R$^2$ is optionally-substituted benzyl, methyl, pyridinylmethyl, or cyclopropylmethyl.
14. The compound of claim 1, wherein Z$^1$ and Z$^2$ groups are each

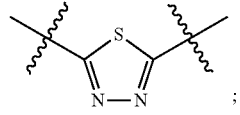 [SMILES: *c1nnc(*)s1]

c and d are each 1; and at least one of R$^1$ and R$^2$ is benzyl or substituted benzyl.
15. The compound of claim 1, wherein the compound is selected from 2-Phenyl-N-{5-[1-(5-phenylacetylamino-[1,3,4]thiadiazol-2-yl)-piperidin-4-yloxy]-[1,3,4]thiadiazol-2-yl}-acetamide;
N-{5-[1-(5-Acetylamino-[1,3,4]thiadiazol-2-yl)-piperidin-4-yloxy]-[1,3,4]thiadiazol-2-yl}-acetamide;
N-{5-[1-(5-Amino-[1,3,4]thiadiazol-2-yl)-piperidin-4-yloxy]-[1,3,4]thiadiazol-2-yl}-2-phenyl-acetamide;
2-(Pyridin-3-yl)-N-(5-(4-((5-(2-(pyridin-3-yl)acetamido)-1,3,4-thiadiazol-2-yl)oxy)piperidin-1-yl)-1,3,4-thiadiazol-2-yl)acetamido;

2-Cyclopropyl-N-(5-(4-((5-(2-cyclopropylacetamido)-1,3,4-thiadiazol-2-yl)oxy)piperidin-1-yl)-1,3,4-thiadiazol-2-yl)acetamido;
2-Phenyl-N-{6-[1-(6-phenylacetylamino-pyridazin-3-yl)-piperidin-4-yloxy]-pyridazin-3-yl}-acetamide;
2-Phenyl-N-(5-(4-((5-(2-phenylacetamido)-1,3,4-thiadiazol-2-yl)amino)piperidin-1-yl)-1,3,4-thiadiazol-2-yl)acetamido;
2-Phenyl-N-{6-[1-(5-phenylacetylamino-[1,3,4]thiadiazol-2-yl)-piperidin-4-yloxy]-pyridazin-3-yl}-acetamide;
N-(6-[1-{5-(2-Pyridin-2-yl-acetylamino)-[1,3,4]thiadiazol-2-yl]-piperidin-4-yloxy}-pyridazin-3-yl)-2-(3-trifluoromethoxy-phenyl)-acetamide;
2-Phenyl-N-[5-{1-(5-phenylacetylamino-[1,3,4]thiadiazol-2-yl)-piperidin-4-ylmethoxy]-[1,3,4]thiadiazol-2-yl]-acetamide;
2-(Pyridin-2-yl)-N-{5-[(1-{5-[2-(pyridin-2-yl)acetamido]-1,3,4-thiadiazol-2-yl}piperidin-4-yl)amino]-1,3,4-thiadiazol-2-yl}acetamido;
2-(Pyridin-3-yl)-N-{5-[(1-{5-[2-(pyridin-3-yl)acetamido]-1,3,4-thiadiazol-2-yl}piperidin-4-yl)amino]-1,3,4-thiadiazol-2-yl}acetamido;
2-(Pyridin-2-yl)-N-{5-[(1-{5-[2-(pyridin-2-yl)acetamido]-1,3,4-thiadiazol-2-yl}piperidin-4-yl)oxy]-1,3,4-thiadiazol-2-yl}acetamido;
2-(Pyridin-4-yl)-N-{5-[(1-{5-[2-(pyridin-4-yl)acetamido]-1,3,4-thiadiazol-2-yl}piperidin-4-yl)amino]-1,3,4-thiadiazol-2-yl}acetamido; or
2-Cyclopropyl-N-[5-(4-{[5-(2-phenylacetamido)-1,3,4-thiadiazol-2-yl]amino}piperidin-1-yl)-1,3,4-thiadiazol-2-yl]acetamido.

16. The compound of claim 1, wherein the compound is selected from

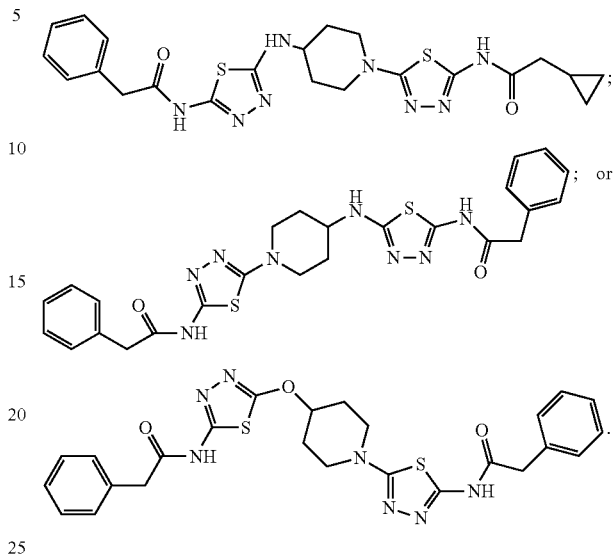

17. A pharmaceutical composition comprising at least one compound of claim 1, and a pharmaceutically acceptable additive.

\* \* \* \* \*